US007220875B2

(12) United States Patent
Gallop et al.

(10) Patent No.: US 7,220,875 B2
(45) Date of Patent: May 22, 2007

(54) AMINO ACID DERIVED PRODRUGS OF PROPOFOL, COMPOSITIONS AND USES THEREOF

(76) Inventors: Mark A. Gallop, 511 Orange Ave., Los Altos, CA (US) 94022; Feng Xu, 2129 Edgewood Dr., Palo Alto, CA (US) 94303; Kenneth C. Cundy, 45 Summit Ridge Pl., Redwood City, CA (US) 94602; Vivek Susikumar, 3707 Poinciana Dr., Santa Clara, CA (US) 95051; Thomas W. Woiwode, 1945 Eucalyptus Ave., San Carlos, CA (US) 94070

( * ) Notice: Subject to any disclaimer, the term of this patent is extended or adjusted under 35 U.S.C. 154(b) by 455 days.

(21) Appl. No.: 10/766,990

(22) Filed: Jan. 28, 2004

(65) Prior Publication Data
US 2005/0004381 A1 Jan. 6, 2005

Related U.S. Application Data

(60) Provisional application No. 60/443,315, filed on Jan. 28, 2003.

(51) Int. Cl.
*C07C 229/00* (2006.01)
*A61K 31/385* (2006.01)
(52) U.S. Cl. .................................. 560/19; 514/534
(58) Field of Classification Search .............. 560/19; 514/534
See application file for complete search history.

(56) References Cited

U.S. PATENT DOCUMENTS

| 3,845,770 | A | 11/1974 | Theeuwes et al. |
| 3,916,899 | A | 11/1975 | Theeuwes et al. |
| 4,765,539 | A | 8/1988 | Noakes et al. |
| 4,962,885 | A | 10/1990 | Coffee |
| 5,112,598 | A | 5/1992 | Biesalski |
| 5,556,611 | A | 9/1996 | Biesalski |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | van Der Linder et al. |
| 6,204,257 | B1 | 3/2001 | Stella et al. |
| 6,254,853 | B1 | 7/2001 | Hendler et al. |
| 6,362,234 | B1 | 3/2002 | Hendler |
| 6,451,776 | B2 | 9/2002 | Stella et al. |

FOREIGN PATENT DOCUMENTS

| WO | WO 94/12285 A2 | 6/1994 |
| WO | WO 94/12285 A3 | 6/1994 |
| WO | WO 94/14543 A2 | 7/1994 |
| WO | WO 94/14543 A3 | 7/1994 |
| WO | WO 95/26234 A1 | 10/1995 |
| WO | WO 95/26235 A1 | 10/1995 |
| WO | WO 95/32807 A1 | 12/1995 |
| WO | WO 99/58555 A2 | 11/1999 |
| WO | WO 99/58555 A3 | 11/1999 |
| WO | WO 00/48572 A1 | 8/2000 |
| WO | WO 00/54588 A1 | 9/2000 |
| WO | WO 02/13810 A1 | 2/2002 |

OTHER PUBLICATIONS

Adibi, "The oligopeptide transporter (Pept-1) in Human Intestine: Biology and Function," *Gastroenterology* 1997, 113, 332-340.
Alderman, "A Review of Cellulose Ethers in Hydrophilic Matrices of Oral controlled-Release Dosage Forms," *Int. J. Pharm. Tech. & Prod. Mfr.* 1984, 5(3) 1-9.
Anderson et al., "Alpha-amino acid phenolic ester derivatives: novel water-soluble general anesthetic agents which allosterically modulate GABA(A) receptors," *J. Med. Chem.* 2001, 44, 3582-3591.
Bamba et al., "Release Mechanisms in Gelforming Sustained Release Preparations," *Int. J. Pharm.* 1979, 2, 307.
Banaszczyk et al., "Propofol Phosphate, a Water-Soluble Propofol Prodrug: In Vivo Evaluation," *Anesth. Analg.* 2002, 95, 1285-1292.
Borgeat et al., "Adjuvant Propofol enables better control of nausea and emesis secondary to chemotherapy for breast cancer," *Can. J. Anaesth.* 1994, 41, 1117-1119.
Borgeat et al., "Propofol improves patient comfort during cisplatin chemotherapy. A pilot study," *Oncology* 1993, 50, 456-459.
Briggs et al., "An adverse Reaction to the administration of disoprofol (Diprivan)," *Anaesthesia* 1982, 37, 1099-1101.
Brooker et al., "Propofol Maintenance to Reduce Postoperatiove Emesis in Thyroidectomy Patients: A Group Sequential Comparison with Isoflurane/Nitrous Oxide," *Anaesth. Intensive Care* 1998, 26, 625-629.
Brown et al., "Role of Propofol in Refractory Status Epilepticus," *Pharmacother.* 1998, 32, 1053-1059.
De la Cruz et al., "The Effect of Propofol on Oxidative Stress in Platelets from Surgical Patients," *Anesth. Analg.* 1999, 89, 1050-1055.
During et al., "Controlled release of dopamine from a polymeric brain implant: in vivo characterization," 1989, *Ann. Neurol.* 25:351.
Gan et al., "Determination of Plasma Concentrations of Propofol Associated with 50% Reduction in Postoperative Nausea," *Anesthesiology*, 1997, 87, 779-784.
Hasan et al., "Comparison of the Effects of the Propofol and Thiopental on the Pattern of Maximal Electroshock Seizures in a Rat," *Pharmacol. Toxicol.* 1994, 74, 50-53.
Holtkamp et al., "Propofol in subanesthetic doses terminates Status epilepticus in a rodent model," *Ann. Neurol.* 2001, 49, 260-263.
Howard et al., "Intercerebral Drug Delivery in Rats with Lesion-Induced Memory Deficits," 1989, *J. Neurosurg.* 71:105-112.

(Continued)

*Primary Examiner*—Deborah C. Lambkin
(74) *Attorney, Agent, or Firm*—Timothy A. Worrall; Dorsey & Whitney LLP

(57) ABSTRACT

The present invention provides propofol prodrugs, methods of making propofol prodrugs, pharmaceutical compositions of propofol prodrugs and methods of using propofol prodrugs and pharmaceutical compositions thereof to treat or prevent diseases or disorders such as migraine headache pain and post-chemotherapy or post-operative surgery nausea and vomiting.

48 Claims, No Drawings

OTHER PUBLICATIONS

Krusz et al., "Intravenous Propofol: Unique Effectiveness in Treating Intractable Migraine," *Headache* 2000, 40, 224-230.

Kuisma et al., Propofol in prehospital Treatment of convulsive status epilepticus. *Epilepsia* 1995, 36, 1241-1243.

Langer et al., "Chemical and Physical Structure of Polymers as Carriers for Controlled Relaease of Bioactive Agents: A Review," *J Macromol. Sci. Rev. Macromol Chem.* 1983, 23:61.

Langley et al., "Propofol. A review of its pharmacodynamic and Pharmacokinetic properties and use as an intravenous anaesthetic," *Drugs* 1988, 35, 334-372.

Leibach et al., "Peptide transporters in the Intestine and the kidney," *Ann. Rev. Nutr.* 1996, 16, 99-119.

Levy et al., "Inhibition of Calcification of Bioprosthetic Heart Valves by Local Controlled-Release Diphosphonate,"0 *Science* 1985 228: 190-192.

Murphy et al., "The Antioxidant Potential of Propofol (2,6-Diisopropylphenol)," *Br. J. Anaesth.* 1992, 68, 613-618.

Peduto et al., "Biochemical and Electrophysiologic Evidence That Propofol Enchances GABAergic Transmission in the Rat Brain," *Anesthesiology* 1991, 75, 1000-1009.

Phelps et al., "Propofol in Chemotherapy-Associated Nausea and Vomiting," *Ann. Pharmacother.* 1996, 30, 290-292.

Picard et al., "Prevention of Pain on Injection with Propofol: A Quantitative Systematic Review," 2000, 90, 963-969.

Pop et al., "Synthesis and Preliminary Pharmacological Evaluation of Some Chemical Delivery Systems of 2,6-Diisopropylphenol (Propofol)," *Med. Chem. Res.* 1992, 2, 16-21.

Raleigh et al., "Pharmacokinetics of Isotretinoin (ISO) in Rats Following Oral Dosing or Aerosol Inhalation," *British J. Cancer*, 1999, 80, Suppl. 2, 96.

Raleigh et al., "Searching for the Link Between Hypoxia and Poor Prognoses in Human Tumors," *Proc. Amer. Assoc. Cancer Research Annual Meeting*, 1999, 40, 397..

Raoof et al., "In Vivo Assessment of Intestinal Hepatic, and Pulmonary First Pass Metabolism of Propofol in the Rat," *Pharm. Res.* 1996, 13, 891-895.

Sagara et al., "Propofol Hemisuccinate Protects Neuronal Cells from Oxidative Injury," *J. Neurochem.* 1999, 73, 2524-2530.

Saudek et al., "A Preliminary Trial of the Programmable Implantable Medication System for Insulin Delivery," *N. Engl. J. Med.*, 1989, 321: 574.

Sefton, "Implantable Pumps," *CRC Crit Ref Biomed. Eng.* 1987, 14:201.

Simonian et al., "Oxidative Stress in Neurodegenerative Diseases," Pharmacol. Toxicol. 1996, 83-106.

Sutherland et al., "Propofol and Seizures," *Anaesth. Intensive Care* 1994, 22, 733-737.

Tomioka et al., "Propofol Is Effective in Chemotherapy-Induced Nausea and Vomiting: A Case Report with Quantitative Analysis," *Anesth. Analg.* 1999, 89, 798-799.

Tramer et al., "Propofol Anaesthesia and Postoperative Nausea and Vomiting Quantitative and Systemic Review of Randomized Controlled Studies," *Br. J. Anaesth.* 1997, 78, 247-255.

Trapani et al., "Propofol Analogues. Synthesis, Relationships Between Structure and Affinity for $GABA_A$ Receptors," *J. Med. Chem.* 1998, 41, 1846-1854.

Trapani et al., "Water-Soluble Salts of Aminoacid Esters of the Anesthetic Agent Propofol," *Int. J. Pharm.* 1998, 175, 195-204.

Verma et al., "Osmotically Controlled Oral Drug Delivery," *Drug Dev. Ind. Pharm.*, 2000, 26:695-708.

Walder et al., "Seizure-like phenomena and propofol," *Neurology* 2002, 58, 1327-1332.

Wang et al. "Propofol reduces infarct size and striatal dopamine accumulation following transient middle cerebral artery occlusion: a microdialysis study," *Eur. J. Pharmacol.* 2002, 452, 303-308.

Young et al., "Propofol neuroprotection in a rat model of Ischaemia reperfusion injury," *Eur. J. Anaesthesiol.* 1997, 14, 320-326.

AMINO ACID DERIVED PRODRUGS OF PROPOFOL, COMPOSITIONS AND USES THEREOF

This application claims the benefit under 35 U.S.C. § 119(e) of U.S. Provisional Application Ser. No. 60/443,315, filed Jan. 28, 2003. The above application is incorporated herein by reference in their entirety.

1. TECHNICAL FIELD

The present invention provides propofol prodrugs, methods of making propofol prodrugs, pharmaceutical compositions of propofol prodrugs and methods of using propofol prodrugs and pharmaceutical compositions thereof to treat or prevent diseases or disorders such as migraine headache pain and post-chemotherapy or post-operative surgery nausea and vomiting.

2. BACKGROUND ART

Propofol (2,6-diisopropylphenol), (1), is a low molecular weight phenol that is widely used as an intravenous sedative-hypnotic agent in the induction and maintenance of anesthesia and/or sedation in mammals. The advantages of propofol as an anesthetic include rapid onset of anesthesia, rapid clearance, and minimal side effects (Langley et al., *Drugs* 1988, 35, 334–372). Propofol may mediate hypnotic effects through interaction with the $GABA_A$ receptor complex, a hetero-oligomeric ligand-gated chloride ion channel (Peduto et al., *Anesthesiology* 1991, 75, 1000–1009.).

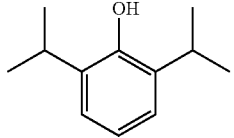

Propofol (1)

Propofol is rapidly metabolized in mammals with the drug being eliminated predominantly as glucuronidated and sulfated conjugates of propofol and 4-hydroxypropofol (Langley et al., *Drugs* 1988, 35, 334–372). Propofol clearance exceeds liver blood flow, which indicates that extrahepatic tissues contribute to the overall metabolism of the drug. Human intestinal mucosa glucuronidates propofol in vitro and oral dosing studies in rats indicate that approximately 90% of the administered drug undergoes first pass metabolism, with extraction by the intestinal mucosa accounting for the bulk of this presystemic elimination (Raoof et al., *Pharm. Res.* 1996, 13, 891–895). Because of its extensive first-pass metabolism, propofol is administered by injection or intravenous infusion and oral administration has not been considered therapeutically effective.

Propofol has a broad range of biological and medical applications, which are evident at sub-anesthetic doses and include treatment and/or prevention of intractable migraine headache pain (Krusz et al., *Headache* 2000, 40, 224–230; Krusz, International Publication No. WO 00/54588). Propofol, when used to maintain anesthesia, causes a lower incidence of post-operative nausea and vomiting ("PONV") when compared to common inhalation anesthetic agents and numerous controlled clinical studies support the anti-emetic activity of propofol (Tramer et al., *Br. J. Anaesth.* 1997, 78, 247–255; Brooker et al., *Anaesth. Intensive Care* 1998, 26, 625–629; Gan et al., *Anesthesiology* 1997, 87, 779–784). Propofol has also been shown to have anti-emetic activity when used in conjunction with chemotherapeutic compounds (Phelps et al., *Ann. Pharmacother.* 1996, 30, 290–292; Borgeat et al., *Oncology* 1993, 50, 456–459; Borgeat et al., *Can. J. Anaesth.* 1994, 41, 1117–1119; Tomioka et al., *Anesth. Analg.* 1999, 89, 798–799). Nausea, retching and/or vomiting induced by a variety of chemotherapeutic agents (e.g., cisplatin, cyclophosphamide, 5-fluorouracil, methotrexate, anthracycline drugs, etc.) has been controlled by low-dose propofol infusion in patients refractory to prophylaxis with conventional anti-emetic drugs (e.g., serotonin antagonists and corticosteroids).

Propofol has also been used to treat patients with refractory status epilepticus (Brown et al., *Pharmacother.* 1998, 32, 1053–1059; Kuisma et al., *Epilepsia* 1995, 36, 1241–1243; Walder et al., *Neurology* 2002, 58, 1327–1332; Sutherland et al., *Anaesth. Intensive Care* 1994, 22, 733–737). Further, the anticonvulsant effects of propofol have also been demonstrated in rat efficacy models at sub-anesthetic doses (Holtkamp et al., *Ann. Neurol.* 2001, 49, 260–263; Hasan et al., *Pharmacol. Toxicol.* 1994, 74, 50–53).

Propofol has also been used as an antioxidant (Murphy et al., *Br. J. Anaesth.* 1992, 68, 613–618; Sagara et al., *J. Neurochem.* 1999, 73, 2524–2530; Young et al., *Eur. J. Anaesthesiol.* 1997, 14, 320–326; Wang et al. *Eur. J. Pharmacol.* 2002, 452, 303–308). Propofol, at doses typically used for surgical anesthesia, has observable antioxidant effects in humans (De la Cruz et al., *Anesth. Analg.* 1999, 89, 1050–1055). Pathogenesis or subsequent damage pathways in various neurodegenerative diseases involve reactive oxygen species and accordingly may be treated or prevented with antioxidants (Simonian et al., *Pharmacol. Toxicol.* 1996, 36, 83–106). Examples of specific neurodegenerative diseases which may be treated or prevented with antioxidants include, but are not limited to, Friedrich's disease, Parkinson's disease, Alzheimer's disease, Huntington's disease, amyotrophic lateral sclerosis ("ALS"), multiple sclerosis ("MS"), Pick disease, inflammatory diseases and diseases caused by inflammatory mediators such as tumor necrosis factor (TNF) and IL-1.

A significant problem with the formulation and use of propofol is poor water solubility. Accordingly, propofol must be specially formulated in aqueous media using solubilizers or emulsifiers (Briggs et al., *Anaesthesia* 1982, 37, 1099–1101). For Example, in a current commercial product (Diprivan®, Astra-Zeneca) an oil-in-water emulsion (the emulsifier is the lecithin mixture Intralipid®), is used to formulate propofol (Picard et al., *Anesth. Analg.* 2000, 90, 963–969). Unfortunately, the oil-in-water emulsion formulation causes discomfort and pain at the site of injection.

One potential solution to the poor water solubility of propofol which avoids the use of additives, solubilizers or emulsifiers and the attendant injection site pain, is a water-soluble, stable propofol prodrug that is converted to propofol in vivo. (Hendler et al., International Publication No. WO 99/58555; Morimoto et al., International Publication No. WO 00/48572; Hendler et al., U.S. Pat. No. 6,254,853; Stella et al., *United States Patent Application No. US*2001/ 0025035; Hendler, U.S. Pat. No. 6,362,234; Hendler, International Publication No. WO 02/13810; Sagara et al., *J. Neurochem.* 1999, 73, 2524–2530; Banaszczyk et al., *Anesth. Analg.* 2002, 95, 1285–1292; Trapani et al., *Int. J. Pharm.* 1998, 175, 195–204; Trapani et al., *J. Med. Chem.* 1998, 41, 1846–1854; Anderson et al., *J. Med. Chem.* 2001, 44, 3582–3591; Pop et al., *Med. Chem. Res.* 1992, 2, 16–21).

A significant problem with these existing propofol prodrugs is their high stability in vivo. This stability prevents release of therapeutically significant concentrations of propofol, particularly when the prodrug is orally administered.

Accordingly, there is a need for propofol prodrugs, which are sufficiently labile under physiological conditions to provide therapeutically effective concentrations of propofol, particularly, when the prodrug is orally administered.

3. SUMMARY

Disclosed herein are propofol prodrugs, methods of making propofol prodrugs, pharmaceutical compositions of propofol prodrugs and methods of using propofol prodrugs to treat or prevent diseases or disorders such as migraine headache pain, neurodegenerative disorders and post-chemotherapy or post-operative surgery nausea and vomiting which satisfies the above need. In one embodiment, prodrugs of propofol and pharmaceutical compositions thereof are orally administered. In another embodiment, prodrugs of propofol are translocated across the gastrointestinal mucosa via interaction with transporter proteins expressed within enterocytes lining the gastrointestinal tract.

In a first aspect, a compound of structural Formula (I) is provided:

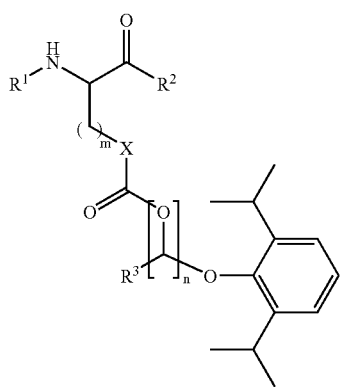

(I)

or a pharmaceutically acceptable salt, hydrate, solvate or N-oxide thereof, wherein:

X is selected from the group consisting of a bond, —$CH_2$—, —$NR^{11}$—, —O— and —S—;

m is 1 or 2;

n is 0 or 1;

$R^1$ is selected from the group consisting of hydrogen, [$R^5NH(CHR^4)_pC(O)$]—, $R^6$—, $R^6C(O)$— and $R^6OC(O)$—;

$R^2$ is —$OR^7$ or —[$NR^8(CHR^9)_qC(O)OR^7$];

p and q are independently 1 or 2;

$R^3$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

each $R^4$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^4$ and $R^5$ are attached to adjacent atoms then $R^4$ and $R^5$ together with the atoms to which they are bonded form a cycloheteroalkyl or substituted cycloheteroalkyl ring;

$R^5$ is selected from the group consisting of hydrogen, $R^6$—, $R^6C(O)$— and $R^6OC(O)$—;

$R^6$ is selected from the group consisting of alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

$R^7$ is selected from the group consisting of hydrogen, alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

$R^8$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

each $R^9$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^8$ and $R^9$ are attached to adjacent atoms then $R^8$ and $R^9$ together with the atoms to which they are bonded form a cycloheteroalkyl or substituted cycloheteroalkyl ring;

$R^{11}$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

with the provisos that:

when $R^1$ is [$R^5NH(CHR^4)_pC(O)$]— then $R^2$ is —$OR^7$;

and when $R^2$ is —[$NR^8(CHR^9)_qC(O)OR^7$] then $R^1$ is not [$R^5NH(CHR^4)_pC(O)$]—.

In a another aspect, a compound of structural Formula (II) is provided:

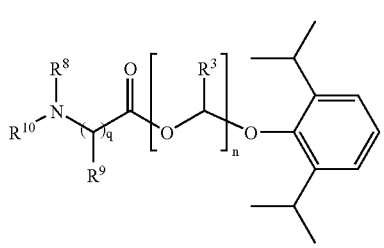

(II)

or a pharmaceutically acceptable salt, hydrate, solvate or N-oxide thereof, wherein:

$R^{10}$ is hydrogen or [$R^5NH(CHR^4)_pC(O)$]—;

n is 0 or 1;

p and q are independently 1 or 2;

each of $R^3$, $R^4$, $R^5$, $R^8$ and $R^9$ is as described above;

with the proviso that when $R^{10}$ is hydrogen then n is 1.

In still another aspect, pharmaceutical compositions are provided. The pharmaceutical compositions disclosed herein generally comprise one or more compounds of Formulae (I)–(XVIII), and a pharmaceutically acceptable vehicle such as a diluent, carrier, excipient or adjuvant. The choice of diluent, carrier, excipient and adjuvant will depend upon, among other factors, the desired mode of administration. In one embodiment, the mode of administration is oral.

In still another aspect, methods for treating various diseases or disorders are provided. The methods disclosed herein generally comprise administering one or more compounds of Formulae (I)–(XVIII) in order to achieve a therapeutically effective concentration of propofol in the blood and/or tissue of a patient. The methods are useful for treating or preventing diseases or disorders including, but not limited to, migraine headache pain, post-chemotherapy or post-operative surgery nausea and vomiting and neurodegenerative disorders (e.g., epilepsy, Friedrich's disease, Parkinson's disease, Alzheimer's disease, Huntington's disease, amyotrophic lateral sclerosis (ALS), multiple sclerosis (MS), Pick disease, etc.). The methods generally involve administering to a patient in need of such treatment or prevention a therapeutically effective amount of one or more compounds of Formulae (I)–(XVIII), or pharmaceutical composition containing one or more compounds of Formulae (I)–(XVIII).

In still another aspect, methods for inducing and/or maintaining anesthesia or sedation in a mammal are provided. The methods generally involve administering to a patient in need of such anesthesia or sedation induction and/or maintenance a therapeutically effective amount of one or more compounds of Formulae (I)–(XVIII), or pharmaceutical composition containing one or more compounds of Formulae (I)–(XVIII).

4. DETAILED DESCRIPTION

4.1 Definitions

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, even more preferably, 1 to 6 carbon atoms. "$C_{1-6}$ alkyl" refers to an alkyl group containing from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{30}$, where $R^{30}$ is hydrogen, alkyl, cycloalkyl, cycloheteroalkyl, aryl, arylalkyl, heteroalkyl, heteroaryl, heteroarylalkyl as defined herein. Representative Examples include, but are not limited to formyl, acetyl, cyclohexylcarbonyl, cyclohexylmethylcarbonyl, benzoyl, benzylcarbonyl and the like.

"Alkoxy" by itself or as part of another substituent refers to a radical —O$R^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent, refers to a radical —C(O)O$R^{31}$ where $R^{31}$ is as defined above.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysenei, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, from 6 to 12 carbon atoms.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$)

and the aryl moiety is ($C_6$–$C_{20}$), more preferably, an arylalkyl group is ($C_6$–$C_{20}$) arylalkyl, e.g., the alkanyl, alkenyl or alkynyl moiety of the arylalkyl group is ($C_1$–$C_8$) and the aryl moiety is ($C_6$–$C_{12}$).

"Carbamoyl" by itself or as part of another substituent refers to the radical —C(O)N($R^{32}$)$R^{33}$ where $R^{32}$ and $R^{33}$ are independently hydrogen, alkyl, substituted alkyl, aryl, substituted aryl, arylalkyl, substituted arylalkyl, heteroarylalkyl, substituted heteroarylalkyl, heteroaryl or substituted heteroaryl, as defined herein.

"Compounds" as used herein refer to compounds encompassed by the generic formulae disclosed herein and include any specific compounds within those formulae whose structure is disclosed herein. The compounds may be identified either by their chemical structure and/or chemical name. When the chemical structure and chemical name conflict, the chemical structure is determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, and $^{18}$O. Compounds may exist in unsolvated forms as well as solvated forms, including hydrated forms and as N-oxides. In general, the hydrated, solvated and N-oxide forms are within the scope of the present invention. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is ($C_3$–$C_{10}$) cycloalkyl, more preferably, ($C_3$–$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —N$R^{34}R^{35}$—, =N—N=, —N=N—, —N=N—N$R^{36}R^{37}$, —P$R^{38}$—, —P(O)$_2$—, —POR$^{39}$—, —O—P(O)$_2$—, —SO—, —SO$_2$—, —Sn$R^{40}R^{41}$— and the like, where $R^{34}$, $R^{35}$, $R^{36}$, $R^{37}$, $R^{38}$, $R^{39}$, $R^{40}$ and $R^{41}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5–20 membered heteroaryl, more preferably from 5–10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl, more preferably, 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for Example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for Example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutical composition" refers to at least one compound of Formulae (I) or (II) and a pharmaceutically acceptable vehicle, with which the compound is administered to a patient.

"Pharmaceutically acceptable salt" refers to a salt of a compound of Formulae (I) or (II), which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of Formulae (I) or (II) is administered.

"Patient" includes humans. The terms "human" and "patient" are used interchangeably herein.

"PEPT1" refers to an oligopeptide transporter protein that normally absorbs dipeptides and tripeptides (and related structures) in certain tissues, such as the intestine (Adibi, S. A., *Gastroenterology* 1997, 113, 332–340; Leibach et al., *Ann. Rev. Nutr.* 1996, 16, 99–119).

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for Example, to an ester, carbonate, acyloxyalkyl or a sulfonate prodrug, which may be hydrolyzed in vivo to provide the hydroxyl compound. Prodrugs for drugs which functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, -M, $—R^{60}$, $—O^-$, $=O$, $—OR^{60}$, $—SR^{60}$, $—S_-$, $=S$, $—NR^{60}R^{61}$, $=NR^{60}$, $—CF_3$, $—CN$, $—OCN$, $—SCN$, $—NO$, $—NO_2$, $=N_2$, $—N_3$, $—S(O)_2O^-$, $—S(O)_2OH$, $—S(O)_2R^{60}$, $—OS(O_2)O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, $—C(O)O^-$, $—C(S)OR^{60}$, $—NR^{62}C(O)NR^{60}R^{61}$, $—NR^{62}C(S)NR^{60}R^{61}$, $—NR^{62}C(NR^{63})NR^{60}R^{61}$ and $—C(NR^{62})NR^{60}R^{61}$ where M is independently a halogen; $R^{61}$, $R^{60}R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, $—R^{60}$, $=O$, $—OR^{60}$, $—SR^{60}$, $—S^-$, $=S$, $—NR^{60}R^{61}$, $=NR^{60}$, $—CF_3$, $—CN$, $—OCN$, —SCN, —NO, —NO$_2$, =N$_2$, —N$_3$, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —NR$^{62}$C(O)NR$^{60}$R$^{61}$, more preferably, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$, most preferably, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, —C(O)O$^-$, where R$^{60}$, R$^{61}$ and R$^{62}$ are as defined above.

"Transported by the PEPT1 transporter" refers to the translocation of a molecule across a membrane of a cell expressing the PEPT1 transporter. The translocation occurs through interaction with the transporter and is energized by cotransport of H$^+$ ions across the membrane.

"Treating" or "treatment" of any disease or disorder refers to one or more of the following: (1) ameliorating the disease or disorder (i.e., arresting or reducing the development of the disease or at least one of the clinical symptoms thereof); (2) ameliorating at least one physical parameter, which may not be discernible by the patient; (3) inhibiting the disease or disorder, either physically, (e.g., stabilization of a discernible symptom), physiologically, (e.g., stabilization of a physical parameter), or both; and (4) delaying the onset of the disease or disorder.

"Therapeutically effective amount" means the amount of a compound or composition that, when administered to a patient, is sufficient to effect the desired therapy. The "therapeutically effective amount" will vary depending on the compound, the disease and its severity and the age, weight, etc., of the patient to be treated.

Reference will now be made in detail to certain preferred compounds and methods of making and administering these compounds. The invention is not limited to those preferred compounds and methods but rather is defined by the claim(s) issuing herefrom.

4.2 Compounds

The compounds disclosed herein are prodrugs of propofol. A first class of propofol prodrugs include compounds of structural Formula (I):

or a pharmaceutically acceptable salt, hydrate, solvate or N-oxide thereof, wherein:

X is selected from the group consisting of a bond, —CH$_2$—, —NR$^{11}$—, —O— and —S—;

m is 1 or 2;

n is 0 or 1;

R$^1$ is selected from the group consisting of hydrogen, [R$^5$NH(CHR$^4$)$_p$C(O)]—, R$^6$—, R$^6$C(O)— and R$^6$C(O)—;

R$^2$ is —OR$^7$ or —[NR$^8$(CHR$^9$)$_q$C(O)OR$^7$];

p and q are independently 1 or 2;

R$^3$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

each R$^4$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when R$^4$ and R$^5$ are attached to adjacent atoms then R$^4$ and R$^5$ together with the atoms to which they are bonded form a cycloheteroalkyl or substituted cycloheteroalkyl ring;

R$^5$ is selected from the group consisting of hydrogen, R$^6$—, R$^6$C(O)— and R$^6$OC(O)—;

R$^6$ is selected from the group consisting of alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

R$^7$ is selected from the group consisting of hydrogen, alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

R$^8$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

each R$^9$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when R$^8$ and R$^9$ are attached to adjacent atoms then R$^8$ and R$^9$ together with the atoms to which they are bonded form a cycloheteroalkyl or substituted cycloheteroalkyl ring;

R$^{11}$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

with the provisos that:
when R$^1$ is [R$^5$NH(CHR$^4$)$_p$C(O)]— then R$^2$ is —OR$^7$;
and when R$^2$ is —[NR$^8$(CHR$^9$)$_q$C(O)OR$^7$] then R$^1$ is not [R$^5$NH(CHR$^4$)$_p$C(O)]—.

In one embodiment, a compound of Formula (I) is derived from α-amino acids (e.g., [H$_2$N(CHR$^4$)C(O)OH] and/or [HNR$^8$(CHR$^9$)C(O)OH]) including, but not limited to, the 20 genetically encoded amino acids and the non-coded amino acids such as, for Example, 2,3-diaminobutyric acid, 2,4-diaminobutyric acid, hydroxylysine, homoserine, homoarginine, homotyrosine, homocysteine, homophenylalanine, citrulline, sarcosine, orthinine, N-methylleucine, kynurenine, penicillamine, 4-aminophenylalanine, 3-(2- naphthyl)alanine, 3-(1-naphthyl)alanine, methionine sulfone, methionine sulfoxide, t-butylalanine, 4-hydroxyphenylglycine, aminoalanine, 1,2,3,4 tetrahydorisoquinoline-3-carboxylic acid, vinylalanine, propargylglycine, 1,2,4-triazolo-3-alanine, 4,4,4-trifluoro-threonine, thyronine, 6-hydroxytryptophan, 5-hydroxytryptophan, 3-hydroxykynurenine, 3-aminotyrosine, trifluoromethylalanine (2-(4-pyridyl)ethyl)cysteine, 3,4-dimethoxy-phenylalanine, 3-(2-thiazolyl)alanine, ibotenic acid, quisqualic acid, 3-trifluoromethylphenylalanine, 4-trifluoromethylphenylalanine, t-butylglycine, cyclopentylglycine, cyclohexylglycine, phenylglycine, cyclohexylalanine, thiohistidine, 3-methoxytyrosine, norleucine, norvaline, alloisoleucine, thioproline, dehydroproline, hydroxyproline, isonipectotic acid, homoproline, N-acetyl lysine, aminophenylbutyric acid, phenylalanines substituted at the ortho, meta or para position of the phenyl moiety with one or two of the following: a ($C_{1-4}$) alkyl, a ($C_{1-4}$) alkoxy, halogen or nitro groups or substituted with a methylenedioxy group, β-2- and 3-thienylalanine, β-2- and 3-furanylalanine, 2-, 3- and 4-pyridylalanine, β-(benzothienyl-2- and 3-yl)alanine, β-(1- and 2-naphthyl)alanine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine or 3-nitrotyrosine.

In one embodiment of a compound of Formula (I), n is 1 and $R^3$ is hydrogen, alkyl, substituted alkyl, aryl, substituted aryl, arylalkyl, cycloalkyl or heteroaryl. Preferably, $R^3$ is hydrogen, alkyl or substituted alkyl, more preferably, $R^3$ is hydrogen or $C_{1-4}$ alkyl, even more preferably, $R^3$ is hydrogen or methyl.

In another embodiment of a compound of Formula (I), n is 1 and $R^3$ is hydrogen, aryl or substituted aryl. Preferably, $R^3$ is hydrogen, phenyl or substituted phenyl.

In still another embodiment of a compound of Formula (I), n is 1 and $R^3$ is hydrogen, arylalkyl or substituted arylalkyl. Preferably, $R^3$ is hydrogen, benzyl or substituted benzyl.

In still another embodiment of a compound of Formula (I), $R^1$ is hydrogen or $[R^5NH(CHR^4)_pC(O)]—$, where p is 1. Preferably, $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, $R^4$ and $R^5$ together with the atoms to which they are bonded form a cycloheteroalkyl or substituted cycloheteroalkyl ring.

In still another embodiment of a compound of Formula (I), $R^1$ is $[R^5NH(CHR^4)_nC(O)]—$, p is 1, $R^5$ is hydrogen and $R^4$ is hydrogen, alkanyl or cycloalkanyl. Preferably, $R^4$ is hydrogen, methyl, isopropyl, isobutyl, sec-butyl, t-butyl, cyclopentyl or cyclohexyl.

In still another embodiment of a compound of Formula (I), $R^1$ is $[R^5NH(CHR^4)_pC(O)]—$, p is 1, $R^5$ is hydrogen, and $R^4$ is substituted alkanyl. Preferably, $R^4$ is $—CH_2OH$, $—CH(OH)CH_3$, $—CH_2CO_2H$, $—CH_2CH_2CO_2H$, $—CH_2CONH_2$, $—CH_2CH_2CONH_2$, $—CH_2CH_2SCH_3$, $—CH_2SH$, $—CH_2(CH_2)_3NH_2$ or $—CH_2CH_2CH_2NHC(NH)NH_2$.

In still another embodiment of a compound of Formula (I), $R^1$ is $[R^5NH(CHR^4)_pC(O)]—$, p is 1, $R^5$ is hydrogen, and $R^4$ is aryl, arylalkanyl, substituted arylalkanyl or heteroarylalkanyl. Preferably, $R^4$ is phenyl, benzyl, 4-hydroxybenzyl, 4-imidazolylmethyl or 3-indolylmethyl.

In still another embodiment of a compound of Formula (I), $R^1$ is $[R^5NH(CHR^4)_pC(O)]—$, p is 1 and $R^4$ and $R^5$ together with the atoms to which they are bonded form a cycloheteroalkyl or substituted cycloheteroalkyl ring. Preferably $R^4$ and $R^5$ together with the atoms to which they are bonded form an azetidine, pyrrolidine or piperidine ring.

In still another embodiment of a compound of Formula (I), $R^1$ is $[R^5NH(CHR^4)_pC(O)]—$, p is 1, $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl, $R^5$ is $R^6—$, $R^6C(O)—$ or $R^6OC(O)—$ and $R^6$ is alkyl, substituted alkyl, aryl, substituted aryl, arylalkyl, substituted arylalkyl, cycloalkyl, substituted cycloalkyl, cyclohetroalkyl, heteroaryl, substituted heteroaryl or heteroarylalkyl. Preferably, $R^6$ is $C_{1-4}$ alkyl, phenyl, substituted phenyl, benzyl or substituted benzyl.

In still another embodiment of a compound of Formula (I), $R^1$ is hydrogen or $[R^5NH(CHR^4)_pC(O)]—$, where p is 2. Preferably, $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, when $R^4$ and $R^5$ are attached to adjacent atoms then $R^4$ and $R^5$ together with the atoms to which they are bonded form a cycloheteroalkyl or substituted cycloheteroalkyl ring.

In still another embodiment of a compound of Formula (I), $R^1$ is $[R^5NH(CHR^4)_pC(O)]—$, p is 2 and $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl. Preferably, $R^4$ is hydrogen, $C_{1-4}$ alkyl, cyclopentyl, cyclohexyl, phenyl, substituted phenyl, benzyl or substituted benzyl.

In still another embodiment of a compound of Formula (I), $R^1$ is $[R^5NH(CHR^4)_pC(O)]—$, p is 2, $R^5$ is hydrogen and $R^4$ is hydrogen, $C_{1-4}$ alkyl, cyclopentyl, cyclohexyl, phenyl, substituted phenyl, benzyl or substituted benzyl.

In still another embodiment of a compound of Formula (I), $R^2$ is $—OR^7$ and $R^7$ is hydrogen, alkyl, aryl, substituted aryl, arylalkyl or substituted arylalkyl. Preferably, $R^7$ is hydrogen, $C^{14}$ alkyl, phenyl, substituted phenyl, benzyl or substituted benzyl.

In still another embodiment of a compound of Formula (I), $R^2$ is $—[NR^8(CHR^9)_qC(O)OR^7]$, q is 1, $R^7$ is hydrogen, alkyl, aryl, substituted aryl, arylalkyl or substituted arylalkyl. Preferably, $R^7$ is hydrogen, $C_{1-4}$ alkyl, phenyl, substituted phenyl, benzyl or substituted benzyl.

In still another embodiment of a compound of Formula (I), $R^2$ is $—[NR^8(CHR^9)_qC(O)OR^7]$, q is 1, $R^8$ is hydrogen and $R^9$ is hydrogen, alkyl, substituted alkanyl, aryl, substituted aryl, arylalkyl, substituted arylalkanyl, cycloalkanyl, heteroarylalkanyl or substituted heteroarylalkanyl. Preferably, $R^7$ hydrogen, alkyl, aryl, substituted aryl, arylalkyl or substituted arylalkyl, more preferably, $R^7$ is hydrogen, $C_{1-4}$ alkyl, phenyl, substituted phenyl, benzyl or substituted benzyl.

In still another embodiment of a compound of Formula (I), $R^2$ is $—[NR^8(CHR^9)_qC(O)OR^7]$, q is 1, $R^7$ is hydrogen, alkyl, aryl, substituted aryl, arylalkyl or substituted arylalkyl, $R^8$ is hydrogen and $R^9$ is hydrogen, alkanyl or cycloalkanyl. Preferably, $R^9$ is hydrogen, methyl, isopropyl, isobutyl, sec-butyl, t-butyl, cyclopentyl or cyclohexyl. Preferably, $R^7$ is hydrogen, $C_{1-4}$ alkyl, phenyl, substituted phenyl, benzyl or substituted benzyl.

In still another embodiment of a compound of Formula (I), $R^2$ is $—[NR^8(CHR^9)_qC(O)OR^7]$, q is 1, $R^7$ is hydrogen, alkyl, aryl, substituted aryl, arylalkyl or substituted arylalkyl, $R^8$ is hydrogen and $R^9$ is substituted alkanyl. Preferably, $R^9$ is $—CH_2OH$, $—CH(OH)CH_3$, $—CH_2CO_2H$, $—CH_2CH_2CO_2H$, $—CH_2CONH_2$, $—CH_2CH_2CONH_2$, $—CH_2CH_2SCH_3$, $—CH_2SH$, $—CH_2(CH_2)_3NH_2$ or —CH₂CH₂CH₂NHC(NH)NH₂. Preferably, $R^7$ is hydrogen, $C_{1-4}$ alkyl, phenyl, substituted phenyl, benzyl or substituted benzyl.

In still another embodiment of a compound of Formula (I), $R^2$ is —[NR⁸(CHR⁹)$_q$C(O)OR⁷], q is 1, $R^7$ is hydrogen, alkyl, aryl, substituted aryl, arylalkyl or substituted arylalkyl, $R^8$ is hydrogen and $R^9$ is aryl, arylalkanyl, substituted arylalkanyl or heteroarylalkanyl. Preferably, $R^9$ is phenyl, benzyl, 4-hydroxybenzyl, 4-imidazolylmethyl or 3-indolylmethyl. Preferably $R^7$ is hydrogen, $C_{1-4}$ alkyl, phenyl, substituted phenyl, benzyl or substituted benzyl.

In still another embodiment of a compound of Formula (I), $R^2$ is —[NR⁸(CHR⁹)$_q$C(O)OR⁷], q is 1, $R^7$ is hydrogen, alkyl, aryl, substituted aryl, arylalkyl or substituted arylalkyl and $R^8$ and $R^9$ together with the atoms to which they are bonded form a cycloheteroalkyl or substituted cycloheteroalkyl ring. Preferably $R^8$ and $R^9$ together with the atoms to which they are bonded form an azetidine, pyrrolidine or piperidine ring. Preferably, $R^7$ is hydrogen, $C_{1-4}$ alkyl, phenyl, substituted phenyl, benzyl or substituted benzyl.

In still another embodiment of a compound of Formula (1), $R^2$ is —[NR⁸(CHR⁹)$_q$C(O)OR⁷], q is 2, $R^7$ is hydrogen, alkyl, aryl, substituted aryl, arylalkyl or substituted arylalkyl and $R^9$ is hydrogen, alkanyl, substituted alkanyl, aryl, substituted aryl, arylalkanyl, substituted arylalkanyl, cycloalkanyl, heteroarylalkanyl or substituted heteroarylalkanyl. Preferably, $R^7$ is hydrogen, $C_{1-4}$ alkyl, phenyl, substituted phenyl, benzyl or substituted benzyl. Preferably, $R^8$ is hydrogen and $R^9$ is hydrogen, $C_{1-4}$ alkyl, cyclopentyl, cyclohexyl, phenyl, substituted phenyl, benzyl or substituted benzyl.

In still another embodiment of a compound of Formula (I), m is 1, n is 0, X is a bond, $R^1$ is [R⁵NH(CHR⁴)$_p$C(O)]—, p is 1, $R^5$ is hydrogen, $R^2$ is —OR⁷, $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl and $R^7$ is hydrogen, alkyl, aryl, substituted aryl, arylalkyl or substituted arylalkyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 1, n is 0, X is a bond, $R^1$ is [R⁵NH(CHR⁴)$_p$C(O)]—, p is 1, $R^5$ is hydrogen and $R^2$ is —OH to provide a compound of Formula (III):

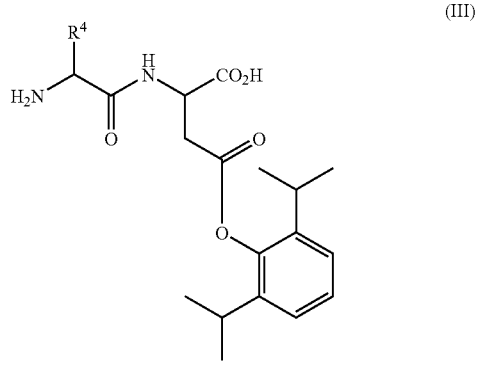

(III)

where $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl.

In one embodiment of a compound of Formula (III), $R^4$ is hydrogen, alkanyl, or cycloalkanyl. Preferably, $R^4$ is hydrogen, methyl, isopropyl, isobutyl, sec-butyl, t-butyl, cyclopentyl or cyclohexyl.

In another embodiment of a compound of Formula (III), $R^4$ is substituted alkanyl. Preferably, $R^4$ is —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂ or —CH₂CH₂CH₂NHC(NH)NH₂.

In still another embodiment of a compound of Formula (III), $R^4$ is aryl, arylalkanyl, substituted arylalkanyl or heteroarylalkanyl. Preferably, $R^4$ is phenyl, benzyl, 4-hydroxybenzyl, 4-imidazolylmethyl or 3-indolylmethyl.

In still another embodiment of a compound of Formula (III), the α-carbon of the N-terminal amino acid residue is of the L-configuration. In still another embodiment of a compound of Formula (III), the α-carbon of the N-terminal amino acid residue is of the D-configuration. In still another embodiment of a compound of Formula (III), the α-carbon of the C-terminal amino acid residue is of the L-configuration. In still another embodiment of a compound of Formula (III), the α-carbon of the C-terminal amino acid residue is of the D-configuration. In still another embodiment of a compound of Formula (III), the α-carbons of both the N- and C-terminal amino acid residues are of the L-configuration.

In still another embodiment of a compound of Formula (I), m is 2, n is 0, X is a bond, $R^1$ is [R⁵NH(CHR⁴)$_p$C(O)]—, p is 1, $R^5$ is hydrogen, $R^2$ is —OR⁷, $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl and $R^7$ is hydrogen, alkyl, aryl, substituted aryl, arylalkyl or substituted arylalkyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 2, n is 0, X is a bond, $R^1$ is [R⁵NH(CHR⁴)$_p$C(O)]—, p is 1, $R^5$ is hydrogen and $R^2$ is —OH to provide a compound of Formula (IV):

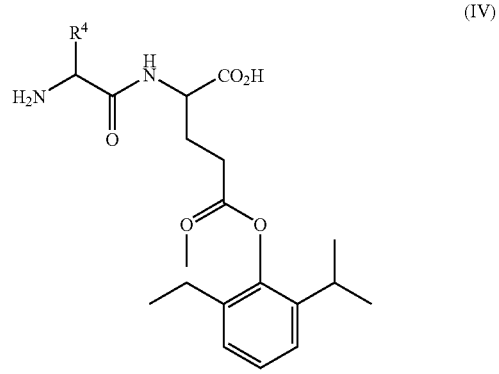

(IV)

where $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl.

In one embodiment of a compound of Formula (IV), $R^4$ is hydrogen, alkanyl or cycloalkanyl. Preferably, $R^4$ is hydrogen, methyl, isopropyl, isobutyl, sec-butyl, t-butyl, cyclopentyl or cyclohexyl.

In another embodiment of a compound of Formula (IV), $R^4$ is substituted alkanyl. Preferably, $R^4$ is —CH₂OH, —CH (OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (IV), R$^4$ is aryl, arylalkanyl, substituted arylalkanyl or heteroarylalkanyl. Preferably, R$^4$ is phenyl, benzyl, 4-hydroxybenzyl, 4-imidazolylmethyl or 3-indolylmethyl.

In still another embodiment of a compound of Formula (IV), the α-carbon of the N-terminal amino acid residue is of the L-configuration. In still another embodiment of a compound of Formula (IV), the α-carbon of the N-terminal amino acid residue is of the D-configuration. In still another embodiment of a compound of Formula (IV), the α-carbon of the C-terminal amino acid residue is of the L-configuration. In still another embodiment of a compound of Formula (IV), the α-carbon of the C-terminal amino acid residue is of the D-configuration. In still another embodiment of a compound of Formula (IV), the α-carbons of both the N- and C-terminal amino acid residues are of the L-configuration.

In still another embodiment of a compound of Formula (I), m is 1, n is 0, X is —O—, R$^1$ is [R$^5$NH(CHR$^4$)$_p$C(O)]—, p is 1, R$^5$ is hydrogen, R$^2$ is —OR$^7$, R$^4$ is hydrogen alkanyl, substituted alkanyl, aryl, substituted aryl, arylalkanyl, substituted arylalkanyl, cycloalkanyl, heteroarylalkanyl or substituted heteroarylalkanyl and R$^7$ is hydrogen, alkyl, aryl, substituted aryl, arylalkyl or substituted arylalkyl. Preferably, R$^7$ is hydrogen, C$_{1-4}$ alkyl, phenyl, substituted phenyl, benzyl or substituted benzyl, more preferably, R$^7$ is hydrogen.

In still another embodiment of a compound of Formula (I), m is 1, n is 0, X is —O—, R$^1$ is [R$^5$NH(CHR$^4$)$_p$C(O)]—, p is 1, R$^5$ is hydrogen and R$^2$ is —OH to provide a compound of Formula (V):

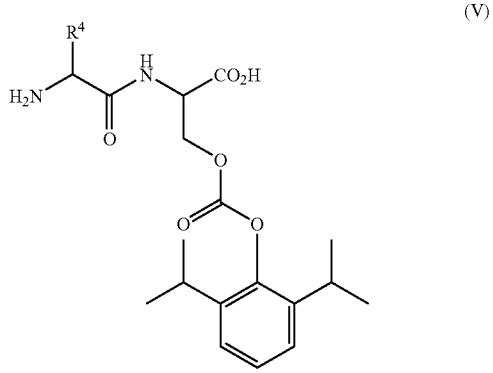

where R$^4$ is hydrogen, alkanyl, substituted alkanyl, aryl, substituted aryl, arylalkanyl, substituted arylalkanyl, cycloalkanyl, heteroarylalkanyl or substituted heteroarylalkanyl.

In one embodiment of a compound of Formula (V), R$^4$ is hydrogen, alkanyl or cycloalkanyl. Preferably, R$^4$ is hydrogen, methyl, isopropyl, isobutyl, sec-butyl, t-butyl, cyclopentyl or cyclohexyl.

In another embodiment of a compound of Formula (V), R$^4$ is substituted alkanyl. Preferably, R$^4$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (V), R$^4$ is aryl, arylalkanyl, substituted arylalkanyl or heteroarylalkanyl. Preferably, R$^4$ is phenyl, benzyl, 4-hydroxybenzyl, 4-imidazolylmethyl or 3-indolylmethyl.

In still another embodiment of a compound of Formula (V), the α-carbon of the N-terminal amino acid residue is of the L-configuration. In still another embodiment of a compound of Formula (V), the α-carbon of the N-terminal amino acid residue is of the D-configuration. In still another embodiment of a compound of Formula (V), the α-carbon of the C-terminal amino acid residue is of the L-configuration. In still another embodiment of a compound of Formula (V), the α-carbon of the C-terminal amino acid residue is of the D-configuration. In still another embodiment of a compound of Formula (V), the α-carbons of both the N- and C-terminal amino acid residues are of the L-configuration.

In still another embodiment of a compound of Formula (I), m is 1, n is 0, X is —S—, R$^1$ is [R$^5$NH(CHR$^4$)$_p$C(O)]—, p is 1, R$^5$ is hydrogen, R$^2$ is —OR$^7$, R$^4$ is hydrogen alkanyl, substituted alkanyl, aryl, substituted aryl, arylalkanyl, substituted arylalkanyl, cycloalkanyl, heteroarylalkanyl or substituted heteroarylalkanyl and R$^7$ is hydrogen, alkyl, aryl, substituted aryl, arylalkyl or substituted arylalkyl. Preferably, R$^7$ is hydrogen, C$_{1-4}$ alkyl, phenyl, substituted phenyl, benzyl or substituted benzyl, more preferably, R$^7$ is hydrogen.

In still another embodiment of a compound of Formula (I), m is 1, n is 0, X is —S—, R$^1$ is [R$^5$NH(CHR$^4$)$_p$C(O)]—, p is 1, R$^5$ is hydrogen and R$^2$ is —OH to provide a compound of Formula (VI):

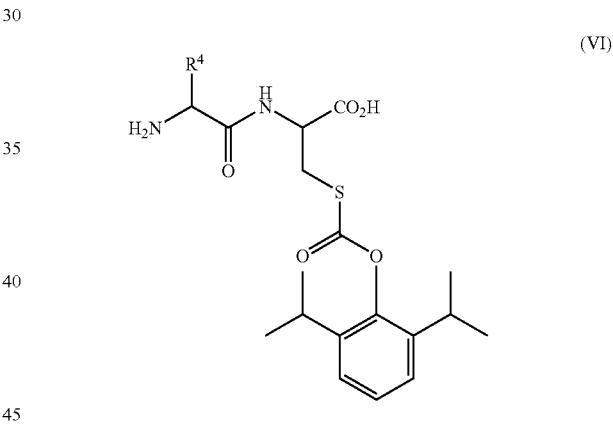

where R$^4$ is hydrogen, alkanyl, substituted alkanyl, aryl, substituted aryl, arylalkanyl, substituted arylalkanyl, cycloalkanyl, heteroarylalkanyl or substituted heteroarylalkanyl.

In one embodiment of a compound of Formula (VI), R$^4$ is hydrogen, alkanyl, or cycloalkanyl. Preferably, R$^4$ is hydrogen, methyl, isopropyl, isobutyl, sec-butyl, t-butyl, cyclopentyl or cyclohexyl.

In another embodiment of a compound of Formula (VI), R$^4$ is substituted alkanyl. Preferably, R$^4$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (VI), R$^4$ is aryl, arylalkanyl, substituted arylalkanyl or heteroarylalkanyl. Preferably, R$^4$ is phenyl, benzyl, 4-hydroxybenzyl, 4-imidazolylmethyl or 3-indolylmethyl.

In still another embodiment of a compound of Formula (VI), the α-carbon of the N-terminal amino acid residue is of the L-configuration. In still another embodiment of a compound of Formula (VI), the α-carbon of the N-terminal amino acid residue is of the D-configuration. In still another embodiment of a compound of Formula (VI), the α-carbon of the C-terminal amino acid residue is of the L-configuration. In still another embodiment of a compound of Formula (VI), the α-carbon of the C-terminal amino acid residue is of the D-configuration. In still another embodiment of a compound of Formula (VI), the α-carbons of both the N- and C-terminal amino acid residues are of the L-configuration.

In still another embodiment of a compound of Formula (I), m is 1, n is 1, X is a bond, $R^1$ is $[R^5NH(CHR^4)_pC(O)]—$, p is 1, $R^5$ is hydrogen, $R^2$ is $—OR^7$, $R^3$ is hydrogen, alkyl, substituted alkyl, aryl, substituted aryl, arylalkyl, cycloalkyl or heteroaryl, $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl and $R^7$ is hydrogen, alkyl, aryl, substituted aryl, arylalkyl or substituted arylalkyl. Preferably, $R^3$ is hydrogen, $C_{1-4}$ alkyl, phenyl, substituted phenyl, benzyl or substituted benzyl. More preferably, $R^3$ is hydrogen or methyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 1, n is 1, X is a bond, $R^1$ is $[R^5NH(CHR^4)_pC(O)]—$, p is 1, $R^5$ is hydrogen and $R^2$ is —OH to provide a compound of Formula (VII):

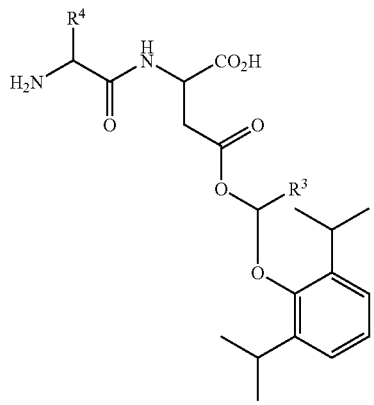

(VII)

where $R^3$ is hydrogen or methyl and $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl.

In one embodiment of a compound of Formula (VII), $R^4$ is hydrogen, alkanyl, or cycloalkanyl. Preferably, $R^4$ is hydrogen, methyl, isopropyl, isobutyl, sec-butyl, t-butyl, cyclopentyl or cyclohexyl.

In another embodiment of a compound of Formula (VII), $R^4$ is substituted alkanyl. Preferably, $R^4$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (VII), $R^4$ is aryl, arylalkanyl, substituted arylalkanyl or heteroarylalkanyl. Preferably, $R^4$ is phenyl, benzyl, 4-hydroxybenzyl, 4-imidazolylmethyl or 3-indolylmethyl.

In still another embodiment of a compound of Formula (VII), the α-carbon of the N-terminal amino acid residue is of the L-configuration. In still another embodiment of a compound of Formula (VII), the α-carbon of the N-terminal amino acid residue is of the D-configuration. In still another embodiment of a compound of Formula (VII), the α-carbon of the C-terminal amino acid residue is of the L-configuration. In still another embodiment of a compound of Formula (VII), the α-carbon of the C-terminal amino acid residue is of the D-configuration. In still another embodiment of a compound of Formula (VII), the α-carbons of both the N- and C-terminal amino acid residues are of the L-configuration. In still another embodiment of a compound of Formula (VII), $R^3$ is hydrogen.

In still another embodiment of a compound of Formula (I), m is 2, n is 1, X is a bond, $R^1$ is $[R^5NH(CHR^4)_pC(O)]—$, p is 1, $R^5$ is hydrogen, $R^2$ is $—OR^7$, $R^3$ is hydrogen, alkyl, substituted alkyl, aryl, substituted aryl, arylalkyl, cycloalkyl or heteroaryl, $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl and $R^7$ is hydrogen, alkyl, aryl, substituted aryl, arylalkyl or substituted arylalkyl. Preferably, $R^3$ is hydrogen, $C_{1-4}$ alkyl, phenyl, substituted phenyl, benzyl or substituted benzyl, more preferably, $R^3$ is hydrogen or methyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 2, n is 1, X is a bond, $R^1$ is $[R^5NH(CHR^4)_pC(O)]—$, p is 1, $R^5$ is hydrogen and $R^2$ is —OH to provide a compound of Formula (VIII):

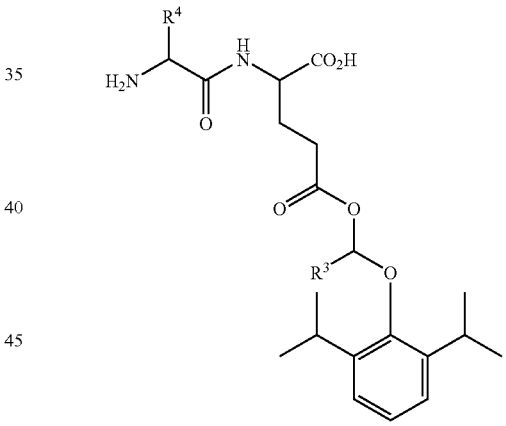

(VIII)

where $R^3$ is hydrogen or methyl and $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl.

In one embodiment of a compound of Formula (VIII), $R^4$ is hydrogen, alkanyl or cycloalkanyl. Preferably, $R^4$ is hydrogen, methyl, isopropyl, isobutyl, sec-butyl, t-butyl, cyclopentyl or cyclohexyl.

In another embodiment of a compound of Formula (VIII), $R^4$ is substituted alkanyl. Preferably, $R^4$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (VIII), $R^4$ is aryl, arylalkanyl, substituted arylalkanyl or heteroarylalkanyl. Preferably, $R^4$ is phenyl, benzyl, 4-hydroxybenzyl, 4-imidazolylmethyl or 3-indolylmethyl.

In still another embodiment of a compound of Formula (VIII), the α-carbon of the N-terminal amino acid residue is of the L-configuration. In still another embodiment of a compound of Formula (VIII), the α-carbon of the N-terminal amino acid residue is of the D-configuration. In still another embodiment of a compound of Formula (VIII), the α-carbon of the C-terminal amino acid residue is of the L-configuration. In still another embodiment of a compound of Formula (VIII), the α-carbon of the C-terminal amino acid residue is of the D-configuration. In still another embodiment of a compound of Formula (VIII), the α-carbons of both the N- and C-terminal amino acid residues are of the L-configuration. In still another embodiment of a compound of Formula (VIII), $R^3$ is hydrogen. In still another embodiment of a compound of Formula (VIII), $R^3$ is hydrogen.

In still another embodiment of a compound of Formula (I), m is 1, n is 0, X is a bond, $R^1$ is selected from the group consisting of hydrogen, $R^6$—, $R^6C(O)$— and $R^6OC(O)$—, $R^2$ is —[NR$^8$(CHR$^9$)$_q$C(O)OR$^7$], q is 1, $R^6$ is alkyl, aryl, substituted aryl, arylalkyl or substituted arylalkyl, $R^7$ is alkyl, aryl, substituted aryl, arylalkyl or substituted arylalkyl, $R^8$ is hydrogen or alkyl, $R^9$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, $R^8$ and $R^9$ together with the atoms to which they are bonded form a cycloheteroalkyl or substituted cycloheteroalkyl ring. Preferably, $R^1$ is hydrogen. Preferably, $R^6$ is $C_{1-4}$ alkyl, phenyl, substituted phenyl, benzyl or substituted benzyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 1, n is 0, X is a bond, $R^1$ is hydrogen, $R^2$ is —[NR$^8$(CHR$^9$)$_q$C(O)OR$^7$], q is 1, $R^7$ is hydrogen, alkyl, aryl, substituted aryl, arylalkyl or substituted arylalkyl, $R^8$ is hydrogen or alkyl, $R^9$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, $R^8$ and $R^9$ together with the atoms to which they are bonded form a cycloheteroalkyl or substituted cycloheteroalkyl ring. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 1, n is 0, X is a bond, $R^1$ is hydrogen, $R^2$ is —[NR$^8$(CHR$^9$)$_q$C(O)OR$^7$], q is 1 and $R^7$ is hydrogen to provide a compound of Formula (IX):

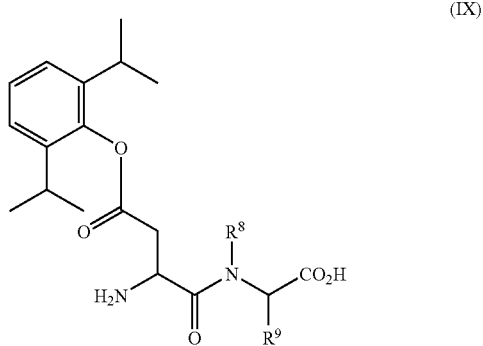

(IX)

where $R^8$ is hydrogen or methyl and $R^9$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, $R^8$ and $R^9$ together with the atoms to which they are bonded form a cycloheteroalkyl or substituted cycloheteroalkyl ring.

In one embodiment of a compound of Formula (IX), $R^9$ is hydrogen, alkanyl or cycloalkanyl. Preferably, $R^9$ is hydrogen, methyl, isopropyl, isobutyl, sec-butyl, t-butyl, cyclopentyl or cyclohexyl.

In another embodiment of a compound of Formula (IX), $R^9$ is substituted alkanyl. Preferably, $R^9$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (IX), $R^9$ is aryl, arylalkanyl, substituted arylalkanyl or heteroarylalkanyl. Preferably, $R^9$ is phenyl, benzyl, 4-hydroxybenzyl, 4-imidazolylmethyl or 3-indolylmethyl.

In still another embodiment of a compound of Formula (IX), $R^8$ and $R^9$ together with the atoms to which they are bonded form a cycloheteroalkyl or substituted cycloheteroalkyl ring. Preferably, $R^8$ and $R^9$ together with the atoms to which they are bonded form an azetidine, pyrrolidine or piperidine ring.

In still another embodiment of a compound of Formula (IX), the α-carbon of the N-terminal amino acid residue is of the L-configuration. In still another embodiment of a compound of Formula (IX), the α-carbon of the N-terminal amino acid residue is of the D-configuration. In still another embodiment of a compound of Formula (IX), the α-carbon of the C-terminal amino acid residue is of the L-configuration. In still another embodiment of a compound of Formula (IX), the α-carbon of the C-terminal amino acid residue is of the D-configuration. In still another embodiment of a compound of Formula (IX), the α-carbons of both the N- and C-terminal amino acid residues are of the L-configuration. In still another embodiment of a compound of Formula (IX), $R^8$ is hydrogen.

In still another embodiment of a compound of Formula (I), m is 2, n is 0, X is a bond, $R^1$ is hydrogen, $R^2$ is —[NR$^8$(CHR$^9$)$_q$C(O)OR$^7$], q is 1, $R^7$ is hydrogen, alkyl, aryl, substituted aryl, arylalkyl or substituted arylalkyl, $R^8$ is hydrogen or alkyl, $R^9$ is hydrogen, alkanyl, substituted alkanyl, aryl, substituted aryl, arylalkanyl, substituted arylalkanyl, cycloalkanyl, heteroarylalkanyl or substituted heteroarylalkanyl or optionally, $R^8$ and $R^9$ together with the atoms to which they are bonded form a cycloheteroalkyl or substituted cycloheteroalkyl ring. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 2, n is 0, X is a bond, $R^1$ is hydrogen, $R^2$ is —[NR$^8$(CHR$^9$)$_q$C(O)OR$^7$], q is 1 and $R^7$ is hydrogen to provide a compound of Formula (X):

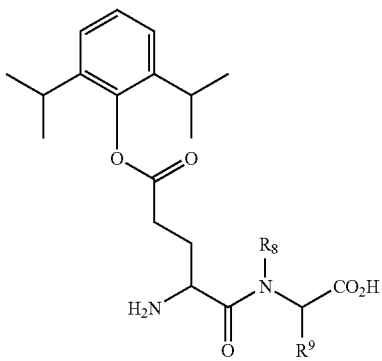

R[8] is hydrogen or methyl and R[9] is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, R[8] and R[9] together with the atoms to which they are bonded form a cycloheteroalkyl or substituted cycloheteroalkyl ring.

In one embodiment of a compound of Formula (X), R[9] is hydrogen, alkanyl or cycloalkanyl. Preferably, R[9] is hydrogen, methyl, isopropyl, isobutyl, sec-butyl, t-butyl, cyclopentyl or cyclohexyl.

In another embodiment of a compound of Formula (X), R[9] is substituted alkanyl. Preferably, R[9] is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (X), R[19] is aryl, arylalkanyl, substituted arylalkanyl or heteroarylalkanyl. Preferably, R[9] is phenyl, benzyl, 4-hydroxybenzyl, 4-imidazolylmethyl or 3-indolylmethyl.

In still another embodiment of a compound of Formula (X), R[8] and R[9] together with the atoms to which they are bonded form a cycloheteroalkyl or substituted cycloheteroalkyl ring. Preferably, R[8] and R[9] together with the atoms to which they are bonded form an azetidine, pyrrolidine or piperidine ring.

In still another embodiment of a compound of Formula (X), the α-carbon of the N-terminal amino acid residue is of the L-configuration. In still another embodiment of a compound of Formula (X), the α-carbon of the N-terminal amino acid residue is of the D-configuration. In still another embodiment of a compound of Formula (X), the α-carbon of the C-terminal amino acid residue is of the L-configuration. In still another embodiment of a compound of Formula (X), the α-carbon of the C-terminal amino acid residue is of the D-configuration. In still another embodiment of a compound of Formula (X), the α-carbons of both the N- and C-terminal amino acid residues are of the L-configuration. In still another embodiment of a compound of Formula (X), R[3] is hydrogen. In still another embodiment of a compound of Formula (X), R[8] is hydrogen.

In still another embodiment of a compound of Formula (I), m is 1, n is 1, X is a bond, R[1] is hydrogen, R[2] is —[NR[8](CHR[9])$_q$C(O)OR[7]], q is 1, R[3] is hydrogen, alkyl, substituted alkyl, aryl, substituted aryl, arylalkyl, cycloalkyl or heteroaryl, R[7] is hydrogen, alkyl, substituted alkyl, aryl, substituted aryl, arylalkyl, substituted arylalkyl, cycloalkyl, substituted cycloalkyl, cycloheteroalkyl, heteroaryl, substituted heteroaryl or heteroarylalkyl, R[8] is hydrogen or methyl, R[9] is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, R[8] and R[9] together with the atoms to which they are bonded form a cycloheteroalkyl or substituted cycloheteroalkyl ring. Preferably, R[3] is hydrogen, C$_{1-4}$ alkyl, phenyl, substituted phenyl, benzyl or substituted benzyl. More preferably, R[3] is hydrogen or methyl. Preferably R[7] is hydrogen, C$_{1-4}$ alkyl, phenyl, substituted phenyl, benzyl or substituted benzyl. More preferably, R[7] is hydrogen.

In still another embodiment of a compound of Formula (I), m is 1, n is 1, X is a bond, R[1] is hydrogen, R[2] is —[NR[8](CHR[9])$_q$C(O)OR[7]], q is 1 and R[7] is hydrogen to provide a compound of Formula (XI):

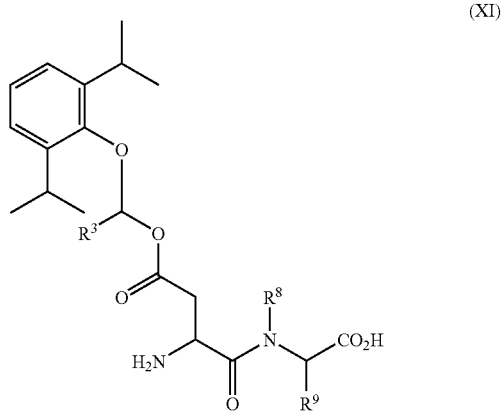

where R[3] is hydrogen or methyl, R[8] is hydrogen or methyl and R[9] is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, R[8] and R[9] together with the atoms to which they are bonded, form a cycloheteroalkyl or substituted cycloheteroalkyl ring.

In one embodiment of a compound of Formula (XI), R[9] is hydrogen, alkanyl or cycloalkanyl. Preferably, R[9] is hydrogen, methyl, isopropyl, isobutyl, sec-butyl, t-butyl, cyclopentyl or cyclohexyl.

In another embodiment of a compound of Formula (XI), R[9] is substituted alkanyl. Preferably, R[9] is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (XI), R[9] is aryl, arylalkanyl, substituted arylalkanyl or heteroarylalkanyl. Preferably, R[9] is phenyl, benzyl, 4-hydroxybenzyl, 4-imidazolylmethyl or 3-indolylmethyl.

In still another embodiment of a compound of Formula (XI), R[8] and R[9] together with the atoms to which they are bonded form a cycloheteroalkyl or substituted cycloheteroalkyl ring. Preferably, R[5] and R[9] together with the atoms to which they are bonded form an azetidine, pyrrolidine or piperidine ring.

In still another embodiment of a compound of Formula (XI), the α-carbon of the N-terminal amino acid residue is of the L-configuration. In still another embodiment of a compound of Formula (XI), the α-carbon of the N-terminal amino acid residue is of the D-configuration. In still another embodiment of a compound of Formula (XI), the α-carbon of the C-terminal amino acid residue is of the L-configuration. In still another embodiment of a compound of Formula (XI), the α-carbon of the C-terminal amino acid residue is of the D-configuration. In still another embodiment of a compound of Formula (XI), the α-carbons of both the N- and C-terminal amino acid residues are of the L-configuration. In still another embodiment of a compound of Formula (XI), $R^3$ is hydrogen. In still another embodiment of a compound of Formula (XI), $R^8$ is hydrogen.

In still another embodiment of a compound of Formula (I), m is 1, n is 0, X is a bond, $R^1$ is hydrogen, $R^2$ is —$OR^7$ and $R^7$ is hydrogen, alkyl, aryl, substituted aryl, arylalkyl or substituted arylalkyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 1, n is 0, X is a bond, $R^1$ is hydrogen, $R^2$ is —$OR^7$ and $R^7$ is hydrogen to provide a compound of Formula (XII):

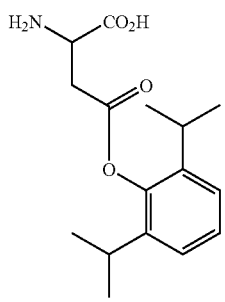

In one embodiment of a compound of Formula (XII), the α-carbon of the amino acid residue is of the L-configuration. In another embodiment of a compound of Formula (XII), the α-carbon of the amino acid residue is of the D-configuration.

In still another embodiment of a compound of Formula (I), m is 2, n is 0, X is a bond, $R^1$ is hydrogen, $R^2$ is —$OR^7$ and $R^7$ is hydrogen, alkyl, aryl, substituted aryl, arylalkyl or substituted arylalkyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 2, n is 0, X is a bond, $R^1$ is hydrogen, $R^2$ is —$OR^7$ and $R^7$ is hydrogen to provide a compound of Formula (XIII):

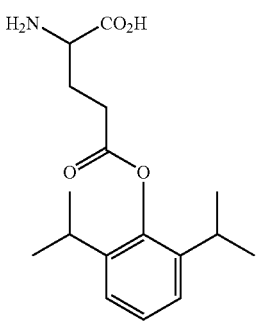

In one embodiment of a compound of Formula (XIII), the α-carbon of the amino acid residue is of the L-configuration. In another embodiment of a compound of Formula (XIII), the α-carbon of the amino acid residue is of the D-configuration.

In still another embodiment of a compound of Formula (I), m is 1, n is 1, X is a bond, $R^1$ is hydrogen, $R^2$ is —$OR^7$, $R^3$ is hydrogen, alkyl, substituted alkyl, aryl, substituted aryl, arylalkyl, cycloalkyl or heteroaryl and $R^7$ is hydrogen, alkyl, aryl, substituted aryl, arylalkyl or substituted arylalkyl. Preferably, $R^3$ is hydrogen, $C_{1-4}$ alkyl, phenyl, substituted phenyl, benzyl or substituted benzyl, more preferably, $R^3$ is hydrogen or methyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 1, n is 1, X is a bond, $R^1$ is hydrogen, $R^2$ is —$OR^7$ and $R^7$ is hydrogen to provide a compound of Formula (XIV):

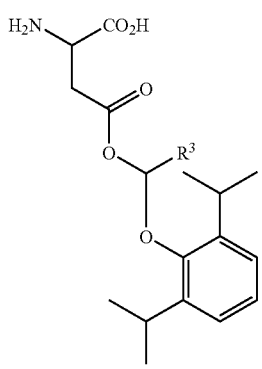

wherein $R^3$ is hydrogen or methyl.

In one embodiment of a compound of Formula (XIV), the α-carbon of the amino acid residue is of the L-configuration. In another embodiment of a compound of Formula (XIV), the α-carbon of the amino acid residue is of the D-configuration.

In still another embodiment of a compound of Formula (I), m is 2, n is 1, X is a bond, $R^1$ is hydrogen, $R^2$ is —$OR^7$, $R^3$ is hydrogen, alkyl, substituted alkyl, aryl, substituted aryl, arylalkyl, cycloalkyl or heteroaryl and $R^7$ is hydrogen, alkyl, aryl, substituted aryl, arylalkyl or substituted arylalkyl. Preferably, $R^3$ is hydrogen, $C_{1-4}$ alkyl, phenyl, substituted phenyl, benzyl or substituted benzyl, more preferably, $R^3$ is hydrogen or methyl. Preferably, $R^7$ is hydrogen, $C_{1-4}$ alkyl, phenyl, substituted phenyl, benzyl or substituted benzyl, more preferably, $R^7$ is hydrogen.

In still another embodiment of a compound of Formula (I), m is 2, n is 1, X is a bond, $R^1$ is hydrogen, $R^2$ is —$OR^7$ and $R^7$ is hydrogen to provide a compound of Formula (XV):

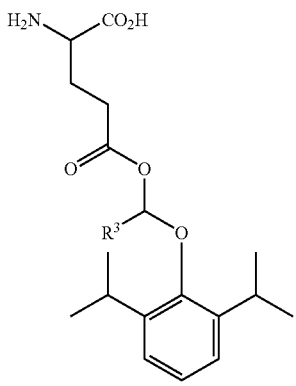

(XV)

wherein R³ is hydrogen or methyl.

In one embodiment of a compound of Formula (XIV), the α-carbon of the amino acid residue is of the L-configuration. In another embodiment of a compound of Formula (XIV), the α-carbon of the amino acid residue is of the D-configuration.

Another class of propofol prodrugs include compounds of structural Formula (II):

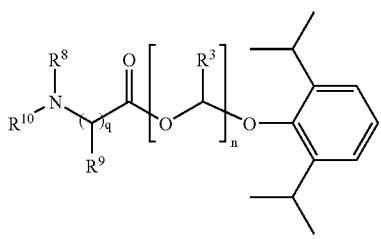

(II)

or a pharmaceutically acceptable salt, hydrate, solvate or N-oxide thereof, wherein:

$R^{10}$ is hydrogen or $[R^5NH(CHR^4)_pC(O)]—$;

n is 0 or 1;

p and q are independently 1 or 2;

$R^3$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

each $R^4$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^4$ and $R^5$ are attached to adjacent atoms then $R^4$ and $R^5$ together with the atoms to which they are bonded form a cycloheteroalkyl or substituted cycloheteroalkyl ring;

$R^5$ is selected from the group consisting of hydrogen, $R^6—$, $R^6C(O)—$ and $R^6OC(O)—$;

$R^6$ is selected from the group consisting of alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

$R^8$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

each $R^9$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^8$ and $R^9$ are attached to adjacent atoms then $R^8$ and $R^9$ together with the atoms to which they are bonded form a cycloheteroalkyl or substituted cycloheteroalkyl ring;

with the proviso that when $R^{10}$ is hydrogen then n is 1.

In one embodiment, a compound of Formula (II) is derived from α-amino acids (e.g., $[H_2N(CHR^4)C(O)OH]$ and/or $[HNR^8(CHR^9)C(O)OH]$) including, but not limited to, the 20 genetically encoded amino acids and the non-coded amino acids 2,3-diaminobutyric acid, 2,4-diaminobutyric acid, hydroxylysine, homoserine, homoarginine, homotyrosine, homocysteine, homophenylalanine, citrulline, sarcosine, orthinine, N-methylleucine, kynurenine, penicillamine, 4-aminophenylalanine, 3-(2-naphthyl)alanine, 3-(1-naphthyl)alanine, methionine sulfone, methionine sulfoxide, t-butylalanine, 4-hydroxyphenylglycine, aminoalanine, 1,2,3,4 tetrahydorisoquinoline-3-carboxylic acid, vinylalanine, propargylglycine, 1,2,4-triazolo-3-alanine, 4,4,4-trifluoro-threonine, thyronine, 6-hydroxytryptophan, 5-hydroxytryptophan, 3-hydroxykynurenine, 3-aminotyrosine, trifluoromethylalanine (2-(4-pyridyl)ethyl)cysteine, 3,4-dimethoxy-phenylalanine, 3-(2-thiazolyl)alanine, ibotenic acid, quisqualic acid, 3-trifluoromethylphenylalanine, 4-trifluoromethylphenylalanine, t-butylglycine, cyclopentylglycine, cyclohexylglycine, phenylglycine, cyclohexylalanine, thiohistidine, 3-methoxytyrosine, norleucine, norvaline, alloisoleucine, thioproline, dehydroproline, hydroxyproline, isonipectotic acid, homoproline, N-acetyl lysine, aminophenylbutyric acid, phenylalanines substituted at the ortho, meta or para position of the phenyl moiety with one or two of the following: a ($C_1$–$C_4$) alkyl, a ($C_1$–$C_4$) alkoxy, halogen or nitro groups or substituted with a methylenedioxy group, β-2- and 3-thienylalanine, β-2- and 3-furanylalanine, 2-, 3- and 4-pyridylalanine, β-(benzothienyl-2- and 3-yl)alanine, β-(1- and 2-naphthyl)alanine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine and 3-nitrotyrosine.

In one embodiment of a compound of Formula (II), n is 1 and $R^3$ is hydrogen, alkyl, substituted alkyl, aryl, substituted aryl, arylalkyl, cycloalkyl or heteroaryl. In another embodiment, n is 1 and $R^3$ is hydrogen, alkyl or substituted alkyl. Preferably, $R^3$ is hydrogen or $C_{1-4}$ alkyl.

In still another embodiment of a compound of Formula (II), n is 1 and $R^3$ is hydrogen, aryl or substituted aryl. Preferably, $R^3$ is hydrogen, phenyl or substituted phenyl.

In still another embodiment of a compound of Formula (II), n is 1 and $R^3$ is hydrogen, arylalkyl or substituted arylalkyl. Preferably, $R^3$ is hydrogen, benzyl or substituted benzyl.

In still another embodiment of a compound of Formula (II), $R^{10}$ is $[R^5NH(CHR^4)_pC(O)]—$, p is 1 and $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, $R^4$ and $R^5$ together with the atoms to which they are bonded, form a cycloheteroalkyl or substituted cycloheteroalkyl ring.

In still another embodiment of a compound of Formula (II), $R^{10}$ is $[R^5NH(CHR^4)_nC(O)]$—, p is 1, $R^5$ is hydrogen and $R^4$ is hydrogen, alkanyl or cycloalkanyl. Preferably, $R^4$ is hydrogen, methyl, isopropyl, isobutyl, sec-butyl, t-butyl, cyclopentyl or cyclohexyl.

In still another embodiment of a compound of Formula (II), $R^{10}$ is $[R^5NH(CHR^4)_pC(O)]$—, p is 1, $R^5$ is hydrogen and $R^4$ is substituted alkanyl. Preferably, $R^4$ is —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$ or —$CH_2CH_2CH_2NHC(NH)NH_2$.

In still another embodiment of a compound of Formula (II), $R^{10}$ is $[R^5NH(CHR^4)_pC(O)]$—, p is 1, $R^5$ is hydrogen and $R^4$ is aryl, arylalkanyl, substituted arylalkanyl or heteroarylalkanyl. Preferably, $R^4$ is phenyl, benzyl, 4-hydroxybenzyl, 4-imidazolylmethyl or 3-indolylmethyl.

In still another embodiment of a compound of Formula (II), $R^{10}$ is $[R^5NH(CHR^4)_pC(O)]$—, p is 1 and $R^4$ and $R^5$ together with the atoms to which they are bonded form a cycloheteroalkyl or substituted cycloheteroalkyl ring. Preferably, $R^4$ and $R^5$ together with the atoms to which they are bonded form an azetidine, pyrrolidine or piperidine ring.

In still another embodiment of a compound of Formula (II), $R^{10}$ is $[R^5NH(CHR^4)_nC(O)]$—, p is 1, $R^4$ is hydrogen, alkanyl, substituted alkanyl, aryl, substituted aryl, arylalkanyl, substituted arylalkanyl, cycloalkanyl, heteroarylalkyl or substituted heteroarylalkyl, $R^5$ is $R^6$—, $R^6C(O)$— or $R^6OC(O)$—, and $R^6$ is alkyl, substituted alkyl, aryl, substituted aryl, arylalkyl, substituted arylalkyl, cycloalkyl, substituted cycloalkyl, cycloheteroalkyl, heteroaryl, substituted heteroaryl or heteroarylalkyl. Preferably $R^6$ is selected from the group consisting of $C_{1-4}$ alkyl, phenyl, substituted phenyl, benzyl or substituted benzyl.

In still another embodiment of a compound of Formula (II), $R^{10}$ is $[R^5NH(CHR^4)_pC(O)]$—, p is 2 and each $R^4$ is independently hydrogen, alkanyl, substituted alkanyl, aryl, substituted aryl, arylalkanyl, substituted arylalkanyl, cycloalkanyl, heteroarylalkanyl or substituted heteroarylalkanyl. Preferably, each $R^4$ is independently hydrogen, $C_{1-4}$ alkyl, cyclopentyl, cyclohexyl, phenyl, substituted phenyl, benzyl or substituted benzyl. More preferably, $R^{10}$ is $[R^5NH(CHR^4)_pC(O)]$—, p is 2, $R^5$ is hydrogen, and each $R^4$ is independently hydrogen, $C_{1-4}$ alkyl, cyclopentyl, cyclohexyl, phenyl, substituted phenyl, benzyl or substituted benzyl.

In still another embodiment of a compound of Formula (II), q is 1, $R^8$ is hydrogen or methyl and $R^9$ is hydrogen, alkanyl, substituted alkanyl, aryl, substituted aryl, arylalkanyl, substituted arylalkanyl, cycloalkanyl, heteroarylalkanyl or substituted heteroarylalkanyl.

In still another embodiment of a compound of Formula (II), q is 1, $R^8$ is hydrogen or methyl and $R^9$ is hydrogen, alkanyl or cycloalkanyl. Preferably, $R^9$ is hydrogen, methyl, isopropyl, isobutyl, sec-butyl, t-butyl, cyclopentyl or cyclohexyl.

In still another embodiment of a compound of Formula (II), q is 1, $R^8$ is hydrogen or methyl and $R^9$ is substituted alkanyl. Preferably, $R^9$ is —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$ or —$CH_2CH_2CH_2NHC(NH)NH_2$.

In still another embodiment of a compound of Formula (II), q is 1, $R^8$ is hydrogen or methyl and $R^9$ is aryl, arylalkanyl, substituted arylalkanyl or heteroarylalkanyl. Preferably, $R^9$ is phenyl, benzyl, 4-hydroxybenzyl, 4-imidazolylmethyl or 3-indolylmethyl.

In still another embodiment of a compound of Formula (II), q is 1, and $R^8$ and $R^9$ together with the atoms to which they are bonded form a cycloheteroalkyl or substituted cycloheteroalkyl ring. Preferably $R^8$ and $R^9$ together with the atoms to which they are bonded form an azetidine, pyrrolidine or piperidine ring.

In still another embodiment of a compound of Formula (II), q is 2, $R^8$ is hydrogen or methyl and each $R^9$ is independently hydrogen, alkanyl, substituted alkanyl, aryl, substituted aryl, arylalkanyl, substituted arylalkanyl, cycloalkanyl, heteroarylalkanyl or substituted heteroarylalkanyl. More preferably, $R^8$ is hydrogen and each $R^9$ is independently hydrogen, $C_{1-4}$ alkyl, cyclopentyl, cyclohexyl, phenyl, substituted phenyl, benzyl or substituted benzyl.

In still another embodiment of a compound of Formula (II), n is 0, q is 1, $R^{10}$ is $[R^5NH(CHR^4)PC(O)]$—, p is 1, and $R^5$ is hydrogen to provide a compound of Formula (XVI):

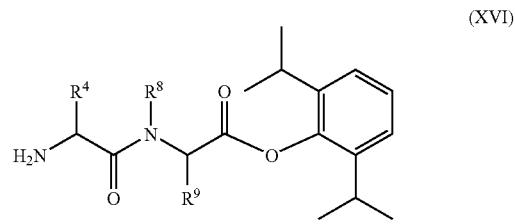

(XVI)

wherein $R^4$ is hydrogen, alkanyl, substituted alkanyl, aryl, substituted aryl, arylalkanyl, substituted arylalkanyl, cycloalkanyl, heteroarylalkanyl or substituted heteroarylalkanyl, $R^8$ is hydrogen or methyl and $R^9$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, $R^8$ and $R^9$ together with the atoms to which they are bonded, form a cycloheteroalkyl or substituted cycloheteroalkyl ring.

In one embodiment of a compound of Formula (XVI), $R^8$ is hydrogen and $R^9$ is hydrogen, methyl, isopropyl, isobutyl, sec-butyl, t-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl, 3-indolylmethyl, or optionally, $R^8$ and $R^9$ together with the atoms to which they are bonded form an azetidine, pyrrolidine or piperidine ring.

In another embodiment of a compound of Formula (XVI), $R^4$ is hydrogen, alkanyl or cycloalkanyl. Preferably, $R^4$ is hydrogen, methyl, isopropyl, isobutyl, sec-butyl, t-butyl, cyclopentyl or cyclohexyl. Preferably, $R^8$ is hydrogen and $R^9$ is hydrogen, methyl, isopropyl, isobutyl, sec-butyl, t-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2$-

(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl, or optionally, R$^8$ and R$^9$ together with the atoms to which they are bonded, form an azetidine, pyrrolidine or piperidine ring.

In still another embodiment of a compound of Formula (XVI), R$^4$ is substituted alkanyl. Preferably, R$^4$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. Preferably, R$^8$ is hydrogen and R$^9$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl, or optionally, R$^8$ and R$^9$ together with the atoms to which they are bonded, form an azetidine, pyrrolidine or piperidine ring.

In still another embodiment of a compound of Formula (XVI), R$^4$ is aryl, arylalkanyl, substituted arylalkanyl or heteroarylalkanyl. Preferably, R$^4$ is phenyl, benzyl, 4-hydroxybenzyl, 4-imidazolylmethyl or 3-indolylmethyl. Preferably, R$^8$ is hydrogen and R$^9$ is hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl or optionally, R$^8$ and R$^9$ together with the atoms to which they are bonded, form an azetidine, pyrrolidine or piperidine ring.

In still another embodiment of a compound of Formula (XVI), the α-carbon of the N-terminal amino acid residue is of the L-configuration. In still another embodiment of a compound of Formula (XVI), the α-carbon of the N-terminal amino acid residue is of the D-configuration. In still another embodiment of a compound of Formula (XVI), the α-carbon of the C-terminal amino acid residue is of the L-configuration. In still another embodiment of a compound of Formula (XVI), the α-carbon of the C-terminal amino acid residue is of the D-configuration. In still another embodiment of a compound of Formula (XVI), the α-carbons of both the N- and C-terminal amino acid residues are of the L-configuration.

In still another embodiment of a compound of Formula (II), n is 1, q is 1, R$^{10}$ is hydrogen, R$^3$ is hydrogen, alkyl, substituted alkyl, aryl, substituted aryl, arylalkyl, cycloalkyl or heteroaryl, R$^8$ is hydrogen, R$^9$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, R$^8$ and R$^9$ together with the atoms to which they are bonded, form a cycloheteroalkyl or substituted cycloheteroalkyl ring. Preferably, R$^3$ is hydrogen, C$_{1-4}$ alkyl, phenyl, substituted phenyl, benzyl or substituted benzyl, more preferably, R$^3$ is hydrogen or methyl.

In still another embodiment of a compound of Formula (II), n is 1, q is 1, and R$^{10}$ is hydrogen, to provide a compound of Formula (XVII):

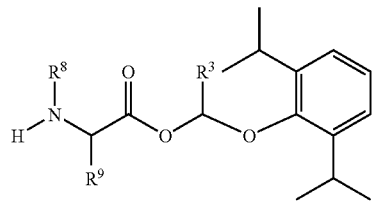

wherein R$^3$ is hydrogen or methyl, R$^8$ is hydrogen or methyl and R$^9$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, R$^8$ and R$^9$ together with the atoms to which they are bonded form a cycloheteroalkyl or substituted cycloheteroalkyl ring. Preferably, in a compound of Formula (XVII), R$^8$ is hydrogen.

In one embodiment of a compound of Formula (XVII), R$^9$ is hydrogen, alkanyl or cycloalkanyl. Preferably, R$^9$ is hydrogen, methyl, isopropyl, isobutyl, sec-butyl, t-butyl, cyclopentyl or cyclohexyl.

In another embodiment of a compound of Formula (XVII), R$^9$ is substituted alkanyl. Preferably, R$^9$ is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$.

In still another embodiment of a compound of Formula (XVII), R$^9$ is aryl, arylalkanyl, substituted arylalkanyl or heteroarylalkanyl. Preferably, R$^9$ is phenyl, benzyl, 4-hydroxybenzyl, 4-imidazolylmethyl or 3-indolylmethyl.

In still another embodiment of a compound of Formula (XVII), R$^8$ and R$^9$ together with the atoms to which they are bonded form a cycloheteroalkyl or substituted cycloheteroalkyl ring. Preferably, R$^8$ and R$^9$ together with the atoms to which they are bonded form an azetidine, pyrrolidine or piperidine ring.

In one embodiment of a compound of Formula (XVII), the α-carbon of the amino acid residue is of the L-configuration. In another embodiment of a compound of Formula (XVII), the α-carbon of the amino acid residue is of the D-configuration.

In still another embodiment of a compound of Formula (XVII), R$^3$ is hydrogen.

In still another embodiment of a compound of Formula (II), n is 1, q is 1, R$^{10}$ is [R$^5$NH(CHR$^4$)$_p$C(O)]—, p is 1, R$^3$ is hydrogen, alkyl, substituted alkyl, aryl, substituted aryl, arylalkyl, cycloalkyl or heteroaryl, R$^4$ is hydrogen, alkanyl, substituted alkanyl, aryl, substituted aryl, arylalkanyl, substituted arylalkanyl, cycloalkanyl, heteroarylalkanyl or substituted heteroarylalkanyl, R$^5$ is hydrogen, R$^8$ is hydrogen or methyl, R$^9$ is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, R$^8$ and R$^9$ together with the atoms to which they are bonded, form a cycloheteroalkyl or substituted cycloheteroalkyl ring. Preferably R$^3$ is hydrogen, C$_{1-4}$ alkyl, phenyl, substituted phenyl, benzyl or substituted benzyl, more preferably, R$^3$ is hydrogen or methyl. Preferably, R[8] is hydrogen and R[9] is hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl or optionally, R[8] and R[9] together with the atoms to which they are bonded form an azetidine, pyrrolidine or piperidine ring.

In still another embodiment of a compound of Formula (II), n is 1, q is 1, R[10] is [R[5]NH(CHR[4])$_p$C(O)]—, p is 1, and R[5] is hydrogen to provide a compound of Formula (XVIII):

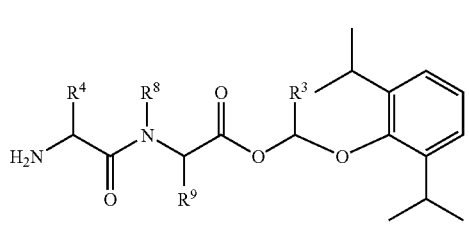

(XVIII)

wherein R[3] is hydrogen or methyl, R[4] is hydrogen, alkanyl, substituted alkanyl, aryl, substituted aryl, arylalkanyl, substituted arylalkanyl, cycloalkanyl, heteroarylalkanyl or substituted heteroarylalkanyl, R[8] is hydrogen or methyl and R[9] is hydrogen, alkanyl, substituted alkanyl, aryl, substituted aryl, arylalkanyl, substituted arylalkanyl, cycloalkanyl, heteroarylalkanyl or substituted heteroarylalkanyl, or optionally, R[8] and R[9] together with the atoms to which they are bonded, form a cycloheteroalkyl or substituted cycloheteroalkyl ring.

In one embodiment of a compound of Formula (XVIII), R[4] is hydrogen, alkanyl or cycloalkanyl. Preferably, R[4] is hydrogen, methyl, isopropyl, isobutyl, sec-butyl, t-butyl, cyclopentyl or cyclohexyl. Preferably, R[8] is hydrogen and R[9] is hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl or optionally, R[8] and R[9] together with the atoms to which they are bonded, form an azetidine, pyrrolidine or piperidine ring.

In another embodiment of a compound of Formula (XVIII), R[4] is substituted alkanyl. Preferably, R[4] is —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$ or —CH$_2$CH$_2$CH$_2$NHC(NH)NH$_2$. Preferably, R[8] is hydrogen and R[9] is hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl benzyl, 4-hydroxybenzyl, 4-imidazolylmethyl or 3-indolylmethyl or optionally, R[8] and R[9] together with the atoms to which they are bonded, form an azetidine, pyrrolidine or piperidine ring.

In still another embodiment of a compound of Formula (XVIII), R[4] is aryl, arylalkanyl, substituted arylalkanyl or heteroarylalkanyl. Preferably, R[4] is phenyl, benzyl, 4-hydroxybenzyl, 4-imidazolylmethyl or 3-indolylmethyl. Preferably, R[8] is hydrogen and R[9] is hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl, or optionally, R[8] and R[9] together with the atoms to which they are bonded form an azetidine, pyrrolidine or piperidine ring.

In still another embodiment of a compound of Formula (XVIII), the α-carbon of the N-terminal amino acid residue is of the L-configuration. In still another embodiment of a compound of Formula (XVIII), the α-carbon of the N-terminal amino acid residue is of the D-configuration. In still another embodiment of a compound of Formula (XVIII), the α-carbon of the C-terminal amino acid residue is of the L-configuration. In still another embodiment of a compound of Formula (XVIII), the α-carbon of the C-terminal amino acid residue is of the D-configuration. In still another embodiment of a compound of Formula (XVIII), the α-carbons of both the N- and C-terminal amino acid residues are of the L-configuration.

In still another embodiment of a compound of Formula (XVIII), R[3] is hydrogen.

Compounds of structural Formulae (I)–(XVIII) may be administered orally and transported across cells (i.e., enterocytes) lining the lumen of the gastrointestinal tract. While not wishing to be bound by any particular transport mechanism, some of the compounds of structural Formulae (I)–(XVIII) may be substrates for the proton-coupled intestinal peptide transport system ("PEPT1") (Leibach et al., *Annu. Rev. Nutr.* 1996, 16, 99–119) which, typically mediates the cellular uptake of small intact peptides consisting of two or three amino acids that are derived from the digestion of dietary proteins. In the intestine, where small peptides are not effectively absorbed by passive diffusion, PEPT1 may act as a vehicle for their effective uptake across the apical membrane of the gastric mucosa.

Methods for determining whether compounds of Formulae (I)–(XVIII) serve as substrates for the PEPT1 transporter are disclosed in Example 131 herein (see Section 5). In vitro systems, which use cells engineered to heterologously express the transport system, or cell-lines that endogenously express the transporter (e.g. Caco-2 cells) may be used to assay transport of compounds of Formulae (I)–(XVIII) by PEPT1 transporter. Standard methods for evaluating the enzymatic conversion of propofol prodrug compounds to propofol in vitro are disclosed in Example 132 herein.

Oral administration of propofol prodrug compounds to rats and monkeys is described in Examples 134 and 135 respectively.

4.3 Synthesis of Propofol Prodrug Compounds

The compounds of Formulae (I)–(XVIII) may be obtained via the synthetic methods illustrated in Schemes 1–10. Starting materials useful for preparing these compounds and intermediates thereof are commercially available or can be prepared by well-known synthetic methods (Harrison et al., "Compendium of Synthetic Organic Methods", Vols. 1–8 (John Wiley and Sons, 1971–1996); "Beilstein Handbook of Organic Chemistry," Beilstein Institute of Organic Chemistry, Frankfurt, Germany; Feiser et al, "Reagents for Organic Synthesis," Volumes 1–17, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesis of the compounds described herein and/or starting materials are either described in the art or will be readily apparent to the skilled artisan. Accordingly, the methods presented in Schemes 1–10 herein are illustrative rather than comprehensive.

Certain amino acid building blocks useful for the preparation of compounds of Formula (I) are illustrated in Scheme 1. Amino acids of either L- or D-stereochemistry may be used in these reactions. Compound (2) is a protected aspartic or glutamic acid residue, where the protecting groups $Pg^1$ and $Pg^2$ are removable under orthogonal conditions. Non-limiting Examples of useful protecting groups for the nitrogen atom include tert-butyloxycarbonyl (Boc), benzyloxycarbonyl (CBz) and 9-fluorenylmethyloxycarbonyl (Fmoc) moieties, while those for the carboxyl group include tert-butyl, benzyl and 9-fluorenylmethyl esters. Nitrogen protected amino acid residues may be conveniently activated for coupling via conversion to their NHS esters, as illustrated by the preparation of compounds (7) and (8).

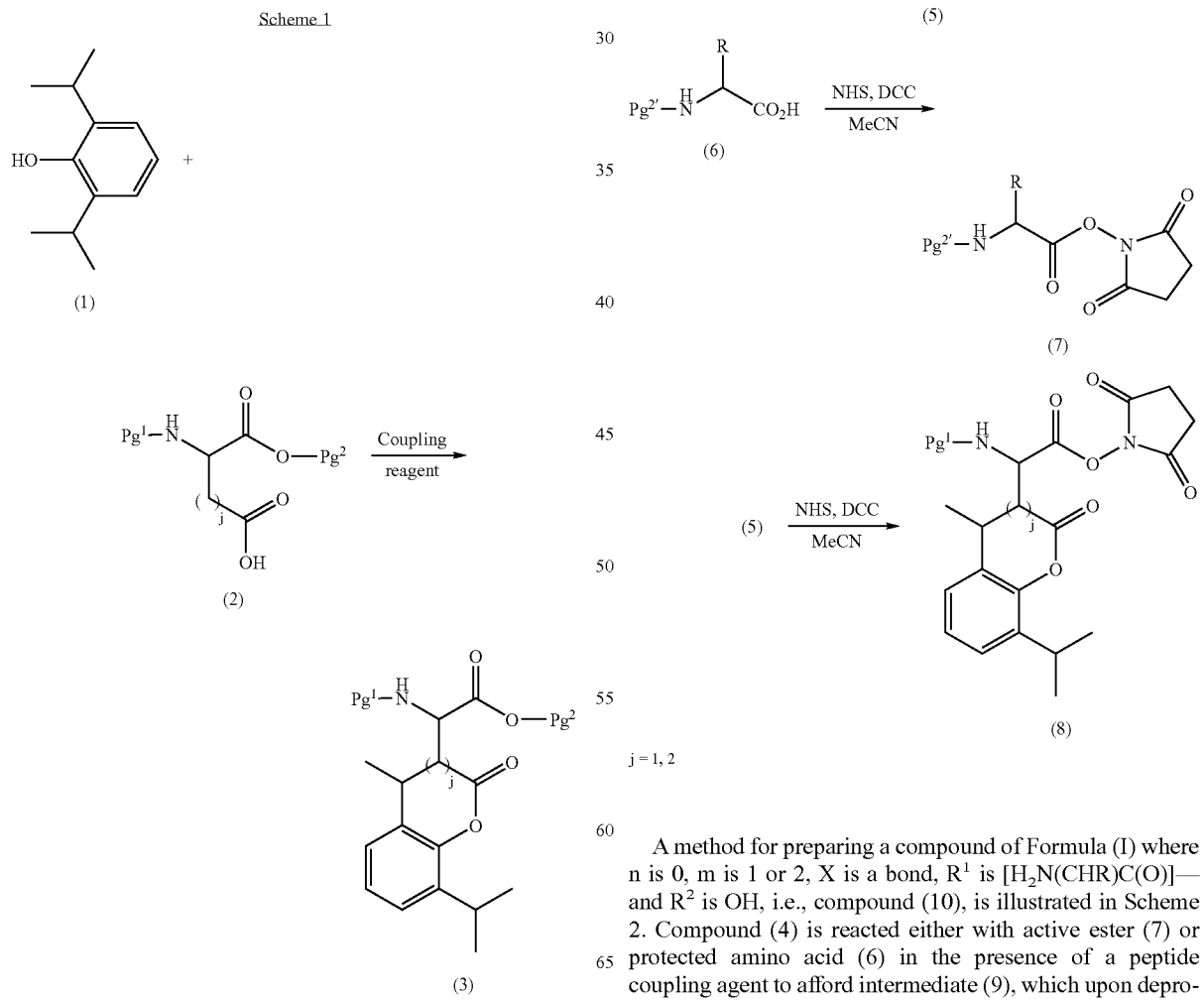

A method for preparing a compound of Formula (I) where n is 0, m is 1 or 2, X is a bond, $R^1$ is [$H_2N(CHR)C(O)$]— and $R^2$ is OH, i.e., compound (10), is illustrated in Scheme 2. Compound (4) is reacted either with active ester (7) or protected amino acid (6) in the presence of a peptide coupling agent to afford intermediate (9), which upon deprotection yields compound (10).

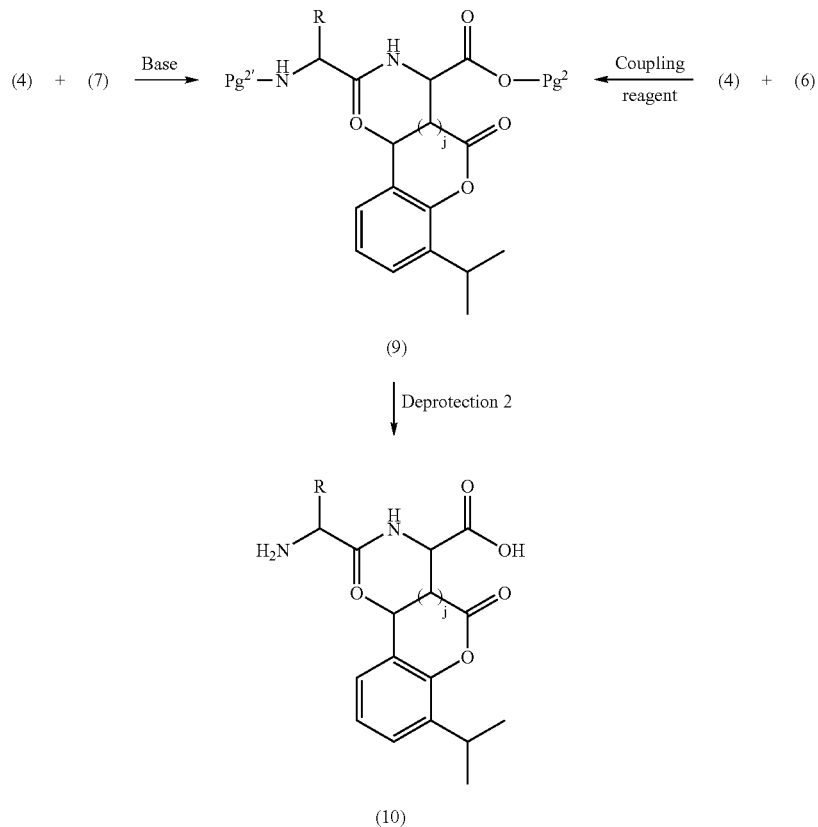
In a similar fashion, a method for preparing a compound of Formula (I) where n is 0, m is 1 or 2, X is a bond, $R^1$ is hydrogen and $R^2$ is —[NH(CHR)C(O)OH], i.e., compound (13), is illustrated in Scheme 3. Compound (11) is reacted either with active ester (8) or protected amino acid (5) in the presence of a peptide coupling agent to afford intermediate (12), which upon deprotection yields compound (13).
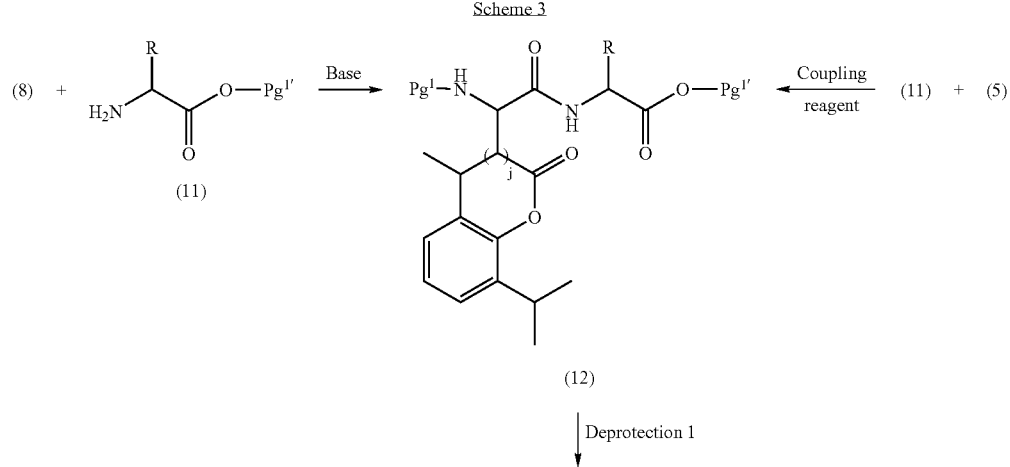

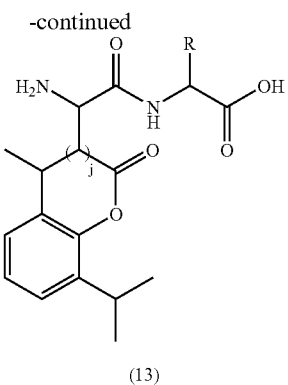

(13)

Compounds of Formula (I) may also be prepared via solid-phase synthesis methods, as is illustrated in Scheme 4 below for the preparation of compounds (10) and (13).

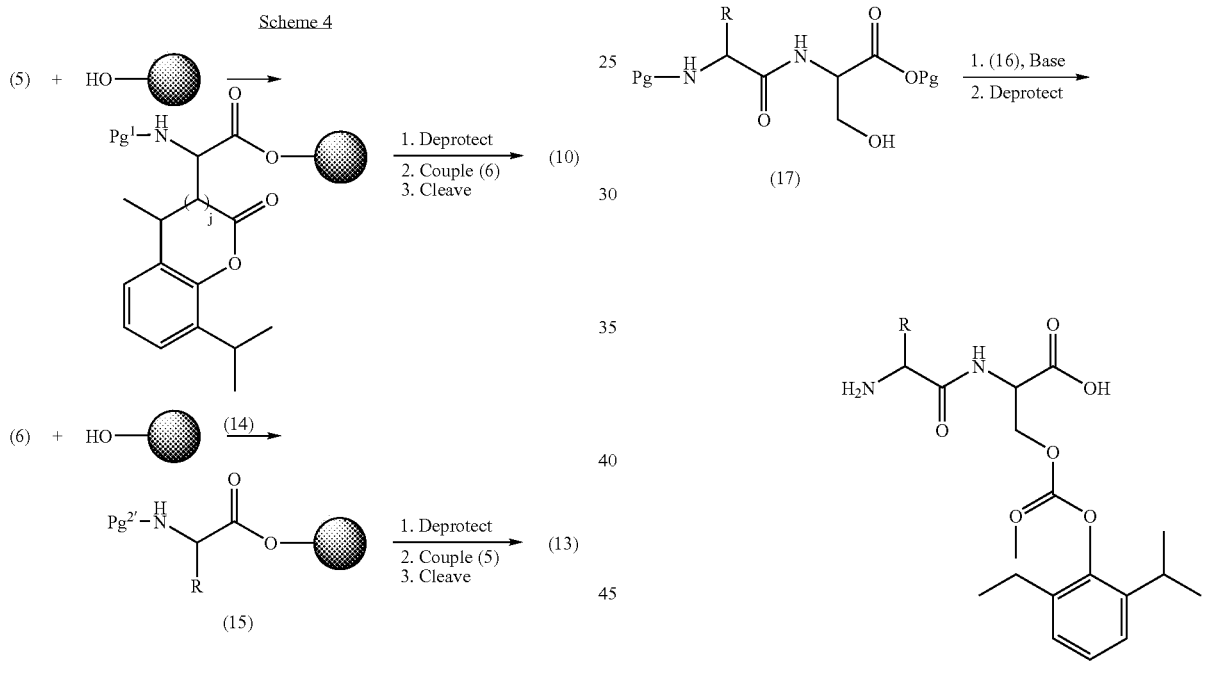

Compounds of Formula (I) where n is 0, m is 1, X is O, $R^1$ is [$H_2N(CHR)C(O)$]— and $R^2$ is OH, i.e., compound (18), may be prepared by methods illustrated in Scheme 5. Propofol is converted to the chloroformate derivative (16) by treatment with a phosgene equivalent and then reacted with serine dipeptide (17). Deprotection affords the propofol carbonate compound (18).

Scheme 5

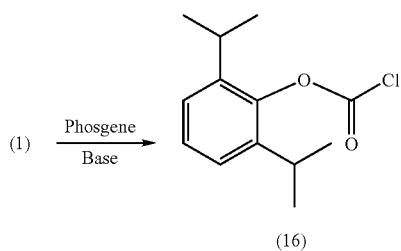

Compounds of Formula (I) where n is 1, m is 1 or 2, X is a bond, $R^1$ is [$H_2N(CHR)C(O)$]— and $R^2$ is OH, i.e., compound (23), may be prepared by methods illustrated in Scheme 6. The protected aspartate or glutamate dipeptide (19) is treated with the gem-dialkylating agent (20) in the presence of a base or metal promoter agent (typically a soluble $Ag^+$ or $Hg^{2+}$ salt) to afford intermediate (21). Displacement of the second leaving group $X_2$ from (21) by propofol generates acyloxyalkyl ether (22), which upon deprotection affords the desired compound (23). If $X_2$ in (27) is SR (e.g., thiomethyl), activation by treatment with sulfuryl chloride or similar halogenating agent precedes displacement by propofol to generate compound (22).

Scheme 6

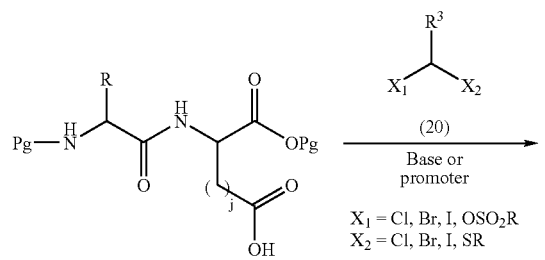

$X_1$ = Cl, Br, I, $OSO_2R$
$X_2$ = Cl, Br, I, SR (19)

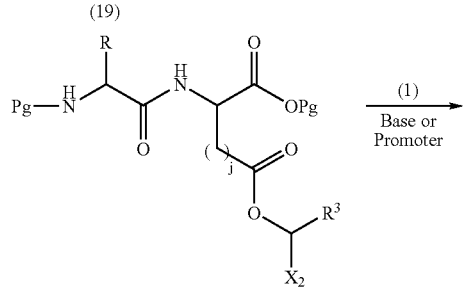

(21)

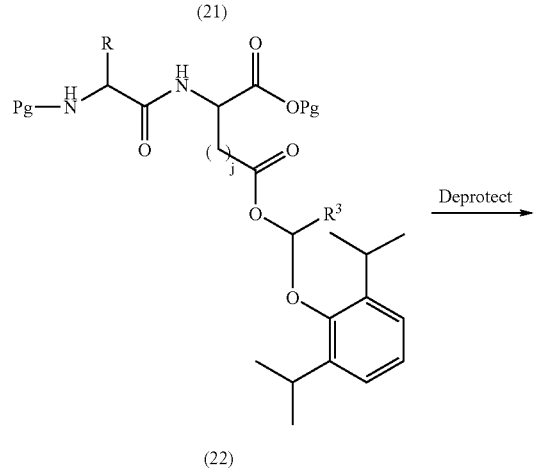

(22)

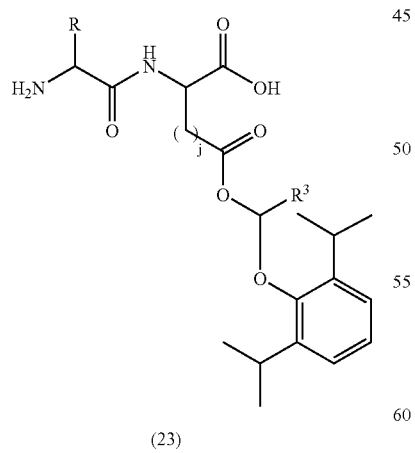

(23)

Alternatively, compound (22) may be prepared by first generating the haloalkyl (or thioalkyl) propofol ether (24), then displacing the leaving group $X_2$ with the carboxylate anion of dipeptide (19), as shown in Scheme 7.

Scheme 7

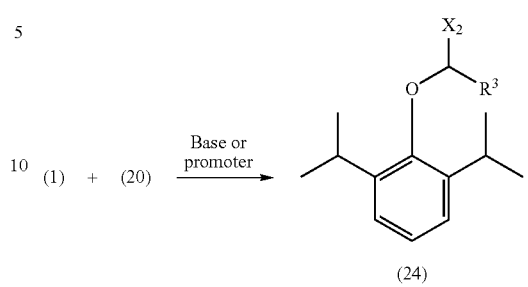

(24)

(19) $\xrightarrow[\text{Base or promoter}]{(24)}$ (22)

In an analogous manner, compounds of Formula (I) where n is 1, m is 1 or 2, X is a bond, $R^1$ is hydrogen, and $R^2$ is —[NH(CHR)C(O)OH], i.e., compound (28), may be prepared as illustrated in Scheme 8.

Scheme 8

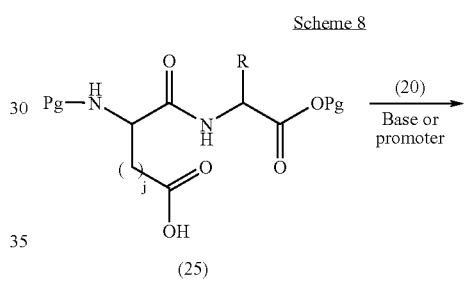

(25)

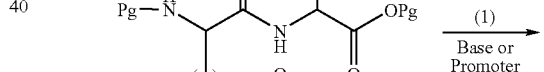

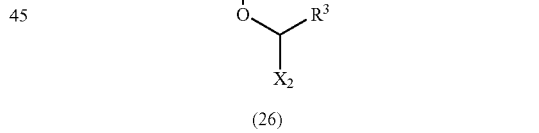

(27)

-continued

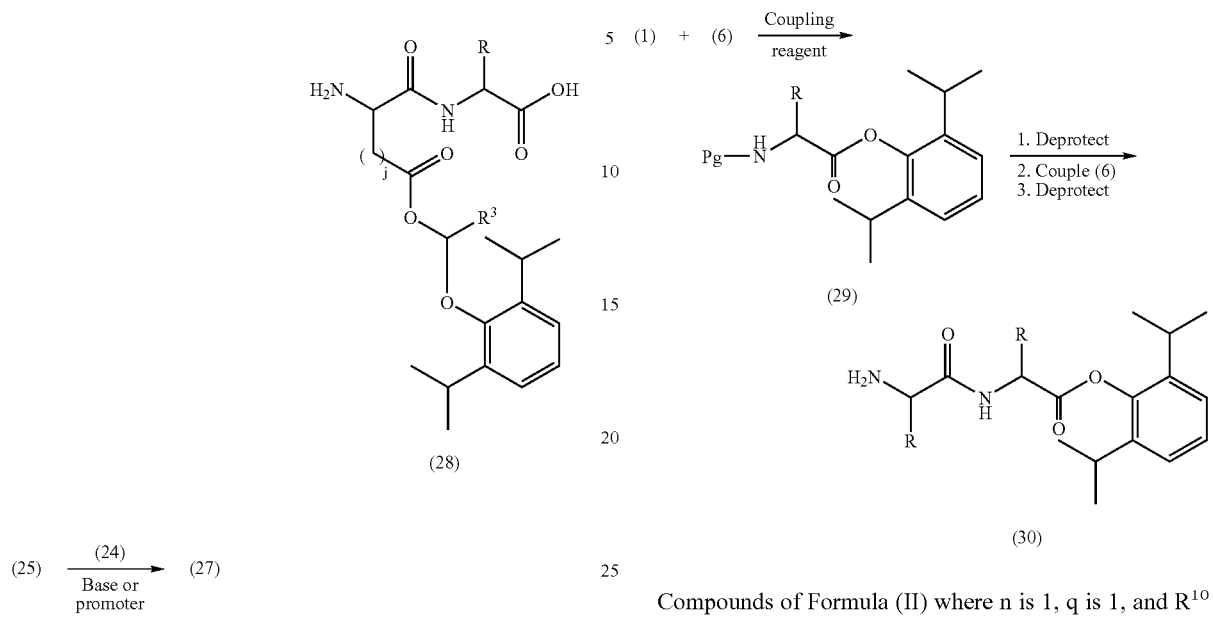

Compounds of Formula (II) where n is 0, q is 1, and $R^{10}$ is [$H_2N(CHR)C(O)$]—, i.e., compound (30), may be prepared according to methods illustrated in Scheme 9.

Compounds of Formula (II) where n is 1, q is 1, and $R^{10}$ is hydrogen, i.e., compound (33), and where n is 1, q is 1, and $R^{10}$ is [$H_2N(CHR)C(O)$]—, i.e., compound (34), may be prepared according to methods illustrated in Scheme 10. Synthesis of intermediate (32) proceeds either via haloalkyl ester (31) or haloalkyl ether (24) as previously described.

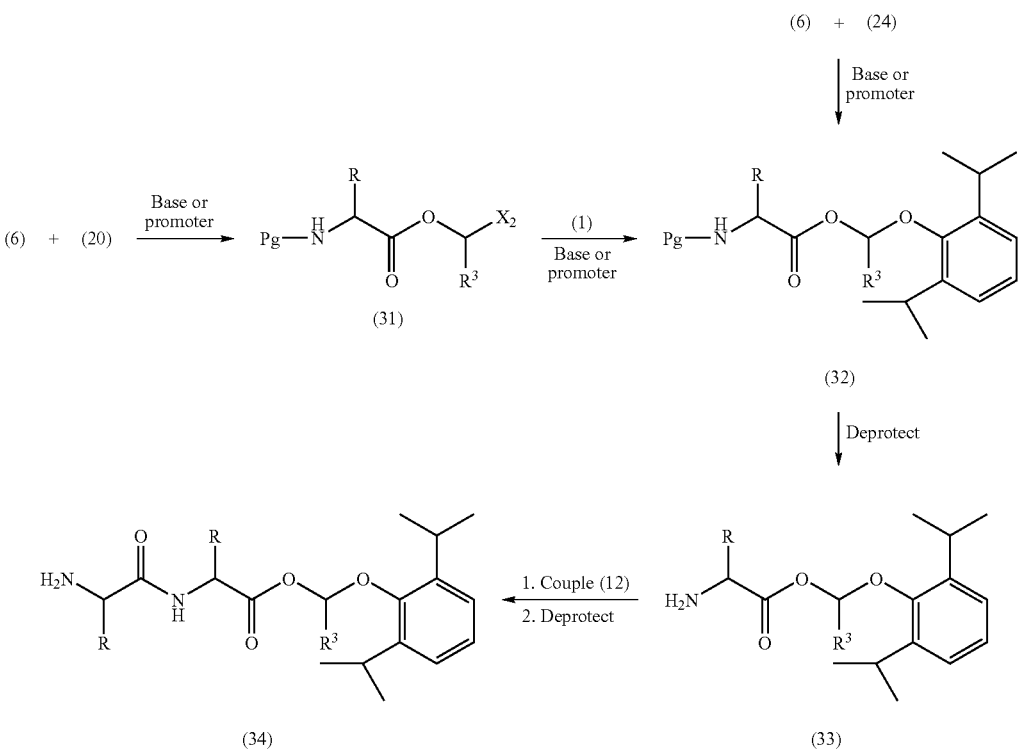

4.4 Therapeutic/Prophylactic Uses and Methods of Administration

The compounds of Formulae (I)–(XVIII), as described herein, may be used to treat and/or prevent migraine in patients. The methods comprise administering to a patient a therapeutically effective amount of a compound of Formulae (I)–(XVIII) to treat and/or prevent migraine. In the therapeutic methods herein, a therapeutically effective amount of the compound is administered to a patient suffering from a migraine headache. In the prophylactic methods herein, a therapeutically effective amount of the compound is administered to a patient at risk of developing a migraine.

In one embodiment, the compounds are administered orally to treat and/or prevent migraine. However, in other embodiments, the compounds are administered parenterally (e.g., via inhalation or injection). In one embodiment, the compounds are administered in amounts of between about 10 mg to about 4 g to treat or prevent migraine.

The compounds of Formulae (I)–(XVIII) may also be used as anti-emetics and can be administered to patients at risk of vomiting and/or who are nauseous. For Example, the compounds may be administered to patients that are being concurrently treated with various chemotherapy agents and/or surgical procedures, which induce nausea, in order to treat and/or prevent nausea and vomiting. Typically, a therapeutically effective amount of the compound is administered to a patient to treat and/or prevent nausea and vomiting.

In one embodiment, the compounds are administered orally to treat and/or prevent nausea or vomiting. However, in other embodiments, the compounds are administered parenterally (e.g., via inhalation or injection to treat and/or prevent nausea or vomiting. In one embodiment, the compounds are administered in amounts of between about 10 mg to about 4 g to treat and/or prevent nausea or vomiting.

The compounds of Formulae (I)–(XVIII) may also be used as hypnotic agents to induce and/or maintain general anesthesia and/or as a sedative. Typically, a therapeutically effective amount of the compound is administered to a patient to induce hypnosis, anesthesia and/or sedation.

In one embodiment, the compounds are administered intravenously when used as a general anesthetic. In another embodiment, the compounds are administered by inhalation. The compounds may be formulated by methods used to formulate propofol, which are well known in the art. In one embodiment, compounds of Formulae (I)–(XVIII) that are water soluble may be formulated as an injectable aqueous solution, which contains significantly less emulsifiers or solubilizers than used in aqueous formulations of propofol, thereby avoiding discomfort at the site of injection.

In one embodiment, the compounds are administered orally in amounts of about 10 mg to 4 g daily when used as a sedative (e.g., for the treatment of anxiety conditions). However, in another embodiment, the compounds may also be administered by inhalation, intravenously or intramuscularly when used as a sedative.

The compounds of Formulae (I)–(XVIII) may be administered in similar amounts and in the same schedule as described in the art for propofol. In one embodiment, dosage levels of the compounds of Formulae (I)–(XVIII) for producing general anesthesia, maintaining anesthesia and producing a sedative effect are as described in the art for propofol.

The compounds of Formulae (I)–(XVIII) may also be used to inhibit oxidation in biological materials. The methods involve contacting the biological material with an effective amount of the compound. In therapeutic methods herein, a therapeutically effective amount of the compound is administered to a patient suffering from a pathological condition treated by inhibition of oxidation. In prophylactic methods herein, a therapeutically effective amount of the compound is administered to a patient at risk of developing a disease as a result of exposure to oxidative stress. The compounds may find particular use in preventing and/or treating oxidation in disorders of the central nervous system that involve an inflammatory component.

The compounds of Formulae (I)–(XVIII) may be used to treat and/or prevent neurodegenerative conditions of the nervous system, which include, but are not limited to, Friedrich's disease, Parkinson's disease, Alzheimer's disease, Huntington's disease, amyotrophic lateral sclerosis (ALS), multiple sclerosis (MS) and Pick disease. In one embodiment, a therapeutically effective amount of a compound (e.g., between about 10 mg to about 4 g daily) is orally administered to treat and/or prevent chronic neurodegenerative diseases.

The compounds of Formulae (I)–(XVIII) may also be used to treat and/or prevent trauma to the central nervous system such as, for Example, skull fracture and its resulting edema, concussion, contusion, brain hemorrhages, shearing lesions, subdural and epidural hematoma, and spinal cord injury (e.g., mechanical injury due to compression or flexion of the spinal cord). In one embodiment, a compound is parenterally administered by intravenous injection or injection directly into the central nervous system (i.e., intrathecally ("IT") or into the brain) to treat and/or prevent traumatic conditions of the central nervous system. In another embodiment, a therapeutically effective amount of a compound (e.g., between about 25 mg to about 500 mg IV or IM and between about 5 mg to about 100 mg IT) are administered to treat and/or prevent traumatic conditions of the central nervous system.

The compounds of Formulae (I)–(XVIII) may also be used as anti-convulsives to treat and/or prevent seizures (e.g., epileptic seizures). Methods for treating and/or preventing convulsions comprise administering a therapeutically effective amount of a compound to a patient in need of such treatment. In one embodiment, the compounds are administered orally to treat and/or prevent convulsions. In another embodiment, the compounds are parenterally administered to treat and/or prevent convulsions. In still another embodiment, the compounds are administered in amounts of between about 10 mg to about 4 g daily to treat and/or prevent convulsions.

When used to treat and/or prevent the above disease or disorders compounds and/or pharmaceutical compositions of Formulae (I)–(XVIII) may be administered or applied singly, or in combination with other agents. The compounds and/or compositions may also be administered or applied singly, or in combination with other pharmaceutically active agents, including other compounds of Formulae (I)–(XVIII).

Provided herein are methods of treatment and prophylaxis by administering to a patient a therapeutically effective amount of a composition or compound of Formulae (I)–(XVIII). The patient may be an animal, is more preferably, a mammal and even more preferably, a human.

The compounds of Formulae (I)–(XVIII) and/or pharmaceutical compositions thereof are preferably administered orally. The compounds and/or pharmaceutical compositions thereof may also be administered by any other convenient route, for Example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In specific embodiments, it may be desirable to administer one or more compounds and/or pharmaceutical compositions thereof locally to the area in need of treatment. This may be achieved, for Example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes or fibers. In one embodiment, administration can be by direct injection at the site (or former site) of cancer or arthritis.

In certain embodiments, it may be desirable to introduce one or more compounds and/or pharmaceutical compositions thereof into the central nervous system by any suitable route, including intraventricular, intrathecal and epidural injection. Intraventricular injection may be facilitated by an intraventricular catheter, for Example, attached to a reservoir, such as an Ommaya reservoir.

In one embodiment, the compounds and/or pharmaceutical compositions can be delivered via sustained release systems, preferably oral sustained release systems. In one embodiment, a pump may be used (Langer, supra; Sefton, 1987, *CRC Crit Ref Biomed Eng.* 14:201; Saudek et al., 1989, *N. Engl. J. Med.* 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; Levy et al., 1985, *Science* 228: 190; During et al., 1989, *Ann. Neurol.* 25:351; Howard et al., 1989, *J. Neurosurg.* 71:105).

In still another embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.* 1984, 5(3) 1–9). Factors affecting drug release are well known to the skilled artisan and have been described in the art (Bamba et al., *Int. J. Pharm.* 1979, 2, 307).

In still another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.* 2000, 26:695–708). In a preferred embodiment, OROS™ osmotic devices are used for oral sustained release delivery devices (Theeuwes et al., U.S. Pat. No. 3,845,770; Theeuwes et al., U.S. Pat. No. 3,916,899).

For administration by inhalation, a compound may be conveniently delivered to the lung by a number of different devices. For Example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver compounds directly to the lung.

Alternatively, a Dry Powder Inhaler ("DPI") device may be used to administer a compound to the lung (See, e.g., Raleigh et al., *Proc. Amer. Assoc. Cancer Research Annual Meeting* 1999, 40, 397). DPI devices typically use a mechanism such as a burst of gas to create a cloud of dry powder inside a container, which may then be inhaled by the patient and are well known in the art and may be purchased from a number of commercial sources. A popular variation is the multiple dose DPI ("MDDPI") system, which allows for the delivery of more than one therapeutic dose. For Example, capsules and cartridges of gelatin for use in an inhaler or insufflator may be formulated containing a powder mix of a compound and a suitable powder base such as lactose or starch for these systems.

Another type of device that may be used to deliver a compound to the lung is a liquid spray device supplied, for Example, by Aradigm Corporation, Hayward, Calif. Liquid spray systems use extremely small nozzle holes to aerosolize liquid drug formulations that may then be directly inhaled into the lung.

In one embodiment, a nebulizer device is used to deliver a compound to the lung. Nebulizers create aerosols from liquid drug formulations by using, for Example, ultrasonic energy to form fine particles that may be readily inhaled (e.g., Verschoyle et al., *British J Cancer* 1999, 80, Suppl. 2, 96; Armer et al., U.S. Pat. No. 5,954,047; van der Linden et al., U.S. Pat. No. 5,950,619; van der Linden et al., U.S. Pat. No. 5,970,974).

In another embodiment, an electrohydrodynamic ("EHD") aerosol device is used to deliver a compound to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No., WO 94/12285; Coffee, International Publication No., WO 94/14543; Coffee, International Publication No., WO 95/26234, Coffee, International Publication No., WO 95/26235, Coffee, International Publication No., WO 95/32807). The electrochemical properties of a compound may be important parameters to optimize when delivering the compound to the lung with an EHD aerosol device, and such optimization is routinely performed by one of skill in the art. EHD aerosol devices may more efficiently deliver drugs to the lung than existing pulmonary delivery technologies. Other methods of intra-pulmonary delivery of a compound will be known to the skilled artisan.

The compounds of Formulae (I)–(XVIII) and/or compositions containing such compounds preferably provide therapeutic or prophylactic levels of propofol upon in vivo administration to a patient. While not wishing to bound by theory, the promoiety or promoieties of the compounds may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the administered compounds.

While not wishing to bound by theory, the promoiety or promoieties of the compounds may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). Preferably, propofol remains conjugated to a promoiety during transit across the intestinal mucosal barrier to provide protection from presystemic metabolism. In one embodiment, the compounds are essentially not metabolized to propofol within enterocytes, but are metabolized to the parent drug within the systemic circulation. Cleavage of the promoiety or promoieties of the compounds after absorption by the gastrointestinal tract may allow these prodrugs to be absorbed into the systemic circulation either by active transport, passive diffusion or by a mixture of both active and passive processes. In one embodiment, the compounds are actively absorbed through interaction with the intestinal peptide transporter PEPT1.

Cleavage of the promoiety or promoieties of the compounds of Formulae (I)–(XVIII) after absorption by the gastrointestinal tract, may allow these prodrugs to be absorbed into the systemic circulation from the large intestine. In one embodiment, the compounds and/or pharmaceutical compositions containing compounds of Formulae (I)–(XVIII) are preferably administered as sustained release systems. In another embodiment, the compounds and/or pharmaceutical compositions are delivered by oral sustained release administration. Preferably, in this embodiment, the compounds and/or pharmaceutical compositions are administered twice per day (more preferably, once per day).

4.5 Pharmaceutical Compositions

The present pharmaceutical compositions contain a therapeutically effective amount of one or more compounds of Formulae (I)–(XVIII), preferably, in purified form, together with a suitable amount of a pharmaceutically acceptable vehicle, so as to provide the form for proper administration to a patient. When administered intravenously to a patient, the compounds and pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of Formulae (I)–(XVIII) may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other Examples of suitable pharmaceutical vehicles have been described in the art (see Remington's Pharmaceutical Sciences, Philadelphia College of Pharmacy and Science, 19th Edition, 1995). Preferred pharmaceutical compositions are formulated for oral delivery.

Pharmaceutical compositions for oral delivery may be in the form of tablets, lozenges, aqueous or oily suspensions, granules, powders, emulsions, capsules, syrups, or elixirs, for Example. Orally administered pharmaceutical compositions may contain one or more optional agents, for Example, sweetening agents such as fructose, aspartame or saccharin, flavoring agents such as peppermint, oil of wintergreen, or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for Example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

A compound of Formulae (I)–(XVIII) may also be formulated in rectal or vaginal pharmaceutical compositions such as suppositories or retention enemas, e.g., containing conventional suppository bases such as cocoa butter or other glycerides.

In addition to the formulations described previously, a compound of Formulae (I)–(XVIII) may also be formulated as a depot preparation. Such long acting formulations may be administered by implantation (for Example subcutaneously or intramuscularly) or by intramuscular injection. Thus, for Example, a compound may be formulated with suitable polymeric or hydrophobic materials (for Example as an emulsion in an acceptable oil) or ion exchange resins, or as sparingly soluble derivatives, for Example, as a sparingly soluble salt.

When a compound of Formulae (I)–(XVIII) is acidic, it may be included in any of the above-described formulations as the free acid, a pharmaceutically acceptable salt, a solvate, hydrate or N-oxide. Pharmaceutically acceptable salts substantially retain the activity of the free acid, may be prepared by reaction with bases and tend to be more soluble in aqueous and other protic solvents than the corresponding free acid form.

Liquid drug formulations suitable for use with nebulizers and liquid spray devices and EHD aerosol devices will typically include a compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the compounds. Preferably, this material is liquid such as an alcohol, glycol, polyglycol or a fatty acid. Other methods of formulating liquid drug solutions or suspension suitable for use in aerosol devices are known to those of skill in the art (e.g., Biesalski, U.S. Pat. No. 5,112,598; Biesalski, U.S. Pat. No. 5,556,611).

4.6 Combination Therapy

In certain embodiments, the compounds of Formulae I)–(XVIII) can be used in combination therapy with at least one other therapeutic agent. The compound and the other therapeutic agent(s) can act additively or, more preferably, synergistically. In a preferred embodiment, a composition comprising a propofol prodrug compound is administered concurrently with the administration of another therapeutic agent, such as for Example, another sedative, hypnotic agent or anesthetic agent (e.g., propofol), which can be part of the same composition as the propofol prodrug compound or a different composition. In another embodiment, a composition comprising a propofol prodrug compound is administered prior or subsequent to administration of another therapeutic agent, such as, for Example, another sedative, hypnotic agent or anesthetic agent, (e.g., propofol).

5. EXAMPLES

The invention is further defined by reference to the following Examples, which describe preparation of compounds of Formulae (I)–(XVIII), compositions containing such compounds and assays for using such compounds and compositions. It will be apparent to those skilled in the art that many modifications, both to materials and methods, may be practiced without departing from the scope of the invention.

In the Examples below, the following abbreviations have the following meanings. If an abbreviation is not defined, it has its generally accepted meaning.

| | |
|---|---|
| Aib = | α-aminoisobutyric acid |
| Atm = | atmosphere |
| Boc = | tert-butyloxycarbonyl |
| Bzl = | benzyl |
| Cbz = | carbobenzyloxy |
| Dap = | L-2,3-diaminopropionic acid |
| DCC = | dicyclohexylcarbodiimide |
| DMAP = | 4-N,N-dimethylaminopyridine |
| DMEM = | Dulbecco's minimun eagle medium |
| DMF = | N,N-dimethylformamide |
| DMSO = | dimethylsulfoxide |
| Fmoc = | 9-fluorenylmethyloxycarbonyl |
| g = | gram |
| h = | hour |
| HBSS = | Hank's buffered saline solution |
| L = | liter |
| LC/MS = | liquid chromatography/mass spectroscopy |
| M = | molar |
| min = | minute |
| mL = | milliliter |
| mmol = | millimoles |
| NHS = | N-hydroxysuccinimide |
| PBS = | phosphate buffered saline |
| THF = | tetrahydrofuran |
| TFA = | trifluoroacetic acid |
| TMS = | trimethylsilyl |
| µL = | microliter |
| µM = | micromolar |
| v/v = | volume to volume |

Example 1

Boc-Asp(OPropofol)-OBzl (101)

To a homogeneous solution of Boc-Asp-OBzl (322 mg, 1.0 mmol), DMAP (12 mg, 0.1 mmol) and propofol (175 µL, 0.9 mmol) in tetrahydrofuran (3.5 mL) at room temperature was added dicyclohexylcarbodiimide (308 mg, 1.5 mmol). After stirring for 4 h, the dicyclohexylurea was filtered off and the solution was diluted with ether (100 mL). The ether layer was washed with 10% citric acid (2×25 mL), saturated sodium bicarbonate (2×25 mL), and brine (2×25 mL). The organic layer was dried over $Na_2SO_4$ and then concentrated in vacuo. The crude compound was purified by chromatography on silica gel (Biotage), eluting with a gradient of hexane to 10% EtOAc/hexane) to afford the title compound (101) (400 mg, 83% yield). $^1$H-NMR (400 MHz, $CD_3OD$): δ 7.34 (m, 5H), 7.16 (m, 3H), 5.20 (d, J=1.6 Hz, 2H), 4.68 (dd, $J_1$=5.6, 7.6 Hz, 1H), 3.30 (m, 1H), 3.13 (dd, J=7.6, 16.8 Hz, 1H), 2.93 (m, 2H), 1.44 (s, 9H), 1.1 (d, J=7.2 Hz, 12H); MS (ESI) m/z 506.34 (M+Na$^+$).

H-Asp(OPropofol)-OBzl (102)

Compound (101) was treated with 30% TFA (30 mL) in dichloromethane (70 mL) for 30 min and the solvent removed in vacuo to afford the title compound, which was used in subsequent reactions without further purification. MS (ESI) m/z 385.85 (M+H$^+$).

Boc-Asp(OPropofol)-OH (103)

To a flask containing 500 mg of 10% Pd—C was added a solution of compound (101) in methanol under nitrogen. The resulting mixture was degassed three times, after which hydrogen was introduced via a balloon apparatus. The suspended mixture was allowed to stir vigorously for 4 h. The reaction mixture was filtered through a pad of celite and concentrated in vacuo to arrive at the title compound, which was used in subsequent reactions without further purification. MS (ESI) m/z 392.32 (M–H$^+$).

Boc-Glu(OPropofol)-OBzl (104)

To a homogeneous solution of Boc-Glu-OBzl (7.20 g, 0.213 mol), DMAP (0.261 g, 0.021 mol) and propofol (3.76 mL, 0.20 mol) in tetrahydrofuran (40 mL) at room temperature was added dicyclohexylcarbodiimide (5.72 g, 0.278 mol). After stirring for 4 h, the dicyclohexylurea was filtered off and the solution was diluted with ether (250 mL). The ether layer was washed with 10% citric acid (2×100 mL), saturated sodium bicarbonate (2×100 mL), and brine (2×100 mL). The organic layer was dried over $Na_2SO_4$ and then concentrated in vacuo. The crude compound was purified by chromatography on silica gel (Biotage), eluting with a gradient of hexane to 10% EtOAc/hexane, to afford the title compound (8.20 g, 77% yield). $^1$H-NMR (400 MHz, CDCl$_3$): δ 7.36 (m, 5H), 7.15 (m, 3H), 5.21 (m, 2H), 4.45 (m, 1H), 2.89–2.75 (m, 2H), 2.74–2.63 (m, 2H), 2.34 (m, 1H), 2.10 (m, 1H), 1.46 (s, 9H), 1.18 (d, J=6.8 Hz, 12H). MS (ESI) m/z 521.36 (M+Na$^+$).

H-Glu(OPropofol)-OBzl (105)

Compound (104) was treated with 30% TFA (45 mL) in dichloromethane (105 mL) to arrive at the title compound (105), which was used in subsequent reactions without further purification. MS (ESI) m/z 398.37 (M+H$^+$).

Boc-Glu(OPropofol)-OH (106)

To a flask containing 500 mg of 10% Pd—C was added a solution of compound (104) in methanol under nitrogen. The resulting mixture was degassed three times, after which hydrogen was introduced via a balloon apparatus. The suspended mixture was allowed to stir vigorously for 4 h. The reaction mixture was filtered through a pad of celite and concentrated in vacuo to arrive at the title compound, which was used in following reactions without further purification. MS (ESI) m/z 407.31 (M–H$^+$).

Example 2

H-Ala-Asp(OPropofol)-OH (107)

To a homogeneous solution of CBz-Ala-OH (601 mg, 2.7 mmol) in acetonitrile (5 mL) was added DCC (667 mg, 3.2 mmol). N-Hydroxysuccinimide (434 mg, 3.8 mmol) was then added and the reaction was allowed to proceed at room temperature for 4 h. The resulting dicyclohexylurea was filtered and to the filtrate was added compound (102) (1.03 g, 2.7 mmol). Triethylamine (5 mL) was added and after stirring for 6 h, the solution was extracted with ethyl acetate (200 mL), washed with 10% citric acid (2×50 mL), saturated sodium bicarbonate (2×50 mL) and brine (2×50 mL). The organic layer was dried over Na$_2$SO$_4$ and then concentrated in vacuo. The crude compound was purified by chromatography on silica gel (Biotage), eluting with a gradient of hexane to 20% EtOAc/hexane) then the eluant was concentrated in vacuo to afford a white solid. This product was dissolved in a solution of 50% ethyl acetate:hexanes and added to a flask containing 100 mg of 10% Pd—C under nitrogen. The resulting mixture was degassed three times, then hydrogen was introduced via a balloon apparatus. The suspended solution was allowed to stir vigorously for 12 h. The reaction mixture was filtered through a pad of celite, concentrated in vacuo, and purified by preparative LC/MS to afford the title compound (107) (422 mg, 43% yield). $^1$H-NMR (400 MHz, CD$_3$OD): δ 7.16 (m, 3H), 4.63 (dd, J=4.8, 7.2 Hz 1H), 3.90 (q, J=7.2, 1H), 3.28–3.16 (m, 2H), 2.97 (m, 2H), 1.55 (d, J=7.2 Hz 3H), 1.18 (d, J=6.8 Hz, 12H). MS (ESI) m/z 365.32 (M+H$^+$).

Example 3

H-Phe-Asp(OPropofol)-OH (108)

Following procedures for preparation of compound (107), and substituting CBz-Phe-OH for CBz-Ala-OH, provided the title compound (108). MS (ESI) m/z 441.32 (M+H$^+$).

Example 4

H-β-Ala-Asp(OPropofol)-OH (109)

Following procedures for preparation of compound (107), and substituting CBz-β-Ala-OH for CBz-Ala-OH, provided the title compound (109). MS (ESI) m/z 365.32 (M+H$^+$).

Example 5

H-Abu-Asp(OPropofol)-OH (110)

Following procedures for preparation of compound (107), and substituting N-CBz-2-aminobutyric acid for CBz-Ala-OH, provided the title compound (110). MS (ESI) m/z 379.40 (M+H$^+$).

Example 6

H-Orn-Asp(OPropofol)-OH (111)

Following procedures for preparation of compound (107), and substituting α-N-CBz-δ-N-CBz-ornithine for CBz-Ala-OH, provided the title compound (111). MS (ESI) m/z 408.33 (M+H$^+$).

Example 7

H-NVal-Asp(OPropofol)-OH (112)

Following procedures for preparation of compound (107), and substituting CBz-norvaline for CBz-Ala-OH, provided the title compound (112). MS (ESI) m/z 393.48 (M+H$^+$).

Example 8

H-Sar-Asp(OPropofol)-OH (113)

Following procedures for preparation of compound (107), and substituting CBz-Sar-OH for CBz-Ala-OH, provided the title compound (113). MS (ESI) m/z 388.27 (M+Na$^+$).

Example 9

Preparation of H-Asp(OPropofol)-O-Trityl Resin (114)

To a suspension of 2-chlorotrityl resin (4.1 g, loading 1.69 mmol/g) and Fmoc-Asp(OPropofol)-OH (14.7 mmol) in DMF (50 mL) was added diisopropylethylamine (5.1 mL, 29.8 mmol) and O-(1H-benzotriazol-1-yl) N,N,N',N'-tetramethyluronium hexafluoro-phosphate (5.6 g, 14.7 mmol). The resulting reaction mixture was shaken at room temperature for 12 h. The resin was filtered and washed with DMF (3×50 mL), methanol (3×50 mL), and dichloromethane (3×50 mL). A 20% v/v piperidine/DMF solution (50 mL) was then added to the resin and after shaking for 1 h at room temperature, the resin was filtered, washed with DMF (3×50 mL), methanol (3×50 mL), and dichloromethane (3×50 mL), then allowed to dry in a desiccators over 24 h. The title resin was obtained and carried through subsequent steps.

Example 10

H-Asn-Asp(OPropofol)-OH (115)

To a suspension of the resin (114) (650 mg, loading 1.3 mmol/g) in DMF (8 mL) was added a homogeneous solution containing Boc-Asn-OH (392 mg, 1.7 mmol) diisopropylethylamine (0.43 mL, 4.5 mmol) and O-(1H-Benzotriazol-1-yl) N,N,N',N'-tetramethyluronium hexafluorophosphate (642 mg, 1.7 mmol) in DMF. The reaction mixture was shaken for 12 h, then the resin was filtered and rinsed with DMF (3×15 mL), methanol (3×15 mL), and dichloromethane (3×15 mL). The resin was soaked in 75% TFA (11 mL) in $CH_2Cl_2$ (4 mL) for 6 h. The resin was washed with $CH_2Cl_2$ and the combined filtrate was collected, concentrated in vacuo and purified by preparative LC/MS to afford 54 mg of the title compound (115). $^1$H-NMR (400 MHz, $CD_3OD$): 7.16 (m, 3H), 4.71 (dd, J=4.4, 7.2 Hz 1H), 4.16 (dd, J=3.6, 9.6 Hz, 1H), 3.29–3.24 (dd, J=4.8, 17.2 Hz 1H), 3.17–3.11 (dd, J=7.6, 17.6 Hz, 1H), 3.06–2.95 (m, 2H), 2.77–2.70 (dd, J=9.6, 16.8 Hz 1H), 1.19 (d, J=6.4 Hz, 12H): MS (ESI) m/z 408.67 (M+H$^+$).

Example 11

H-Arg-Asp(OPropofol)-OH (116)

Following procedures for preparation of compound (115), and substituting Boc-Arg(Mtr)-OH for Boc-Asn-OH, and in the final step soaking the resin in 95% TFA (14 mL) and dichloromethane (0.8 mL) for 12 h, provided the title compound (116). MS (ESI) m/z 451.50 (M+H$^+$).

Example 12

H-Asp-Asp(OPropofol)-OH (117)

Following procedures for preparation of compound (115), and substituting Boc-Asp(O$^t$Bu)-OH for Boc-Asn-OH, provided the title compound (117). MS (ESI) m/z 409.31 (M+H$^+$).

Example 13

H-Cys-Asp(OPropofol)-OH (118)

Following procedures for preparation of compound (115), and substituting Boc-Cys(STrt)-OH for Boc-Asn-OH, and in the final step soaking the resin in 95% TFA (14 mL), dichloromethane (0.5 mL) and 1% triisopropylsilane (0.5 mL) for 6 h provided the title compound (118). MS (ESI) m/z 397.39 (M+H$^+$).

Example 14

H-Leu-Asp(OPropofol)-OH (119)

Following procedures for preparation of compound (115), and substituting Boc-Leu-OH for Boc-Asn-OH, provided the title compound (119). MS (ESI) m/z 407.39 (M+H$^+$).

Example 15

H-Lys-Asp(OPropofol)-OH (120)

Following procedures for preparation of compound (115), and substituting α-N-Boc-ε-N-Boc-Lys-OH for Boc-Asn-OH, provided the title compound (120). MS (ESI) m/z 422.61 (M+H$^+$).

Example 16

H-Met-Asp(OPropofol)-OH (121)

Following procedures for preparation of compound (115), and substituting Boc-Met-OH for Boc-Asn-OH, provided the title compound (121). MS (ESI) m/z 425.14 (M+H$^+$).

Example 17

H-Tyr-Asp(OPropofol)-OH (122)

Following procedures for preparation of compound (115), and substituting Boc-Tyr(O$^t$Bu)-OH for Boc-Asn-OH, provided the title compound (122). MS (ESI) m/z 457.33 (M+H$^+$).

Example 18

H-Ala-Glu(OPropofol)-OH (123)

Following procedures for preparation of compound (107), and substituting compound (105) for compound (102) provided the title compound (123). $^1$H-NMR (400 MHz, $CD_3OD$): δ 7.16 (m, 3H), 4.35 (dd, J=5.2, 7.6 Hz 1H), 3.96 (q, J=7.2, 1H), 2.94–2.87 (m, 2H), 2.75 (m, 2H), 2.33 (m, 1H), 2.18 (m, 1H), 1.53 (d, J=6.8 Hz 3H), 1.18 (d, J=7.2 Hz, 12H). MS (ESI) m/z 379.34 (M+H$^+$).

Example 19

H-Asn-Glu(OPropofol)-OH (124)

Following procedures for preparation of compound (123), and substituting CBz-Asn-OH for CBz-Ala-OH provided the title compound (124). $^1$H-NMR (400 MHz, $CD_3OD$): δ 7.16 (m, 3H), 4.38 (dd, J=7.6, 5.2 Hz 1H), 4.23 (dd, J=9.2, 3.6 Hz, 1H), 3.00 (dd, J=16.8, 3.6 Hz, 1H), 2.91 (m, 2H), 2.77 (m, 3H), 2.33 (m, 1H), 2.16 (m, 1H), 1.18 (d, J=6.8 Hz, 12H). MS (ESI) m/z 422.35 (M+H$^+$). MS (ESI) m/z 422.35 (M+H$^+$).

Example 20

H-Leu-Glu(OPropofol)-OH (125)

Following procedures for preparation of compound (123) and substituting CBz-Leu-OH for CBz-Ala-OH provided the title compound (125). $^1$H-NMR (400 MHz, $CD_3OD$): δ 7.16 (m, 3H), 4.35 (t, J=7.2 Hz, 1H), 3.93 (dd, J=8.4, 5.6 Hz, H), 2.91 (m, 2H), 2.75 (m, 2H), 2.32 (m, 1H), 2.15 (m, 1H), 1.83–1.58 (m, 3H), 1.18 (d, J=6.8 Hz, 12H), 0.98 (m, 6H). MS (ESI) m/z 421.40 (M+H$^+$).

Example 21

H-Asp(OPropofol)-Val-OH (126)

To a homogeneous solution of compound (103), (874 mg, 2.2 mmol) in acetonitrile (5 mL) was added dicyclohexylcarbodiimide (550 mg, 2.7 mmol). N-hydroxysuccinimide (358 mg, 3.1 mmol) was then added and the reaction was allowed to proceed for 6 h. The resulting dicyclohexylurea was filtered and to the filtrate was added H-Val-O$^t$Bu hydrochloride (499 mg, 2.2 mmol). Triethylamine (5 mL) was added and after stirring for 6 h the solution was extracted with ethyl acetate (100 mL), washed with 10% citric acid (2×25 mL), saturated sodium bicarbonate (2×25 mL) and brine (2×25 mL). The organic layer was dried over $Na_2SO_4$ and then concentrated in vacuo. The crude compound was purified by chromatography on silica gel (Biotage), eluting with a gradient of hexane to 10% EtOAc/hexane) then the eluant concentrated in vacuo. The product was then treated with 30% TFA (24 mL) in dichloromethane (51 mL) for 45 min, concentrated in vacuo and the residue purified by preparative LC/MS to afford the title compound (126) (72 mg, 8% yield). $^1$H-NMR (400 MHz, $CD_3OD$): 7.19 (m, 3H), 4.34 (d, J=5.2 Hz 1H), 4.28 (m, 1H), 3.54–3.34 (m, 1H), 3.23–3.16 (dd, J=8.8, 18.4 Hz, 1H), 2.95 (m, 2H), 2.25 (m, 1H), 1.21 (d, J=6.8 Hz, 12H), 1.04 (dd, J=6.4, 9.6 Hz, 6H). MS (ESI) m/z 393.35 (M+H$^+$).

Example 22

H-Asp(OPropofol)-Ile-OH (127)

L-Isoleucine-O-Trityl resin was prepared following the protocol outlined in Example 9, substituting Fmoc-Ile for Fmoc-Asp(OPropofol)-OH. The isoleucine-loaded resin (500 mg, loading 1.3 mmol/g) and compound (103) (1.3 mmol) was suspended in DMF (8 mL) and diisopropylethylamine (0.68 mL, 3.9 mmol) and O-(1H-Benzotriazol-1-yl) N,N,N',N'-tetramethyluronium hexafluorophosphate (493 mg, 1.3 mmol) was added. The reaction mixture was shaken for 12 h after which the resin was filtered and rinsed with DMF (3×15 mL), methanol (3×15 mL), and dichloromethane (3×15 mL). The resin was then soaked in 75% TFA (11 mL) in $CH_2Cl_2$ (4 mL) for 6 h. The resin was washed with $CH_2Cl_2$ and the combined filtrate was collected, concentrated in vacuo and purified by preparative LC/MS to afford the title compound (127) (32 mg, 12% yield). $^1$H-NMR (400 MHz, $CD_3OD$): 7.18 (m, 3H), 4.34 (d, J=5.2, 1H), 4.20 (dd, J=3.6, 8.8 Hz, 1H), 3.46 (dd, J=4.0, 18.4 Hz 1H), 3.19–3.12 (dd, J=8.8, 18 Hz, 1H), 2.96 (m, 2H), 2.00–1.91 (m, 1H), 1.63–1.53 (m, 1H), 1.20 (m, 1H), 1.2 (d, J=6.8 Hz, 12H), 0.98 (d, J=9.2 Hz, 3H), 0.95 (t, J=7.2 Hz, 3H). MS (ESI) m/z 407.36 (M+H$^+$).

Example 23

H-Asp(OPropofol)-Ala-OH (128)

Following procedures for the preparation of compound (127) and substituting Ala-O-Trityl resin for Isoleucine-O-Trityl resin provided the title compound (128). MS (ESI) m/z 365.32 (M+H$^+$).

Example 24

H-Asp(OPropofol)-Asp-OH (129)

Following procedures for the preparation of compound (127) and substituting Asp(O$^t$Bu)-O-Trityl resin for Isoleucine-O-Trityl resin provided the title compound (129). MS (ESI) m/z 409.26 (M+H$^+$).

Example 25

H-Asp(OPropofol)-Gln-OH (130)

Following procedures for the preparation of compound (127) and substituting Gln-O-Trityl resin for Isoleucine-O-Trityl resin provided the title compound (130). MS (ESI) m/z 422.32 (M+H$^+$).

Example 26

H-Asp(OPropofol)-Glu-OH (131)

Following procedures for the preparation of compound (127) and substituting Glu(O-$^t$Bu)-O-Trityl resin for Isoleucine-O-Trityl resin provided the title compound (131). MS (ESI) m/z 423.28 (M+H$^+$).

Example 27

H-Asp(OPropofol)-Gly-OH (132)

Following procedures for the preparation of compound (127) and substituting Gly-O-Trityl resin for Isoleucine-O-Trityl resin provided the title compound (132). MS (ESI) m/z 351.30 (M+H$^+$).

Example 28

H-Asp(OPropofol)-Leu-OH (133)

Following procedures for the preparation of compound (127) and substituting Leu-O-Trityl resin for Isoleucine-O-Trityl resin provided the title compound (133). MS (ESI) m/z 407.36 (M+H$^+$).

Example 29

H-Asp(OPropofol)-Met-OH (134)

Following procedures for the preparation of compound (127) and substituting Met-O-Trityl resin for Isoleucine-O-Trityl resin provided the title compound (134). MS (ESI) m/z 425.31 (M+H$^+$).

Example 30

H-Asp(OPropofol)-Phe-OH (135)

Following procedures for the preparation of compound (127) and substituting Phe-O-Trityl resin for Isoleucine-O-Trityl resin provided the title compound (135). MS (ESI) m/z 441.32 (M+H$^+$).

Example 31

H-Asp(OPropofol)-Pro-OH (136)

Following procedures for the preparation of compound (127) and substituting Pro-O-Trityl resin for Isoleucine-O-Trityl resin provided the title compound (136). MS (ESI) m/z 391.31 (M+H$^+$).

Example 32

H-Asp(OPropofol)-Ser-OH (137)

Following procedures for the preparation of compound (127) and substituting Ser(O$^t$Bu)—O-Trityl resin for Isoleucine-O-Trityl resin provided the title compound (137). MS (ESI) m/z 381.29 (M+H$^+$).

Example 33

H-Glu(OPropofol)-Ala-OH (138)

Alanine-O-Trityl resin was prepared following the protocol outlined in Example 9, substituting Fmoc-Ala for Fmoc-Asp(OPropofol)-OH. The alanine-loaded resin (1.5 g, loading 0.5 mmol/g) and compound (106) (1.4 mmol) was suspended in DMF (15 mL) then diisopropylethylamine (0.73 mL, 4.2 mmol) and O-(1H-Benzotriazol-1-yl)N,N,N′,N′-tetramethyluronium hexafluorophosphate (531 mg, 1.4 mmol) was added. The reaction mixture was shaken for 12 h after which the resin was filtered and rinsed with DMF (3×15 mL), methanol (3×15 mL), and dichloromethane (3×15 mL). The resin was then soaked in 75% TFA (11 mL) in $CH_2Cl_2$ (4 mL) for 6 h. The resin was washed with $CH_2Cl_2$ and the combined filtrate was collected, concentrated in vacuo and purified by preparative LC/MS to afford the title compound (138) (30 mg, 10% yield). $^1$H-NMR (400 MHz, $CD_3OD$): 7.17 (m, 3H), 4.31 (q, J=2.8 Hz, 11H), 3.95 (t, J=6.4 Hz, 1H), 2.94 (m, 4H), 2.29 (m, 2H), 1.43 (d, J=7.6 Hz, 3H), 1.18 (d, J=6.4 Hz, 12H). MS (ESI) m/z 379.34 ($M+H^+$).

Example 34

H-Glu(OPropofol)-Arg-OH (139)

Following procedures for the preparation of compound (138) and substituting Arg(Mtr)-O-Trityl resin for Ala-O-Trityl resin, and in the final step soaking the resin in 95% TFA (14 mL) and dichloromethane (0.8 mL) for 12 h, provided the title compound (139). $^1$H-NMR (400 MHz, $CD_3OD$): 7.17 (m, 3H), 4.29 (t, J=7.2 Hz, 1H), 3.80 (t, J=6.8 Hz, 1H), 3.22 (t, J=6.8 Hz, 2H), 2.89 (m, 4H), 2.26 (m, 1H), 2.18 (m, 1H), 1.89 (m, 1H), 1.79 (m, 1H), 1.69 (m, 2H), 1.18 (d, J=6.8 Hz, 12H). MS (ESI) m/z 464.34 ($M+H^+$).

Example 35

H-Glu(OPropofol)-Asp-OH (140)

Following procedures for the preparation of compound (138) and substituting Asp(O$^t$Bu)—O-Trityl resin for Ala-O-Trityl resin provided the title compound (140). $^1$H-NMR (400 MHz, $CD_3OD$): 7.17 (m, 3H), 4.65 (dd, J=7.2, 5.2 Hz, 1H), 3.97 (t, J=6.4 Hz, 1H), 2.95 (m, 5H), 2.82 (dd, J=16, 7.2 Hz, 1H), 2.30 (q, J=12 Hz, 2H), 1.19 (d, J=6.8 Hz, 12H). MS (ESI) m/z 423.31 ($M+H^+$).

Example 36

H-Glu(OPropofol)-Gln-OH (141)

Following procedures for the preparation of compound (138) and substituting Asn-O-Trityl resin for Ala-O-Trityl resin provided the title compound (141). $^1$H-NMR (400 MHz, $CD_3OD$): 7.17 (m, 3H), 4.29 (t, J=6.4 Hz, 1H), 3.94 (m, 1H), 2.92 (m, 4H), 2.29 (q, J=7.6 Hz, 4H), 2.18 (m, 1H), 2.03 (m, 1H), 1.18 (d, J=6.4 Hz, 12H). MS (ESI) m/z 436.30 ($M+H^+$).

Example 37

H-Glu(OPropofol)-Glu-OH (142)

Following procedures for the preparation of compound (138) and substituting Glu(O$^t$Bu)—O-Trityl resin for Ala-O-Trityl resin provided the title compound (142). $^1$H-NMR (400 MHz, $CD_3OD$): 7.17 (m, 3H), 4.65 (dd, J=8.4, 5.2 Hz, 1H), 4.29 (t, J=6.4 Hz, 1H), 2.93 (m, 4H), 2.40 (m, 2H), 2.30 (m, 3H), 2.03 (m, 1H), 1.18 (d, J=6.4 Hz, 12H). MS (ESI) m/z 437.30 ($M+H^+$).

Example 38

H-Glu(OPropofol)-Gly-OH (143)

Following procedures for the preparation of compound (138) and substituting Gly-O-Trityl resin for Ala-O-Trityl resin provided the title compound (143). $^1$H-NMR(400 MHz, $CD_3OD$): 7.17 (m, 3H), 3.97 (m, 2H), 3.71 (ABq, J=108 Hz, 17.2 Hz, 1H), 2.89 (m, 4H), 2.27 (m, 2H), 1.19 (d, J=6.8 Hz, 12H). MS (ESI) m/z 365.34 ($M+H^+$).

Example 39

H-Glu(OPropofol)-Ile-OH (144)

Following procedures for the preparation of compound (138) and substituting Ile-O-Trityl resin for Ala-O-Trityl resin provided the title compound (144). $^1$H-NMR (400 MHz, $CD_3OD$): 7.17 (m, 3H), 4.32 (d, J=4.8 Hz, 1H), 3.94 (t, J=6.0 Hz, 1H), 2.91 (m, 4H), 2.27 (m, 2H), 1.95 (m, 1H), 1.58 (m, 1H), 1.18 (d, J=6.8 Hz, 13H), 0.97 (m, 6H). MS (ESI) m/z 421.35 ($M+H^+$).

Example 40

H-Glu(OPropofol)-Leu-OH (145)

Following procedures for the preparation of compound (138) and substituting Leu-O-Trityl resin for Ala-O-Trityl resin provided the title compound (145). $^1$H-NMR (400 MHz, $CD_3OD$): 7.17 (m, 3H), 4.38 (dd, J=10.4, 4.8 Hz, 1H), 3.91 (t, J=6.4 Hz, 1H), 2.92 (m, 4H), 2.81 (m, 2H), 1.70 (m, 3H), 1.18 (d, J=6.8 Hz, 13H), 0.97 (dd, J=6.4, 4.4 Hz, 6H). MS (ESI) m/z 421.35 ($M+H^+$).

Example 41

H-Glu(OPropofol)-Lys-OH (146)

Following procedures for the preparation of compound (138) and substituting Lys(ε—N-Boc)-O-Trityl resin for Ala-O-Trityl resin provided the title compound (146). $^1$H-NMR (400 MHz, $CD_3OD$): 7.17 (m, 3H), 4.65 (t, J=7.2 Hz, 1H), 3.86 (t, J=6.4 Hz, 1H), 2.92 (m, 6H), 2.27 (m, 2H), 1.88 (m, 1H), 1.74 (m, 3H), 1.48 (m, 2H), 1.18 (d, J=6.4 Hz, 12H). MS (ESI) m/z 436.39 ($M+H^+$).

Example 42

H-Glu(OPropofol)-Met-OH (147)

Following procedures for the preparation of compound (138) and substituting Met-O-Trityl resin for Ala-O-Trityl resin provided the title compound (147). $^1$H-NMR (400 MHz, $CD_3OD$): 7.16 (m, 3H), 4.40 (dd, J=7.6, 4.0 Hz, 1H), 3.94 (t, J=6.4 Hz, 1H), 2.92 (m, 4H), 2.56 (m, 2H), 2.29 (m, 2H), 2.18 (m, 1H), 2.09 (s, 3H), 2.01 (m, 11H), 1.18 (d, J=6.4 Hz, 12H). MS (ESI) m/z 439.30 (M+H$^+$).

Example 43

H-Glu(OPropofol)-Phe-OH (148)

Following procedures for the preparation of compound (138) and substituting Phe-O-Trityl resin for Ala-O-Trityl resin provided the title compound (148). $^1$H-NMR (400 MHz, CD$_3$OD): 7.26 (m, 4H), 7.17 (m, 3H), 4.55 (dd, J=9.2, 4.8 Hz, 1H), 3.82 (t, J=6.0 Hz, 1H), 3.28–3.00 (dd, 2H), 2.89 (m, 2H), 2.82 (m, 2H), 2.22 (m, 2H), 2.09 (s, 3H), 2.01 (m, 1H), 1.18 (d, J=6.8 Hz, 12H). MS (ESI) m/z 455.35 (M+H$^+$).

Example 44

H-Glu(OPropofol)-Ser-OH (149)

Following procedures for the preparation of compound (138) and substituting Ser(O$^t$Bu)-O-Trityl resin for Ala-O-Trityl resin provided the title compound (149). (400 MHz, CD$_3$OD): 7.17 (m, 3H), 4.39 (t, J=5.6 Hz, 1H), 4.00 (t, J=5.6 Hz, 1H), 3.89 (m, 2H), 2.30 (m, 2H), 1.18 (d, J=6.8 Hz, 12H). MS (ESI) m/z 395.51 (M+H$^+$).

Example 45

H-Glu(OPropofol)-Val-OH (150)

Following procedures for the preparation of compound (138) and substituting Val-O-Trityl resin for Ala-O-Trityl resin provided the title compound (150). (400 MHz, CD$_3$OD): 7.17 (m, 3H), 4.28 (d, J=5.2 Hz, 1H), 3.98 (t, J=6.4 Hz, 1H), 2.92 (m, 4H), 2.28 (m, 3H), 1.18 (d, J=6.4 Hz, 12H), 1.00 (dd, J=11.6, 6.4 Hz, 6H). MS (ESI) m/z 407.52 (M+H$^+$).

Example 46

H-Val-OPropofol (151)

To homogeneous solution of Boc-Valine-OH (234 mg, 1.1 mmol) in toluene (5 mL) was added DCC (333 mg, 1.6 mmol). DMAP (11 mg, 0.1 mmol) and propofol (199 µL, 1.1 mmol) and the reaction mixture was allowed to stir until the solution became homogeneous. It was then placed in a 60° C. oil bath and allowed to stir for a further 8 h. The reaction mixture was then cooled to room temperature, the dicyclohexylurea was filtered off and the solution was diluted with ether (100 mL). The ether layer was washed with 10% citric acid (2×25 mL), saturated sodium bicarbonate (2×25 mL), and brine (2×25 mL). The organic layer was dried over Na$_2$SO$_4$ and then concentrated in vacuo. The crude compound was purified by radial chromatography on silica gel, eluting with a gradient of hexane to 50% ethyl acetate/hexane. The resulting residue was treated with 20% TFA (4 mL) in dichloromethane (16 mL) at room temperature for 30 min. After removing the solvent, the resulting residue was purified by preparative LC/MS to afford the title compound (151) (60 mg, 20% yield). $^1$H-NMR (400 MHz, CD$_3$OD): δ 7.24 (m, 3H), 4.46 (d, J=3.2 Hz, 1H), 2.92 (m, 2H), 2.68 (m, 1H), 1.27 (d, J=7.6 Hz, 3H), 1.21–1.19 (d, J=6.8 Hz, 15H). MS (ESI) m/z 278.30 (M+H$^+$).

Example 47

H-Ala-OPropofol Hydrochloride (152)

Following procedures for the preparation of compound (151) and substituting Boc-Ala-OH for Boc-Val-OH. The hydrochloride salts were prepared by treating the desired compound with a solution of 1 N HCl aqueous solution to provide the title compound (152). $^1$H-NMR (400 MHz, CD$_3$OD): δ 7.19–7.27 (m, 3H), 4.57 (q, J=7.2 Hz, 1H), 2.92 (m, 2H), 1.81 (d, J=7.2 Hz, 3H), 1.21 (d, J=6.8 Hz, 12H). MS (ESI) m/z 252.44 (M+H$^+$).

Example 48

H-Asn-OPropofol Hydrochloride (153)

Following procedures for the preparation of compound (151) and substituting Boc-Asn(Trt)-OH for Boc-Val-OH provided the crude product. After purification the residue was treated with 90% TFA (45 mL) in dichloromethane (4.5 mL) and 1% triisopropylsilane (0.5 mL) for 4 h. After removal of the solvent the resulting residue was purified by preparative LC/MS and treated with one molar equivalent of 1 N HCl aqueous solution to afford the title compound (153). $^1$H-NMR (400 MHz, CD$_3$OD): δ 7.23–7.19 (m, 3H), 4.73–4.71 (m, 1H), 3.23–3.17 (m, 2H), 2.94 (m, 2H), 1.19 (d, J=6.4 Hz, 12H). MS (ESI) m/z 294.34 (M+H$^+$).

Example 49

H-His-OPropofol (154)

Following procedures for the preparation of compound (151) and substituting Boc-His(Boc)-OH for Boc-Val-OH provided the title compound (154). $^1$H-NMR (400 MHz, CD$_3$OD): δ 8.98 (s, 1H), 7.64 (s, 1H), 7.28–7.20 (m, 3H), 5.02–4.99 (dd, J=9.6, 5.6 Hz, 1H), 3.86–3.81 (m, 1H), 3.59–3.53 (dd, J=16.0, 9.6 Hz, 1H), 2.95 (m, 1H), 2.78 (m, 1H), 1.19 (d, J=6.4 Hz, 12H). MS (ESI) m/z 317.33 (M+H$^+$)

Example 50

H-Lys-OPropofol Hydrochloride (155)

Following procedures for the preparation of compound (151) and substituting α-N-Boc-Lys(ε-N-Boc)-OH for Boc-Val-OH. After LC/MS purification, the residue was treated with two molar equivalent of 1 N HCl aqueous solution to provide the title compound (155). $^1$H-NMR (400 MHz, CD$_3$OD): δ 7.20–7.28 (m, 3H), 4.52 (t, J=6.0 Hz, 1H), 3.01–2.89 (m, 4H), 2.35–2.29 (m, 1H), 2.16–2.09 (m, 1H), 1.81–1.67 (m, 4H), 1.21–1.20 (d, J=6.8 Hz, 12H). MS (ESI) m/z 307.36 (M+H$^+$).

Example 51

H-Met-OPropofol (156)

Following procedures for the preparation of compound (151) and substituting Boc-Met-OH for Boc-Val-OH provided the title compound (156). MS (ESI) m/z 310.22 (M+H$^+$).

Example 52

H-Phe-OPropofol (157)

Following procedures for the preparation of compound (151) and substituting Boc-Phe-OH for Boc-Val-OH provided the title compound (157). $^1$H-NMR (400 MHz, CD$_3$OD): δ 7.43–7.33 (m, 5H), 7.21 (m, 3H), 4.74 (dd, J=8.8, 6.0 Hz, 1H), 3.62 (dd, J=14, 6.0 Hz, 1H), 3.22 (dd, J=14.4, 9.2 Hz, 1H), 2.86 (m, 2H), 1.18 (d, J=6.8 Hz, 12H). MS (ESI) m/z 326.25 (M+H$^+$). MS (ESI) m/z 326.25 (M+H$^+$).

Example 53

H-Ser-OPropofol (158)

Following procedures for the preparation of compound (151) and substituting Boc-Ser(O$^t$Bu)-OH for Boc-Val-OH provided the title compound (158). $^1$H-NMR (400 MHz, CD$_3$OD): δ 7.21–7.17 (m, 3H), 4.39 (t, J=2.8 Hz, 1H), 4.16–3.84 (ABq, J=10, 3.2 Hz, 2H), 1.19 (d, J=7.2 Hz, 12H). MS (ESI) m/z 266.33 (M+H$^+$).

Example 54

H-Asp(OPropofol)-OH (159)

To a flask containing 500 mg of 10% Pd—C was added a solution of compound (102) in methanol under nitrogen. The resulting mixture was degassed three times, after which hydrogen was introduced via a balloon apparatus. The suspended mixture was allowed to stir vigorously for 4 h. The reaction mixture was filtered through a pad of celite and concentrated in vacuo to arrive at the title compound (159). MS (ESI) m/z 294.36 (M+H$^+$).

Example 55

H-Glu(OPropofol)-OH (160)

To a flask containing 500 mg of 10% Pd—C was added a solution of compound (105) in methanol under nitrogen. The resulting mixture was degassed three times, after which hydrogen was introduced via a balloon apparatus. The suspended mixture was allowed to stir vigorously for 4 h. The reaction mixture was filtered through a pad of celite and concentrated in vacuo to arrive at the title compound (160). MS (ESI) m/z 308.39 (M+H$^+$).

Example 56

H-Ala-Ser(β-OC(O)OPropofol)-OH (161)

Step A: Boc-Ala-Ser-O$^t$Bu (162)

To a solution of L-Boc-alanine (567 mg, 3 mmol) and L-serine α-t-butyl ester in DMF (6 mL) was added diisopropylethylamine (1 mL, 6.2 mmol) followed by O-(7-azabenzotriazol-1-yl)-N,N, N',N'-tetramethyluronium hexafluoro-phosphate (591 mg, 3 mmol). The resulting mixture was stirred at room temperature for 14 h and then diluted with 40 mL of ethyl acetate. The organic solution was washed with 10% aqueous citric acid solution (2×30 mL), saturated aqueous sodium bicarbonate solution (2×30 mL) and brine (2×30 mL). The organic layer was dried over magnesium sulfate and then concentrated in vacuo. The crude compound (162) was used without further purification.

Step B: 2,6-Bis(isopropyl)phenoxycarbonyl chloride (163)

Phosgene (13 mL, 20% in toluene) was added to propofol (3.6 g, 20 mmol) under a nitrogen atmosphere. The mixture was cooled to 0° C. and N,N-dimethylaniline (3.3 mL, 26 mmol) was added dropwise. The reaction mixture was allowed to warm to room temperature slowly and stirred for 14 h. The solvent was removed in vacuo. The crude product was carried to next step without further purification.

Step C: Boc-Ala-Ser(β-OC(O)OPropofol)-O$^t$Bu (164)

To an ice cold solution of chloroformate (163) (720 mg, 3 mmol) in dichloromethane (10 mL) was added triethylamine (0.35 mL, 6 mmol) followed by compound (162). The resulting mixture was allowed to warm to room temperature and stirred for 12 h. The mixture was diluted with ethyl acetate (30 mL) and washed with 10% aqueous citric acid solution (2×30 mL), dried over MgSO$_4$, filtered and concentrated in vacuo. The crude product (164) was used in the next step without purification.

Step D: H-Ala-Ser(β-OC(O)OPropofol)-OH (161)

The crude compound (164) from above was dissolved in dichloromethane (2 mL) and treated with trifluoroacetic acid (1 mL). The resulting mixture was stirred at room temperature for 3 h. The solvent was removed in vacuo and the crude residue was purified by reverse phase LC/MS to afford 25 mg of the title compound (161). $^1$H-NMR (400 MHz, CD$_3$OD): δ 7.12–7.20 (m, 3H), 4.59 (br. s, 3H), 3.99 (q, J=7.2 Hz, 2H), 2.99 (m, 2H), 1.56 (d, J=6.8 Hz, 3H), 1.18 (d, J=7.2 Hz, 12H). MS (ESI) m/z 381.31 (M+H$^+$).

Example 57

H-Tyr-OPropofol Hydrochloride (165)

Following procedures for the preparation of compound (151) and substituting Boc-Tyr-OH for Boc-Val-OH; after LC/MS purification, the residue was treated with one molar equivalent of 1 N HCl aqueous solution to provide the title compound (165). $^1$H-NMR (400 MHz, CD$_3$OD): δ 7.26–7.18 (m, 5H), 6.83–6.81 (dd, J=9.2, 2.8 Hz, 2H), 4.75–4.71 (dd, J=9.2, 5.2 Hz, 1H), 3.59–3.54 (dd, J=14.4, 5.6 Hz, 1H), 3.16–3.10 (dd, J=14.4, 9.2 Hz, 1H), 2.85 (m, 2H), 1.18 (d, J=6.8 Hz, 12H). MS (ESI) m/z 343.43 (M+H$^+$).

Example 58

H-Gln-OPropofol Hydrochloride (166)

Following procedures for the preparation of compound (151) and substituting Boc-Tyr-OH for Boc-Gln(tBu)-OH; after LC/MS purification, the residue was treated with one molar equivalent of 1 N HCl aqueous solution to provide the title compound (166). $^1$H-NMR (400 MHz, CD$_3$OD): δ 7.26–7.19 (m, 3H), 4.58–4.55 (dd, J=7.6, 5.2 Hz, 1H), 2.89 (s, 2H), 2.68 (m, 2H), 2.56–2.52 (m, 2H), 2.32–2.27 (m, 2H), 1.21 (t, J=6.8 Hz, 12H). MS (ESI) m/z 308.34 (M+H$^+$).

Example 59

H-Gly-OPropofol Hydrochloride (167)

Following procedures for the preparation of compound (151) and substituting Boc-Tyr-OH for Boc-Gly-OH; after LC/MS purification, the residue was treated with one molar equivalent of 1 N HCl aqueous solution to provide the title compound (167). $^1$H-NMR (400 MHz, CD$_3$OD): δ 7.25–7.19 (m, 3H), 4.27 (s, 2H), 2.95–2.92 (m, 2H), 1.19 (d, J=6.8 Hz, 12H). MS (ESI) m/z 237.33 (M+H$^+$).

Example 60

H-Thr-OPropofol Hydrochloride (168)

Following procedures for the preparation of compound (151) and substituting Boc-Tyr-OH for Boc-Thr(O$^t$Bu)-OH; after LC/MS purification, the residue was treated with one molar equivalent of 1 N HCl aqueous solution to provide the title compound (168). $^1$H-NMR (400 MHz, CD$_3$OD): δ 7.25–7.19 (m, 3H), 4.71–4.69 (dd, J=7.6, 5.2 Hz, 1H), 4.44 (d, J=2.8 Hz, 1H), 3.14 (m, 1H), 2.94 (m, 1H), 1.46 (d, J=6.8 Hz, 3H), 1.19 (d, J=6.8 Hz, 12H). MS (ESI) m/z 281.48 (M+H$^+$).

Example 61

H-Pro-OPropofol Hydrochloride (169)

Following procedures for the preparation of compound (151) and substituting Boc-Tyr-OH for Boc-Pro-OH; after LC/MS purification, the residue was treated with one molar equivalent of 1 N HCl aqueous solution to provide the title compound (169). $^1$H-NMR (400 MHz, CD$_3$OD): δ 7.28–7.21 (m, 3H), 4.85 (m, 1H), 3.52–3.39 (m, 2H), 2.91 (m, 2H), 2.73–2.70 (m, 1H), 2.39–2.34 (m, 1H), 2.26–2.16 (m, 2H), 1.21 (t, J=6.8 Hz, 12H). MS (ESI) m/z 277.42 (M+H$^+$).

Example 62

H-Val-Asn-OPropofol (170)

A solution of Boc-Val-OH (0.28 g, 1.28 mmol) in 4 mL of DMF was treated with O-Benzotriazol-1-yl-N,N,N',N'-tetramethyluronium hexafluorophosphate (0.5 g, 1.31 mmol) followed by diisopropylethylamine (0.5 mL, 2.9 mmol). The reaction mixture was stirred for 5 min, and then a solution of (153) in DMF (1 mL) was added. The resulting mixture was stirred at room temperature for 14 h. The mixture was then diluted with 10% aqueous citric acid solution (15 mL) and ethyl acetate (30 mL). The layers were separated and the organic layer was washed with saturated NaHCO$_3$ aqueous solution (15 mL) and brine (2×15 mL), dried over MgSO$_4$ and concentrated in vacuo. The crude product was purified by chromatography on silica gel (Biotage), eluting with a gradient of hexane to 60% ethyl acetate/hexane. The solvent was removed in vacuo, the residue dissolved in anhydrous dichloromethane (5 mL) and treated with trifluoroacetic acid (1 mL). The mixture was stirred at room temperature for 2 h, concentrated in vacuo and purified by preparative LC/MS to afford the title compound (170) (267 mg, 53% yield). $^1$H-NMR (400 MHz, CD$_3$OD): δ 7.22–7.14 (m, 3H), 5.16 (t, J=6.4 Hz, 1H), 3.58 (s, 1H), 3.03–2.96 (m, 4H), 2.14 (s, 1H), 1.17 (t, J=6.8 Hz, 12H), 1.04 (d, J=6.8 Hz, 3H), 1.00 (d, J=6.8 Hz, 3H). MS (ESI) m/z 408.37 (M+H$^+$).

Example 63

H-Gly-Asn-OPropofol (171)

Following procedures for preparation of H-Val-Asn-OPropofol, and substituting Boc-Val-OH with Boc-Gly-OH, provided the title compound (171). $^1$H-NMR (400 MHz, CD$_3$OD): δ 7.09–7.11 (m, 3H), 5.21 (m, 1H), 3.672 (m, 2H), 2.96–3.04 (m, 4H), 1.18 (d, J=7.2 Hz, 12H). MS (ESI) m/z 350.3 (M+H$^+$).

Example 64

H-Ala-Asn-OPropofol (172)

Following procedures for preparation of H-Val-Asn-OPropofol, and substituting Boc-Val-OH with Boc-Ala-OH, provided the title compound (172). $^1$H-NMR (400 MHz, CD$_3$OD): δ 7.09–7.11 (m, 3H), 5.21 (m, 1H), 3.98 (m, 1H), 2.96–3.04 (m, 4H), 1.48–1.5 (d, J=9.8 Hz, 3H), 1.18 (d, J=7.2 Hz, 12H). MS (ESI) m/z 364.5 (M+H$^+$).

Example 65

H-Gln-Asn-OPropofol (173)

Following procedures for preparation of H-Val-Asn-OPropofol, and substituting Boc-Val-OH with Boc-Gln-OH, provided the title compound (173). $^1$H-NMR (400 MHz, CD$_3$OD): δ 7.14–7.21 (m, 3H), 5.16–5.19 (m, 1H), 3.86–3.95 (m, 1H), 2.95–3.00 (m, 4H), 2.5 (m, 2H), 2.14 (m, 2H), 1.18 (d, J=7.2 Hz, 12H). MS (ESI) m/z 421.3 (M+H$^+$).

Example 66

H-Ser-Asn-OPropofol (174)

Following procedures for preparation of H-Val-Asn-OPropofol, and substituting Boc-Val-OH with Boc-Ser-OH, provided the title compound (174). $^1$H-NMR (400 MHz, CD$_3$OD): δ 7.14–7.21 (m, 3H), 5.16–5.19 (m, 1H), 3.9–3.94 (m, 2H), 3.86–3.89 (m, 1H), 2.95–3.00 (m, 4H), 1.18 (d, J=7.2 Hz, 12H). MS (ESI) m/z 380.3 (M+H$^+$).

Example 67

H-Dap-Asn-OPropofol (175)

Following procedures for preparation of H-Val-Asn-OPropofol, and substituting Boc-Val-OH with Boc-Dap(Boc)-OH, provided the title compound (175). $^1$H-NMR (400 MHz, CD$_3$OD): δ 7.20–7.14 (m, 3H), 5.16–5.12 (m, 1H), 3.73 (t, J=8.0 Hz, 1H), 3.27–3.23 (m, 1H), 3.08–2.94 (m, 5H), 1.18–1.14 (t, J=6.8 Hz, 12H). MS (ESI) m/z 379.39 (M+H$^+$).

Example 68

H-Asp-Asn-OPropofol (176)

Following procedures for preparation of H-Val-Asn-OPropofol, and substituting Boc-Val-OH with Boc-Asp(O$^t$Bu)-OH, provided the title compound (176). $^1$H-NMR (400 MHz, CD$_3$OD): δ 7.19–7.14 (m, 3H), 5.19 (dd, J=8, 4.8 Hz, 1H), 4.14 (dd, J=9.6, 4 Hz, 1H), 3.04–2.89 (m, 4H), 2.81–2.75 (dd, J=16.8, 2.4 Hz, 1H), 2.59–2.52 (dd, J=14.4, 8.4 Hz, 1H), 1.18 (d, J=6.8 Hz, 6H), 1.16 (d, J=6.8 Hz, 6H). MS (ESI) m/z 408.37 (M+H⁺).

Example 69

H-Tyr-Asn-OPropofol (177)

Following procedures for preparation of H-Val-Asn-OPropofol, and substituting Boc-Val-OH with Boc-Tyr-OH, provided the title compound (177). ¹H-NMR (400 MHz, CD₃OD): δ 7.22–7.15 (m, 3H), 7.10–7.08 (d, J=8.4 Hz, 2H), 6.70 (d, J=8.4 Hz, 2H), 5.18 (t, J=6.0 Hz, 1H), 3.97–3.94 (dd, J=8.4, 5.2 Hz, 1H), 3.18–3.13 (dd, J=14.4, 5.2 Hz, 1H), 3.03–2.98 (m, 4H), 2.88–2.82 (dd, J=16.8, 10 Hz, 1H), 1.18–1.15 (t, J=6.8 Hz, 12H). MS (ESI) m/z 456.64 (M+H⁺).

Example 70

H-Asp-Ala-OPropofol (178)

Following procedures for preparation of H-Val-Asn-OPropofol, substituting Boc-Val-OH with Boc-Asp(O$^t$Bu)-OH and compound (153) with (152), provided the title compound (178). ¹H-NMR (400 MHz, CD₃OD): δ 7.22–7.14 (m, 3H), 4.80–4.75 (q, J=7.2 Hz, 1H), 4.15–4.12 (m, 1H), 2.97–2.91 (m, 2H), 2.82–2.76 (dd, J=16.4, 3.6 Hz, 1H), 2.58–2.51 (dd, J=17.2, 10.4 Hz, 1H), 1.64 (d, J=7.6 Hz, 3H), 1.18 (d, J=6.4 Hz, 12H). MS (ESI) m/z 365.17 (M+H⁺).

Example 71

H-Val-Ala-OPropofol (179)

Following procedures for preparation of H-Val-Asn-OPropofol, substituting compound (153) with (152), provided the title compound (179). ¹H-NMR (400 MHz, CD₃OD): δ 7.22–7.14 (m, 3H), 4.83–4.78 (q, J=7.2 Hz, 1H), 3.66 (d, J=5.6 Hz, 1H), 3.04–2.94 (m, 2H), 2.22–2.18 (m, 1H), 1.64 (d, J=7.2 Hz, 3H), 1.17 (d, J=6.4 Hz, 12H), 1.08 (d, J=6.8 Hz, 3H), 1.05 (d, J=7.2 Hz, 3H). MS (ESI) m/z 349.18 (M+H⁺).

Example 72

H-Dap-Ala-OPropofol (180)

Following procedures for preparation of H-Val-Asn-OPropofol, substituting Boc-Val-OH with Boc-Dap(Boc)-OH and compound (153) with (152), provided the title compound (180). ¹H-NMR (400 MHz, CD₃OD): δ 7.22–7.14 (m, 3H), 4.80–4.75 (q, J=7.6 Hz, 1H), 3.81–3.77 (dd, J=8.4, 5.2 Hz, 1H), 3.27–3.22 (dd, J=13.2, 5.2 Hz, 1H), 3.05–3.00 (dd, J=13.2, 8.4 Hz, 1H), 3.02–2.91 (m, 2H), 1.67 (d, J=7.6 Hz, 3H), 1.18 (d, J=6.8 Hz, 12H). MS (ESI) m/z 336.30 (M+H⁺).

Example 73

H-Asp-Ser-OPropofol (181)

Following procedures for preparation of H-Val-Asn-OPropofol, substituting Boc-Val-OH with Boc-Asp(O$^t$Bu)-OH and compound (153) with (158), provided the title compound (181). ¹H-NMR (400 MHz, CD₃OD): δ 7.21–7.14 (m, 3H), 4.82–4.77 (m, 1H), 4.27–4.24 (dd, J=8.8, 4.0 Hz, 1H), 4.19–4.15 (dd, J=10.4, 4.8 Hz, 1H), 4.03–3.99 (dd, J=11.2, 4.0 Hz, 1H), 3.04–2.94 (m, 2H), 2.97–2.91 (dd, J=17.6, 4.8 Hz, 1H), 2.79–2.73 (dd, J=17.6, 9.2 Hz, 1H), 1.17 (m, 12H). MS (ESI) m/z 381.4 (M+H⁺).

Example 74

H-Val-Ser-OPropofol (182)

Following procedures for preparation of H-Val-Asn-OPropofol, substituting compound (153) with (158), provided the title compound (182) as the formate salt. ¹H-NMR (400 MHz, CD₃OD): δ 8.48 (s, 1H), 7.29–7.14 (m, 3H), 4.48 (m, 1H), 4.14–4.11 (m, 1H), 4.04–4.00 (m, 1H), 3.64 (t, J=5.2 Hz, 1H), 3.05–3.02 (m, 2H), 2.21 (m, 1H), 1.17 (m, 12H), 1.05 (m, 6H). MS (ESI) m/z 365.34 (M+H⁺).

Example 75

H-Ala-Tyr-OPropofol (183)

Following procedures for preparation of H-Val-Asn-OPropofol, substituting Boc-Val-OH with Boc-Ala-OH and compound (153) with (165), provided the title compound (183). ¹H-NMR (400 MHz, CD₃OD): δ 7.20–7.12 (m, 5H), 6.73 (d, J=7.6 Hz, 2H), 5.05–5.01 (dd, J=8.8, 6.4 Hz, 1H), 3.64 (m, 1H), 3.29–3.24 (m, 1H), 3.04–2.98 (dd, J=13.6, 9.2 Hz, 1H), 2.90 (m, 1H), 2.61 (m, 1H), 1.37 (d, J=6.8 Hz, 3H), 1.12 (m, 12H). MS (ESI) m/z 413.45 (M+H⁺).

Example 76

H-Glu-Tyr-OPropofol (184)

Following procedures for preparation of H-Val-Asn-OPropofol, substituting Boc-Val-OH with Boc-Glu(O$^t$Bu)-OH and compound (153) with (165), provided the title compound (184). ¹H-NMR (400 MHz, CD₃OD): δ 7.20–7.13 (m, 5H), 6.73 (d, J=8.0 Hz, 2H), 5.05–5.01 (dd, J=9.6, 6.0 Hz, 1H), 3.85–3.82 (dd, J=8.0, 4.4 Hz, 1H), 3.36–3.32 (m, 1H), 3.05–2.99 (dd, J=14.0, 9.6 Hz, 1H), 2.94 (m, 1H), 2.63 (m, 1H), 2.51–2.41 (m, 2H), 2.11–1.96 (m, 2H), 1.12 (m, 12H). MS (ESI) m/z 471.43 (M+H⁺).

Example 77

H-Dap-Tyr-OPropofol (185)

Following procedures for preparation of H-Val-Asn-OPropofol, substituting Boc-Val-OH with Boc-Dap(Boc)-OH and compound (153) with (165), provided the title compound (185) as the formate salt. ¹H-NMR (400 MHz, CD₃OD): δ 8.45 (s, 1H), 7.21–7.13 (m, 5H), 6.74 (d, J=8.4 Hz, 2H), 5.04–5.01 (dd, J=9.6, 6.0 Hz, 1H), 3.58–3.55 (dd, J=8.8, 5.2 Hz, 1H), 3.38–3.35 (m, 1H), 3.13–3.04 (m, 2H), 2.93 (m, 1H), 2.87–2.82 (dd, J=12.4, 8.4 Hz, 1H), 2.70 (m, 1H), 1.14 (m, 12H). MS (ESI) m/z 428.42 (M+H⁺).

Example 78

H-Ser-Tyr-OPropofol (186)

Following procedures for preparation of H-Val-Asn-OPropofol, substituting Boc-Val-OH with Boc-Ser-OH and compound (153) with (165), provided the title compound (186). ¹H-NMR (400 MHz, CD₃OD): δ 7.21–7.13 (m, 5H), 6.74 (d, J=8.4 Hz, 2H), 5.08–5.04 (dd, J=8.8, 6.8 Hz, 1H), 3.88–3.85 (dd, J=10.8, 4.0 Hz, 1H), 3.75–3.63 (m, 2H), 3.31–3.27 (m, 1H), 3.06–3.00 (dd, J=14.0, 9.2 Hz, 1H), 2.89 (m, 1H), 2.58 (m, 1H), 1.14 (m, 12H). MS (ESI) m/z 429.44 (M+H$^+$).

Example 79

H-Pro-Tyr-OPropofol (187)

Following procedures for preparation of H-Val-Asn-OPropofol, substituting Boc-Val-OH with Boc-Pro-OH and compound (153) with (165), provided the title compound (187). $^1$H-NMR (400 MHz, CD$_3$OD): δ 7.21–7.13 (m, 5H), 6.74 (d, J=8.4 Hz, 2H), 5.05–5.02 (dd, J=9.6, 6.0 Hz, 1H), 4.08–4.05 (dd, J=8.4, 4.8 Hz, 1H), 3.37–3.35 (m, 1H), 3.29–3.13 (m, 2H), 3.06–3.00 (dd, J=14.0, 9.6 Hz, 1H), 2.93 (m, 1H), 2.66 (m, 1H), 2.34 (m, 1H), 1.97–1.87 (m, 3H), 1.13 (m, 12H). MS (ESI) m/z 439.42 (M+H$^+$).

Example 80

H-Val-Tyr-OPropofol (188)

Following procedures for preparation of H-Val-Asn-OPropofol, substituting compound (153) with (165), provided the title compound (188) as the trifluoroacetate salt. $^1$H-NMR (400 MHz, CD$_3$OD): δ 7.18–7.13 (m, 5H), 6.74 (d, J=8.8 Hz, 2H), 5.11–5.07 (dd, J=9.6, 6.0 Hz, 1H), 3.67 (d, J=4.8 Hz, 1H), 3.37–3.32 (dd, J=14.0, 5.6 Hz, 1H), 3.06–3.00 (dd, J=14.0, 9.2 Hz, 1H), 2.93 (m, 1H), 2.66 (m, 1H), 2.24 (m, 1H), 1.09 (m, 15H), 1.02 (d, J=6.8 Hz, 3H). MS (ESI) m/z 442.39 (M+H$^+$).

Example 81

H-Asn-Tyr-OPropofol (189)

Following procedures for preparation of H-Val-Asn-OPropofol, substituting Boc-Val-OH with Boc-Asn-OH and compound (153) with (165), provided the title compound (189) as the trifluoroacetate salt. $^1$H-NMR (400 MHz, CD$_3$OD): δ 7.19–7.13 (m, 5H), 6.74 (d, J=8.0 Hz, 2H), 5.04–5.00 (dd, J=10.4, 5.6 Hz, 1H), 4.17–4.14 (dd, J=10.0, 4.0 Hz, 1H), 3.41–3.37 (dd, J=14.0, 5.2 Hz, 1H), 3.03–2.87 (m, 3H), 2.72–2.65 (m, 2H), 1.14 (m, 12H). MS (ESI) m/z 457.36 (M+H$^+$).

Example 82

H-Lys-Tyr-OPropofol (190)

Following procedures for preparation of H-Val-Asn-OPropofol, substituting Boc-Val-OH with Boc-Lys(Boc)-OH and compound (153) with (165), provided the title compound (190) as the trifluoroacetate salt. $^1$H-NMR (400 MHz, CD$_3$OD): δ 7.22–7.14 (m, 5H), 6.74 (d, J=8.8 Hz, 2H), 5.08–5.04 (dd, J=10.4, 5.2 Hz, 1H), 3.88–3.85 (dd, J=6.0, 4.8 Hz, 1H), 3.43–3.38 (dd, J=14.4, 5.2 Hz, 1H), 3.06–3.00 (dd, J=14.0, 10.0 Hz, 1H), 3.06–3.00 (m, 1H), 2.84–2.79 (t, J=7.6 Hz, 2H), 2.71 (m, 1H), 1.91–1.85 (q, J=8.0 Hz, 2H), 1.66–1.44 (m, 4H), 1.14 (d, J=7.2 Hz, 12H). MS (ESI) m/z 472.38 (M+H$^+$).

Example 83

H-Asp-Tyr-OPropofol (191)

Following procedures for preparation of H-Val-Asn-OPropofol, substituting Boc-Val-OH with Boc-Asp($^t$OBu)-OH and compound (153) with (165), provided the title compound (191) as the trifluoroacetate salt. $^1$H-NMR (400 MHz, CD$_3$OD): δ 7.20–7.13 (m, 5H), 6.74 (d, J=8.4 Hz, 2H), 5.03–4.99 (dd, J=9.6, 6.0 Hz, 1H), 4.07–4.03 (dd, J=10.0, 4.0 Hz, 1H), 3.35–3.30 (dd, J=13.6, 5.6 Hz, 1H), 3.03–2.97 (dd, J=14.0, 10.0 Hz, 1H), 2.92 (m, 1H), 2.80–2.75 (dd, J=16.8, 4.0 Hz, 1H), 2.63 (m, 1H), 2.56–2.49 (dd, J=17.2, 10.0 Hz, 1H), 1.12 (s, 12H). MS (ESI) m/z 458.31 (M+H$^+$).

Example 84

H-Gly-Tyr-OPropofol (192)

Following procedures for preparation of H-Val-Asn-OPropofol, substituting Boc-Val-OH with Boc-Gly-OH and compound (153) with (165), provided the title compound (192) as the trifluoroacetate salt. $^1$H-NMR (400 MHz, CD$_3$OD): δ 7.21–7.13 (m, 5H), 6.74 (d, J=8.4 Hz, 2H), 5.08–5.04 (dd, J=9.6, 5.6 Hz, 1H), 3.64 (dd, J=23.2, 16.0 Hz, 2H), 3.38–3.34 (dd, J=14.0, 5.6 Hz, 1H), 3.03–2.97 (dd, J=14.0, 9.6 Hz, 1H), 2.92 (m, 1H), 2.68 (m, 1H), 1.13 (m, 12H). MS (ESI) m/z 400.34 (M+H$^+$).

Example 85

H-Ala-Phe-OPropofol (193)

To a solution of (157) (332 mg, 1.0 mmol) and Boc-L-alanine (231 mg, 1.2 mmol) in DMF (4 mL) was added diisopropylethylamine (532 μL, 3.0 mmol) followed by O-(7-azabenzotriazol-1-yl)-N,N,N',N'-tetramethyluronium hexafluoro-phosphate (465 mg, 1.2 mmol). The resulting mixture was stirred at room temperature for 12 h and then diluted with 20 mL of ethyl acetate. The organic solution was washed with 10% aqueous citric acid solution (2×20 mL), saturated aqueous sodium bicarbonate solution (2×20 mL) and brine (2×20 mL). The organic layer was dried over magnesium sulfate and then concentrated in vacuo. The resulting residue was treated with 20% TFA (8 mL) in dichloromethane (32 mL) at room temperature for 30 min. After removing the solvent, the resulting residue was purified by preparative LC/MS to afford the title compound (193) (100 mg, 25% yield). $^1$H-NMR (400 MHz, CD$_3$OD): δ 7.37–7.15 (m, 8H), 5.13 (dd, J=9.6, 5.6 Hz, 1H), 3.80 (m, 1H), 3.46 (dd, J=14.0, 6.0 Hz, 1H), 3.15 (dd, J=16.8, 7.6 Hz, 1H), 1.46 (dd, J=7.2, 2.8 Hz, 1H), 1.13 (m, 12H). MS (ESI) m/z 397.37 (M+H$^+$).

Example 86

H-Arg-Phe-OPropofol (194)

Following procedures for the preparation of compound H-Ala-Phe-OPropofol and substituting Boc-Ala-OH with Tris-Boc-L-arginine provided the title compound (194). $^1$H-NMR (400 MHz, CD$_3$OD): δ 7.38–7.15 (m, 8H), 5.13 (dd, J=10.0, 4.8 Hz, 1H), 3.89 (t, J=6.4 Hz, 1H), 3.53 (dd, J=14.4, 4.8 Hz, 1H), 3.16 (m, 2H), 3.07–2.74 (m, 2H), 1.91 (m, 2H), 1.70 (m, 2H), 1.23–1.10 (m, 12H). MS (ESI) m/z 482.6 (M+H$^+$).

Example 87

H-Asp-Phe-OPropofol (195)

Following procedures for the preparation of compound H-Ala-Phe-OPropofol and substituting Boc-Ala-OH with Boc-Asp(O$^t$Bu)-OH provided the title compound (195). $^1$H-NMR (400 MHz, CD$_3$OD): δ 7.36–7.13 (m, 8H), 5.07 (dd, J=10, 5.6 Hz, 1H), 3.89 (dd, J=9.6, 3.6 Hz, 1H), 3.45 (dd, J=14.0, 5.2 Hz, 1H), 3.10 (dd, J=14.0, 10 Hz, 1H), 2.93 (m, 1H), 2.75 (m, 2H), 2.50 (dd, J=17.2, 10.4 Hz, 1H), 1.23–1.03 (m, 12H). MS (ESI) m/z 441.3 (M+H$^+$).

Example 88

H-Gln-Phe-OPropofol (196)

Following procedures for the preparation of compound H-Ala-Phe-OPropofol and substituting Boc-Ala-OH with Boc-Gln-OH provided the title compound (196). $^1$H-NMR (400 MHz, CD$_3$OD): δ 7.38–7.15 (m, 8H), 5.11 (dd, J=10.0, 5.6 Hz, 1H), 3.89 (t, J=6.0 Hz, 1H), 3.49 (dd, J=14.0, 4.8 Hz, 1H), 3.14 (dd, J=14.0, 10.0 Hz, 1H), 2.98 (m, 1H), 2.71 (m, 1H), 2.46 (t, J=7.2 Hz, 2H), 2.08 (m, 2H), 1.13 (m, 12H). MS (ESI) m/z 454.3 (M+H$^+$).

Example 89

H-Glu-Phe-OPropofol (197)

Following procedures for the preparation of compound H-Ala-Phe-OPropofol and substituting Boc-Ala-OH with Boc-Glu(O$^t$Bu)-OH provided the title compound (197). $^1$H-NMR (400 MHz, CD$_3$OD): δ 7.37–7.14 (m, 8H), 5.10 (dd, J=10.0, 5.6 Hz, 1H), 3.83 (dd, J=8.0, 4.8 Hz, 1H), 3.47 (dd, J=14.0, 5.6 Hz, 1H), 3.13 (dd, J=14.0, 10.0 Hz, 1H), 2.95 (m, 1H), 2.69 (m, 1H), 2.43 (m, 2H), 2.08 (m, 2H), 1.13 (m, 12H). MS (ESI) m/z 455.7 (M+H$^+$).

Example 90

H-Gly-Phe-OPropofol (198)

Following procedures for the preparation of compound H-Ala-Phe-OPropofol and substituting Boc-Ala-OH with Boc-Gly-OH provided the title compound (198). $^1$H-NMR (400 MHz, CD$_3$OD): δ 7.36–7.15 (m, 8H), 5.14 (dd, J=10.0, 5.6 Hz, 1H), 3.64 (ABq, J=28.4, 16.0 Hz, 2H), 3.45 (dd, J=14.0, 4.0 Hz, 1H), 3.10 (dd, J=14.0, 10.0 Hz, 1H), 2.96 (m, 1H), 2.75 (m, 1H), 1.14 (d, J=6.8 Hz, 12H). MS (ESI) m/z 383.3 (M+H$^+$).

Example 91

H-His-Phe-OPropofol (199)

Following procedures for the preparation of compound H-Ala-Phe-OPropofol and substituting Boc-Ala-OH with Boc-His(Boc)-OH provided the title compound (199). $^1$H-NMR (400 MHz, CD$_3$OD): δ 8.09 (s, 1H), 8.06(s, 1H), 7.38–7.11 (m, 8H), 5.13 (m, 1H), 4.12 (m, 1H), 3.52 (dd, J=14.4, 5.2 Hz, 1H), 3.27–3.06 (m, 2H), 2.98–2.76 (m, 2H), 2.96 (m, 1H), 1.14 (m, J=12H). MS (ESI) m/z 463.3 (M+H$^+$).

Example 92

H-Pro-Phe-OPropofol (200)

Following procedures for the preparation of compound H-Ala-Phe-OPropofol and substituting Boc-Ala-OH with Boc-Pro-OH provided the title compound (200). $^1$H-NMR (400 MHz, CD$_3$OD): δ 7.38–7.14 (m, 8H), 5.12 (dd, J=10.4, 5.6 Hz, 1H), 4.19 (dd, J=14.4, 5.2 Hz, 1H), 3.13 (dd, J=14.0, 10.0 Hz, 1H), 2.96 (m, 1H), 2.72 (m, 1H), 1.13 (m, J=12H). MS (ESI) m/z 424.6 (M+H$^+$).

Example 93

H-Ser-Phe-OPropofol (201)

Following procedures for the preparation of compound H-Ala-Phe-OPropofol and substituting Boc-Ala-OH with Boc-Ser-OH provided the title compound (201). $^1$H-NMR (400 MHz, CD$_3$OD): δ 7.36–7.14 (m, 8H), 5.14 (dd, J=9.6, 6.4 Hz, 1H), 3.95 (dd, J=10.8, 4.4 Hz, 1H), 3.70 (dd, J=11.2, 8.0 Hz, 1H), 3.43 (dd, J=13.6, 5.6 Hz, 1H), 3.14 (dd, J=14, 9.6 Hz, 1H), 2.92 (m, 1H), 2.64 (m, 1H), 1.12 (m, 12H). MS (ESI) m/z 413.3 (M+H$^+$).

Example 94

H-Thr-Phe-OPropofol (202)

Following procedures for the preparation of compound H-Ala-Phe-OPropofol and substituting Boc-Ala-OH with Boc-Thr-OH provided the title compound (202). $^1$H-NMR (400 MHz, CD$_3$OD): δ 7.38–7.13 (m, 8H), 5.14 (dd, J=8.8, 5.6 Hz, 1H), 3.92 (m, 1H), 3.53 (d, J=7.2 Hz, 1H), 3.45 (dd, J=14.0, 5.2 Hz, 1H), 3.17 (dd, J=14.4, 9.2 Hz, 1H), 2.96 (m, 1H), 2.66 (m, 1H), 1.30 (d, J=6.0 Hz, 3H), 1.11 (m, 12H). MS (ESI) m/z 427.4 (M+H$^+$).

Example 95

H-Trp-Phe-OPropofol (203)

Following procedures for the preparation of compound and substituting Boc-Ala-OH with Boc-Trp-OH provided the title compound (203). $^1$H-NMR (400 MHz, CD$_3$OD): δ 7.63 (d, J=8.0 Hz, 1H), 7.34–7.00 (m, 12H), 5.13 (dd, J=8.8, 6.0 Hz, 1H), 3.86 (dd, J=8.4, 4.4 Hz, 1H), 3.37 (dd, J=14.0, 6.0 Hz, 1H), 3.07 (dd, J=13.6, 8.8 Hz, 1H), 2.99 (m, 2H), 2.69 (m, 1H), 1.13 (m, 12H). MS (ESI) m/z 512.4 (M+H$^+$).

Example 96

H-Tyr-Phe-OPropofol (204)

Following procedures for the preparation of compound H-Ala-Phe-OPropofol and substituting Boc-Ala-OH with Boc-Tyr-OH provided the title compound (204). $^1$H-NMR (400 MHz, CD$_3$OD): δ 7.36–7.15 (m, 8H), 7.08 (d, J=8.0 Hz, 2H), 6.72 (d, J=8.0 Hz, 2H), 5.15 (dd, J=10.0, 5.6 Hz, 1H), 3.94 (dd, J=9.2, 4.0 Hz, 1H), 3.49 (dd, J=14.0, 5.6 Hz, 1H), 3.18 (m, 2H), 2.98 (m, 1H), 2.82 (dd, J=14.4, 8.8 Hz, 1H), 2.72 (m, 1H), 1.15 (m, 12H). MS (ESI) m/z 512.4 (M+H$^+$).

Example 97

H-Val-Phe-OPropofol (205)

Following procedures for the preparation of compound H-Ala-Phe-OPropofol and substituting Boc-Ala-OH with Boc-Val-OH provided the title compound (205). $^1$H-NMR (400 MHz, CD$_3$OD): δ 7.37–7.14 (m, 8H), 5.16 (dd, J=10.0, 5.6 Hz, 1H), 3.59 (d, J=5.2 Hz, 1H), 3.44 (dd, J=14.0, 5.6 Hz, 1H), 3.13 (dd, J=14.0, 9.6 Hz, 1H), 2.98 (m, 1H), 2.68 (m, 1H), 2.20 (m, 1H), 1.11 (m, 12H), 1.07–0.98 (dd, J=29.6, 7.2 Hz, 6H). MS (ESI) m/z 425.4 (M+H$^+$).

Example 98

H-Asp-Ser(β-OC(O)OPropofol)-OH (206)

Following procedures for the preparation of compound (161) and substituting Boc-Ala-OH with Boc-Asp(O$^t$Bu)-OH in Step A provided the title compound (206). $^1$H-NMR (400 MHz, CD$_3$OD): δ 7.16 (m, 3H), 4.72 (dd, J=5.2, 3.6 Hz, 1H), 4.63 (dd, J=11.6, 5.6 Hz, 1H), 4.55 (dd, J=11.2, 3.2 Hz, 1H), 4.21 (dd, J=10, 4 Hz, 1H), 2.99 (m, 3H), 2.70 (dd, J=17.6, 10 Hz, 1H), 1.18 (d, J=7.2 Hz, 12H). MS (ESI) m/z (M+H$^+$).

Example 99

H-Lys-Ser(β-OC(O)OPropofol)-OH (207)

Following procedures for the preparation of compound (161) and substituting Boc-Ala-OH with Boc-Lys(Boc)-OH in Step A provided the title compound (207). $^1$H-NMR (400 MHz, CD$_3$OD): δ 7.16 (m, 3H), 4.65 (t, J=5.2 Hz, 1H), 4.56 (m, 2H), 3.92 (t, J=6.8 Hz, 1H), 2.97 (m, 4H), 2.02–1.84 (m, 2H), 1.71–1.54 (m, 2H), 1.18 (d, J=7.2 Hz, 12H). MS (ESI) m/z (M+H$^+$).

Example 100

H-Ser-Ser(β-OC(O)OPropofol)-OH (208)

Following procedures for the preparation of compound (161) and substituting Boc-Ala-OH with Boc-Ser(O$^t$Bu)-OH in Step A provided the title compound (208). $^1$H-NMR (400 MHz, CD$_3$OD): δ 7.16 (m, 3H), 4.60 (m, 3H), 3.95 (m, 3H), 2.99 (m, J=2H), 1.18 (d, J=7.2 Hz, 12H). MS (ESI) m/z 397.7 (M+H$^+$).

Example 101

H-Tyr-Ser(β-OC(O)OPropofol)-OH (209)

Following procedures for the preparation of compound (161) and substituting Boc-Ala-OH with Boc-Tyr-OH in Step A provided the title compound (209). $^1$H-NMR (400 MHz, CD$_3$OD): δ 7.15 (m, 5H), 6.76 (d, J=8.8 Hz, 2H), 4.58 (m, 3H), 4.08 (dd, 8.8, 4.8 Hz, 1H), 2.97 (m, 3H), 1.17 (d, J=6.8 Hz, 12H). MS (ESI) m/z 473.7 (M+H$^+$).

Example 102

H-Ala-Thr(β-OC(O)OPropofol)-OH (210)

Following procedures for the preparation of compound (161) and substituting Boc-Ser(O$^t$Bu)-OH with Boc-Thr(O$^t$Bu)-OH in Step A provided the title compound (210). $^1$H-NMR (400 MHz, CD$_3$OD): δ 7.16 (m, 3H), 4.49 (m, 1H), 4.09 (q, J=7.2 Hz, 1H), 2.95 (m, 2H), 1.57 (d, J=7.2 Hz, 3H), 1.41 (d, J=6.4 Hz, 3H), 1.18 (dd, J=6.8 Hz, 1.6 Hz, 12H). MS (ESI) m/z 395.8 (M+H$^+$).

Example 103

H-Asn-Thr(β-OC(O)OPropofol)-OH (211)

Following procedures for the preparation of compound H-Ala-Thr(γ-OC(O)OPropofol)-OH and substituting Boc-Asn-OH for Boc-Ala-OH in Step A provided the title compound (211). $^1$H-NMR (400 MHz, CD$_3$OD): δ 7.16 (m, 3H), 5.49 (m, 1H), 4.36 (dd, J=10, 3.6 Hz, 1H), 3.04 (dd, J=17.2, 3.2 Hz, 1H), 2.94 (m, 2H), 2.78 (m, 11H), 1.41 (d, J=6.4 Hz, 3H), 1.18 (dd, J=6.8 Hz, 1.6 Hz, 12H). MS (ESI) m/z 438.8 (M+H$^+$).

Example 104

H-Lys-Thr(β-OC(O)OPropofol)-OH (212)

Following procedures for the preparation of compound H-Ala-Thr(γ-OC(O)OPropofol)-OH and substituting Boc-Lys(Boc)-OH for Boc-Ala-OH in Step A provided the title compound (212). $^1$H-NMR (400 MHz, CD$_3$OD): δ 7.17 (m, 3H), 5.50 (m, 1H), 4.09 (t, J=6.4 Hz, 1H), 2.94 (m, 2H), 1.98 (m, 2H), 1.74 (m, 2H), 1.60 (m, 2H), 1.42 (d, J=6.4 Hz, 3H), 1.18 (d, J=6.8 Hz, 12H). MS (ESI) m/z 452.9 (M+H$^+$).

Example 105

H-Ser-Thr(β-OC(O)OPropofol)-OH (213)

Following procedures for the preparation of compound H-Ala-Thr(γ-OC(O)OPropofol)-OH and substituting Boc-Ser(O$^t$Bu)-OH for Boc-Ala-OH in Step A provided the title compound (213). $^1$H-NMR (400 MHz, CD$_3$OD): δ 7.16 (m, 31H), 5.49 (m, 1H), 4.11 (dd, J=6.8, 4 Hz, 1H), 3.87 (dd, J=12.0, 7.2 Hz, 1H), 2.95 (m, 2H), 1.42 (d, J=6.4 Hz, 3H), 1.18 (d, J=6.8 Hz, 12H). MS (ESI) m/z 411.8 (M+H$^+$).

Example 106

H-Val-Thr(β-OC(O)OPropofol)-OH (214)

Following procedures for the preparation of compound H-Ala-Thr(γ-OC(O)OPropofol)-OH and substituting Boc-Val-OH for Boc-Ala-OH in Step A provided the title compound (214). $^1$H-NMR (400 MHz, CD$_3$OD): δ 7.16 (m, 3H), 3.89 (d, J=5.6 Hz, 1H), 2.95 (m, 2H), 2.30 (m, 1H), 1.42 (d, J=6.4 Hz, 3H), 1.18 (dd, J=6.8 Hz, 1.6 Hz, 12H), 1.12 (dd, J=20.4, 7.2 Hz, 6H). MS (ESI) m/z 423.8 (M+H$^+$).

Example 107

H-Ala-Cys(β-SC(O)OPropofol)-OH (215)

Step A: (Boc-Ala-Cys-O$^t$Bu)$_2$ (216)

To a mixture of cystine tert-butyl diester hydrochloride (0.5 g, 1.17 mmol) and Boc-Ala-OH (0.45 g, 2.38 mmol) in DMF (8 mL) was added O-Benzotriazol-1-yl-N,N,N',N'-tetramethyluronium hexafluorophosphate (0.9 g, 237 mmol) followed by triethylamine (0.45 mL, 258 mmol). The resulting reaction mixture was stirred for 14 h at room temperature, and then diluted with 10% citric acid aqueous solution (20 mL) and ethyl acetate (50 mL). The layers were separated and the organic layer was washed with saturated NaHCO$_3$ aqueous solution (30 mL), brine (2×20 mL), dried over MgSO$_4$ and concentrated in vacuo. The crude residue was purified by silica gel chromatography (hexane to 60% ethyl acetate/hexane) to afford 0.77 g (93% yield) of the desired product (216).

Step B: Boc-Ala-Cys-O$^t$Bu (217)

To a solution of (216) (0.77 g, 1.1 mmol) in ethanol (3 mL) was added indium powder (0.68 g, 5.9 mmol) and ammonium chloride (0.15 g, 2.86 mmol). The resulting mixture was stirred under reflux for 14 h, then cooled to room temperature and filtered through a short plug of silica gel. The silica gel plug was washed with ethyl acetate and the filtrate was concentrated in vacuo. The crude product (217) was carried to the next step without further purification.

Step C: H-Ala-Cys(β-SC(O)OPropofol)-OH (215)

To a cooled solution (0° C.) of crude (217) (0.5 g, 1.43 mmol) in dichloromethane (4 mL) was added triethylamine (0.22 mL, 1.57 mmol) followed by 2,6-bis(isopropyl)phenoxycarbonyl chloride (163) (0.37 g, 153 mmol). The resulting mixture was stirred at room temperature for 15 h, and then diluted with 10% citric acid aqueous solution (10 mL) and ethyl acetate (30 mL). The layers were separated and the organic layer was washed with brine (30 mL), dried over MgSO$_4$ and concentrated in vacuo. The crude residue was dissolved in dichloromethane (4 mL) and treated with 4 N HCl in dioxane (3 mL), followed by trifluoroacetic acid (0.5 mL). The mixture was stirred at room temperature for 14 h the solvent was removed in vacuo. The crude product was purified by preparative LC/MS to afford the title compound (215) (128 mg, 22% yield). $^1$H-NMR (400 MHz, CD$_3$OD): δ 7.21–7.14 (m, 3H), 4.49–4.46 (dd, J=7.6, 4.8 Hz, 1H), 3.88–3.86 (q, J=6.8 Hz, 1H), 3.64–3.59 (dd, J=13.6, 4.8 Hz, 1H), 3.34–3.32 (m, 1H), 2.96 (m, 2H), 1.52 (d, J=6.8 Hz, 3H), 1.19 (d, J=6.8 Hz, 6H), 1.17 (d, J=6.8 Hz, 6H). MS (ESI) m/z 397.77 (M+H$^+$).

Example 108

H-Lys-Cys(β-SC(O)OPropofol)-OH (218)

Following procedures for the preparation of H-Ala-Cys(β-SC(O)OPropofol)-OH, and substituting Boc-Ala-OH with Boc-Lys(Boc)-OH, provided the title compound (218). $^1$H-NMR (400 MHz, CD$_3$OD): δ 7.22–7.14 (m, 3H), 4.53–4.50 (dd, J=8.8, 4.8 Hz, 1H), 3.87 (t, J=6.0 Hz, 1H), 3.64–3.59 (dd, J=13.6, 4.8 Hz, 1H), 3.27–3.22 (dd, J=13.4, 8.4 Hz, 1H), 3.00–2.91 (m, 4H), 1.96–1.87 (m, 2H), 1.71–1.65 (m, 2H), 1.59–1.52 (m, 2H), 1.19 (d, J=7.2 Hz, 6H), 1.17 (d, J=6.8 Hz, 6H). MS (ESI) m/z 454.85 (M+H$^+$).

Example 109

H-Ser-Cys(β-SC(O)OPropofol)-OH (219)

Following procedures for the preparation of H-Ala-Cys(β-SC(O)OPropofol)-OH, and substituting Boc-Ala-OH with Boc-Ser(O$^t$Bu)-OH, provided the title compound (219). $^1$H-NMR (400 MHz, CD$_3$OD): δ 7.22–7.14 (m, 3H), 4.55–4.52 (dd, J=7.6, 4.4 Hz, 1H), 3.91–3.87 (m, 3H), 3.66–3.62 (dd, J=13.6, 4.4 Hz, 1H), 3.32–3.26 (m, 1H), 3.00–2.94 (m, 2H), 1.19 (d, J=6.8 Hz, 6H), 1.17 (d, J=6.8 Hz, 6H). MS (ESI) m/z 414.3 (M+H$^+$).

Example 110

H-Asp-Asp(OCH$_2$OPropofol)-OH (220)

Step A: Propofol Chloromethyl Ether (221)

Propofol (5.5 mL, 30 mmol) was added to a suspension of sodium hydride (1.26 g, 31.5 mmol) in ethylene glycol dimethyl ether (30 mL) at 0° C. The suspension was stirred for 15 min. This mixture was then added to a solution of iodochloromethane (11.0 mL, 150 mmol) in ethylene glycol dimethyl ether (30 mL). The resulting mixture was stirred for 14 h at room temperature and diluted with hexane. The organic solution was then washed with water, dried over magnesium sulfate and then concentrated in vacuo. The crude compound was used without further purification. $^1$H-NMR (400 MHz, CDCl$_3$): δ 7.1 (s, 3H), 5.17 (s, 2H), 3.35 (m, 2H), 1.16 (d, J=6.8 Hz, 12H)

Step B: Boc-Asp(OCH$_2$OPropofol)-OBn (222)

The above intermediate (2.26 g, 10 mmol) was mixed with the cesium salt of Boc-Asp-OBn (7.02 g, 15 mmol) in DMF (20 mL) and stirred for 14 h at room temperature. The resulting solution was diluted with ether and the organic solution was washed with 10% aqueous citric acid solution (2×30 mL), and brine (2×30 mL). The organic layer was dried over magnesium sulfate and then concentrated in vacuo. The crude compound was purified by chromatography on silica gel (Biotage), eluting with a gradient of hexane to 10% EtOAc/hexane) then concentrated in vacuo (1.78 g, 34% yield). $^1$H-NMR (400 MHz, CDCl$_3$): δ 7.30–7.31 (m, 5H), 7.07–7.11 (m, 3H) 5.41–5.53 (m, 2H), 5.15 (s, 2H), 4.67 (m, 1H), 3.2–3.26 (m, 2H), 3.07–3.08 (d, J=4.4 Hz, 1H), 2.88–2.90 (d, J=4.4 Hz, 11H), 2.84 (d, J=4.4 Hz, 1H), 1.42 (s, 9H), 1.2 (d, J=2.4 Hz, 6H), 1.18 (d, J=2.4 Hz, 6H). MS (ESI) m/z 536.4 (M+Na$^+$)

Step C: H-Asp(OCH$_2$OPropofol)-OBn (223)

The pure compound (1.78 g, 3.32 mmol) from above was dissolved in dichloromethane (5 mL) and treated with trifluoroacetic acid (5 mL). The resulting mixture was stirred at room temperature for 3 h. The solvent was removed in vacuo and the crude residue was carried to the next step without further purification.

Step D: CBz-Asp(OBn)-Asp(OCH$_2$OPropofol)-OBn (224)

To a solution of above compound (0.45 g, 1 mmol) and Cbz-Asp(OBn)-OH (0.39 g, 1.1 mmol) in DMF (4 mL) was added diisopropylethylamine (0.56 mL, 3.3 mmol) followed by O-(7-azabenzotriazol-1-yl)-N,N,N',N'-tetramethyluronium hexafluoro-phosphate(0.42 g, 1.1 mmol). The resulting mixture was stirred at room temperature for 14 h and then diluted with 40 mL of ethyl acetate. The organic solution was washed with 10% aqueous citric acid solution (2×30 mL), saturated aqueous sodium bicarbonate solution (2×30 mL) and brine (2×30 mL). The organic layer was dried over magnesium sulfate and then concentrated in vacuo. The crude compound (0.62 g) was used without further purification.

Step E: H-Asp-Asp(OCH₂OPropofol)-OH (220)

To a flask containing 50 mg of 10% Pd—C was added a solution of Asp-Asp (Obzl)-OCH₂OPropofol (0.62 g, 0.94 mmol) in methanol (5 mL) under nitrogen. The resulting mixture was degassed three times, after which hydrogen was introduced via a balloon apparatus. The suspended mixture was allowed to stir vigorously for 4 h. The reaction mixture was filtered through a pad of celite and concentrated in vacuo, then purified by preparative LC/MS to afford the title compound (42 mg, 10% yield). $^1$H-NMR (400 MHz, CD₃OD): δ 7.09 (s, 3H), 5.53 (m, 2H), 4.67 (m, 1H), 4.10 (m, 1H), 3.41 (dd, J=8.0, 16.4 Hz, 1H), 2.86–2.95 (m, 3H), 1.19 (d, J=7.2 Hz, 12H). MS (ESI) m/z 439.8 (M+H⁺).

Example 111

H-Trp-Asp(OCH₂OPropofol)-OH (225)

Following procedures for the preparation of H-Asp-Asp (OCH₂OPropofol)-OH, and substituting Boc-Asp-OBn with Boc-Trp(Boc)-OH, provided the title compound (225). $^1$H-NMR (400 MHz, CD₃OD): δ 7.6 (d, J=8.0 Hz, 1H), 7.33 (d, J=8.0 Hz, 1H), 7.21 (s, 1H), 7.02–7.11 (m, 2H), 7.08 (m, 3H), 5.47 (m, 2H), 4.53 (m, 1H), 4.13 (m, 1H), 3.4 (m, 2H), 3.24 (dd, J=8.0, 16.4 Hz, 1H), 2.89 (m, 3H), 1.18 (d, J=7.4 Hz, 12H). MS (ESI) m/z 510.8(M+H⁺).

Example 112

H-His-Asp(OCH₂OPropofol)-OH (226)

Following procedures for preparation of H-Asp-Asp (OCH₂OPropofol)-OH, and substituting Boc-Asp-OBn with Boc-His(Boc)-OH, provided the title compound (226). $^1$H-NMR (400 MHz, CD₃OD): δ 8.35 (s, 1H), 8.09 (s, 2H), 7.15 (s, 1H), 7.09 (s, 3H), 5.51–5.56 (m, 2H), 4.66–4.68 (m, 1H), 4.10–4.13 (m, 1H), 3.28–3.24 (m, 2H), 2.99–3.05 (dd, J=4.8, 13.6 Hz, 2H), 2.89 (dd, J=8.0, 16.0 Hz, 2H), 1.18 (d, J=7.2 Hz, 12H). MS (ESI) m/z 461.8 (M+H⁺).

Example 113

H-Asn-Asp(OCH₂OPropofol)-OH (227)

Following procedures for preparation of H-Asp-Asp (OCH₂OPropofol)-OH, and substituting Boc-Asp-OBn with Boc-Asn-OH, provided the title compound (227). $^1$H-NMR (400 MHz, CD₃OD): δ 7.09 (s, 3H), 5.51 (s, 2H), 4.56–4.58 (m, 1H), 4.14–4.18 (m, 1H), 3.28–3.24 (m, 2H), 2.93–2.98 (m, 2H), 2.85–2.89 (dd, J=4.8, 13.6 Hz, 1H), 2.68–2.75 (dd, J=8.0, 16.0 Hz, 2H), 1.18 (d, J=7.2 Hz, 12H). MS (ESI) m/z 438.8 (M+H⁺).

Example 114

H-Gln-Asp(OCH₂OPropofol)-OH (228)

Following procedures for preparation of H-Asp-Asp (OCH₂OPropofol)-OH, and substituting Boc-Asp-OBn with Boc-Gln-OH, provided the title compound (228). $^1$H-NMR (400 MHz, CD₃OD): δ 7.09 (s, 3H), 5.51 (s, 2H), 4.61 (m, 1H), 3.89 (m, 1H), 3.46 (m, 2H), 2.84–2.98 (m, 2H), 2.46 (m, 2H), 2.11 (m, 2H), 1.18 (d, J=7.2 Hz, 12H). MS (ESI) m/z 452.8(M+H⁺).

Example 115

H-Thr-Asp(OCH₂OPropofol)-OH (229)

Following procedures for preparation of H-Asp-Asp (OCH₂OPropofol)-OH, and substituting Boc-Asp-OBn with Boc-Thr(O$^t$Bu)-OH, provided the title compound (229). $^1$H-NMR (400 MHz, CD₃OD): δ 7.09 (s, 3H), 5.51 (s, 2H), 4.53 (m, 1H), 4.07 (m, 1H), 3.63 (d, J=5.6 Hz, 1H), 3.46 (m, 2H), 2.84–2.98(m, 2H), 1.23(d, J=6.8 Hz, 3H), 1.18 (d, J=7.2 Hz, 12H). MS (ESI) m/z 425.3 (M+H⁺).

Example 116

H-Ser-Asp(OCH₂OPropofol)-OH (230)

Following procedures for preparation of H-Asp-Asp (OCH₂OPropofol)-OH, and substituting Boc-Asp-OBn with Boc-Ser(O$^t$Bu)-OH, provided the title compound (230). $^1$H-NMR (400 MHz, CD₃OD): δ 7.09 (s, 3H), 5.51 (s, 2H), 4.53 (m, 1H), 4.07 (m, 1H), 3.63 (d, J=5.6 Hz, 11H), 3.46 (m, 2H), 2.84–2.98 (m, 2H), 1.18 (d, J=7.2 Hz, 12H). MS (ESI) m/z 411.8 (M+H⁺).

Example 117

H-Gly-Asp(OCH₂OPropofol)-OH (231)

Following procedures for preparation of H-Asp-Asp (OCH₂OPropofol)-OH, and substituting Boc-Asp-OBn with Boc-Gly-OH, provided the title compound (231). $^1$H-NMR (400 MHz, CD₃OD): δ 7.09 (s, 3H), 5.51 (m, 2H), 4.61 (m, 1H), 3.55–3.69 (m, 2H), 2.84–2.98 (m, 2H), 1.18 (d, J=7.2 Hz, 12H). MS (ESI) m/z 381.8 (M+H⁺).

Example 118

H-Glu-Asp(OCH₂OPropofol)-OH (232)

Following procedures for preparation of H-Asp-Asp (OCH₂OPropofol)-OH, and substituting Boc-Asp-OBn with Boc-Glu(O$^t$Bu)-OH, provided the title compound (232). $^1$H-NMR (400 MHz, CD₃OD): δ 7.09 (s, 3H), 5.51 (m, 2H), 4.61 (m, 1H), 3.91 (m, 1H), 3.34 (m, 2H), 2.92–2.97 (m, 2H), 2.51–2.54 (m, 2H), 2.08–2.13 (m, 2H), 1.18 (d, J=7.2 Hz, 12H). MS (ESI) m/z 453.2 (M+H⁺).

Example 119

H-Tyr-Asp(OCH₂OPropofol)-OH (233)

Following procedures for preparation of H-Asp-Asp (OCH₂OPropofol)-OH, and substituting Boc-Asp-OBn with Boc-Tyr-OH, provided the title compound (233). $^1$H-NMR (400 MHz, CD₃OD): δ 7.09–7.11 (m, 5H), 6.73–6.75 (d, J=8.0 Hz, 2H), 5.51 (m, 2H), 4.61 (m, 1H), 4.01 (m, 1H), 3.34 (m, 2H), 2.92–2.97 (m, 2H) 1.18 (d, J=7.2 Hz, 12H). MS (ESI) m/z 487.3 (M+H⁺).

Example 120

H-Ala-Asp(OCH₂OPropofol)-OH (234)

Following procedures for preparation of H-Asp-Asp (OCH₂OPropofol)-OH, and substituting Boc-Asp-OBn with Boc-Ala-OH, provided the title compound (234). $^1$H-NMR (400 MHz, CD₃OD): δ 7.09 (s, 3H), 5.52 (s, 2H), 4.55–4.52

(dd, J=7.2, 4.8 Hz, 1H), 3.91 (q, J=6.8 Hz, 1H), 3.34–3.30 (m, 2H), 2.98–2.94 (dd, J=16.4, 4.8 Hz, 1H), 2.89–2.83 (dd, J=16.4, 7.6 Hz, 1H), 1.50 (d, J=7.2 Hz, 3H), 1.21 (d, J=7.2 Hz, 12H). MS (ESI) m/z 395.37 (M+H$^+$).

Example 121

H-Asp(OCH$_2$OPropofol)-Lys-OH (235)

Step A: Boc-Asp(OCH$_2$OPropofol)-OH (236)

To a flask containing 50 mg of 10% Pd—C was added a solution of Boc-Asp(OCH$_2$OPropofol)-OBn (0.77 g, 1.5 mmol) in methanol under nitrogen. The resulting mixture was degassed three times, after which hydrogen was introduced via a balloon apparatus. The suspended mixture was allowed to stir vigorously for 4 h at room temperature. The reaction mixture was filtered through a pad of celite and concentrated in vacuo. The crude compound (236) (0.64 g) was used without further purification.

Step B: Boc-Asp(OCH$_2$OPropofol)-Lys(Boc)-O$^t$Bu (237)

To a solution of (236) (0.64 g, 1.5 mmol) and H-Lys (Boc)-O$^t$Bu (0.557 g, 1.65 mmol) in DMF was added diisopropylethylamine (0.51 mL, 3.0 mmol) followed by O-(7-azabenzotriazol-1-yl)-N,N,N',N'-tetramethyluronium hexafluorophosphate(0.63 g, 1.65 mmol). The resulting mixture was stirred at room temperature for 14 h and then diluted with ethyl acetate (40 mL). The organic solution was washed with 10% aqueous citric acid solution (2×30 mL), saturated aqueous sodium bicarbonate solution (2×30 mL) and brine (2×30 mL). The organic layer was dried over magnesium sulfate and then concentrated in vacuo. The crude compound (237) was used without further purification.

Step C: H-Asp(OCH$_2$OPropofol)-Lys-OH (235)

Compound (237) (0.65 g, 0.92 mmol) from above was dissolved in dichloromethane (1.5 mL) and treated with trifluoroacetic acid (1.5 mL). The resulting mixture was stirred at room temperature for 3 h. The solvent was removed in vacuo and the crude residue was purified by preparative LC/MS to afford the title compound (235). $^1$H-NMR (400 MHz, CD$_3$OD): δ 7.09 (s, 3H), 5.51 (s, 2H), 4.23 (m, 1H), 4.07 (m, 1H), 2.79–3.02 (m, 4H), 1.81 (m, 2H), 1.62–1.78 (m, 4H), 1.45 (m, 2H), 1.18 (d, J=7.2 Hz, 12H). MS (ESI) m/z 452.8(M+H$^+$).

Example 122

H-Asp(OCH$_2$OPropofol)-Asp-OH (238)

Following procedures for preparation of H-Asp (OCH$_2$OPropofol)-Lys, and substituting H-Lys(Boc)-O$^t$Bu with H-Asp(O$^t$Bu)—O$^t$Bu, provided the title compound (238). $^1$H-NMR (400 MHz, CD$_3$OD): δ 7.11 (s, 3H), 5.62 (s, 2H), 4.59–4.56 (m, 1H), 4.22–4.19 (dd, J=9.2, 4.0 Hz, 1H), 3.18–3.13 (dd, J=17.6, 4.0 Hz, 1H), 2.93–2.72 (m, 5H), 1.21 (d, J=6.4 Hz, 12H). MS (ESI) m/z 439.27 (M+H$^+$).

Example 123

H-Asp(OCH$_2$OPropofol)-Arg-OH (239)

Following procedures for preparation of H-Asp (OCH$_2$OPropofol)-Lys, and substituting H-Lys(Boc)-O$^t$Bu with H-Arg(Pmc)-O$^t$Bu, provided the title compound (239). $^1$H-NMR (400 MHz, CD$_3$OD): δ 7.11 (s, 3H), 5.62–5.59 (ABq, J=7.2, 5.6 Hz, 2H), 4.25 (t, J=6.0 Hz, 1H), 4.14 (m, 1H), 3.34–3.31 (m, 2H), 3.18 (t, J=6.8 Hz, 2H), 3.14–3.09 (dd, J=17.6, 4.0 Hz, 1H), 2.91–2.84 (dd, J=17.2, 8.4 Hz, 1H), 1.89–1.86 (m, 1H), 1.77–1.63 (m, 3H), 1.21 (d, J=6.4 Hz, 12H). MS (ESI) m/z 480.28 (M+H$^+$).

Example 124

H-Asp(OCH$_2$OPropofol)-Ser-OH (240)

Following procedures for preparation of H-Asp (OCH$_2$OPropofol)-Lys, and substituting H-Lys(Boc)-O$^t$Bu with H-Ser(O$^t$Bu)-O$^t$Bu, provided the title compound (240). $^1$H-NMR (400 MHz, CD$_3$OD): δ 7.11 (s, 3H), 5.62 (s, 2H), 4.39 (t, J=4.8 Hz, 1H), 4.27–4.24 (dd, J=9.2, 4.4 Hz, 1H), 3.86 (d, J=4.8 Hz, 2H), 3.35–3.31 (m, 2H), 3.21–3.16 (dd, J=17.6, 4.4 Hz, 1H), 2.93–2.86 (dd, J=18.0, 9.2 Hz, 1H), 1.21 (d, J=6.4 Hz, 12H). MS (ESI) m/z 411.31 (M+H$^+$).

Example 125

H-Val-OCH$_2$OPropofol (241)

Step A: Boc-Val-O$^-$Cs$^+$ (242)

To a solution of Boc-Val-OH (1.0 g, 4.6 mmol) in a 1:4 mixture of acetonitrile:H$_2$O (5 mL) was added cesium bicarbonate (0.9 g, 4.6 mmol). The resulting solution was stirred for 10 min, and then the solvent was frozen and lyophilized to give (242) as a white powder.

Step B: H-Val-OCH$_2$OPropofol (241)

To a solution of propofol chloromethyl ether (221) (0.36 g, 1.59 mmol) in DMF (4 mL) was added (242) (0.5 g, 1.42 mmol). The resulting reaction mixture was stirred at room temperature for overnight, then diluted with ethyl acetate (30 mL) and 10% citric acid aqueous solution (20 mL). The layers were separated and the organic layer was washed with brine (2×20 mL), dried over MgSO$_4$ and concentrated in vacuo. The crude residue was dissolved in dichloromethane (4 mL) and treated with trifluoroacetic acid (1 mL). The reaction was stirred for 3 h at room temperature. The solvent was removed in vacuo, and the crude product purified by preparative LC/MS to afford the title compound (241) (118 mg, 27% yield). $^1$H-NMR (400 MHz, CD$_3$OD): δ 7.12–7.08 (m, 3H), 5.63–5.58 (Abq, J=16, 5.2 Hz, 2H), 3.58 (d, J=3.6 Hz, 1H), 3.32–3.25 (m, 2H), 2.24–2.19 (m, 1H), 1.21 (d, J=6.8 Hz, 12H), 1.05 (d, J=6.8 Hz, 3H), 0.96 (d, J=6.8 Hz, 3H). MS (ESI) m/z 308.43 (M+H$^+$).

Example 126

H-Aib-OCH$_2$OPropofol (243)

Following procedures for preparation of H-Val-OCH$_2$OPropofol, and substituting Boc-Val-OH with Boc-Aib-OH, provided the title compound (243). $^1$H-NMR (400 MHz, CD$_3$OD): δ 7.12–7.08 (m, 3H), 5.60 (s, 2H), 3.32–3.25 (m, 2H), 1.49 (s, 6H), 1.21 (d, J=6.8 Hz, 12H). MS (ESI) m/z 294.39 (M+H$^+$).

Example 127

H-Asp(OCH$_2$OPropofol)-OH (244)

Following procedures for preparation of H-Val-OCH$_2$OPropofol, and substituting Boc-Val-OH with Boc-Asp-O$^t$Bu, provided the title compound (244). $^1$H-NMR (400 MHz, CD$_3$OD): δ 7.11 (s, 3H), 5.63–5.57 (Abq, J=21.6, 5.6 Hz, 2H), 3.95–3.92 (dd, J=8.4, 3.6 Hz, 1H), 3.34–3.29 (m, 2H), 3.14–3.08 (dd, J=18.4, 4.0 Hz, 1H), 2.93–2.86 (dd, J=18.4, 8.8 Hz, 1H), 1.21 (d, J=6.8 Hz, 12H). MS (ESI) m/z 324.34 (M+H$^+$).

Example 128

H-Asp-OCH$_2$OPropofol (245)

Following procedures for preparation of H-Val-OCH$_2$OPropofol, and substituting Boc-Val-OH with Boc-Asp(O$^t$Bu)-OH, provided the title compound (245). $^1$H-NMR (400 MHz, CD$_3$OD): δ 7.11 (s, 3H), 5.63–5.68 (Abq, J=89.6, 5.6 Hz, 2H), 4.17 (t, J=5.2 Hz, 1H), 3.31 (m, 2H), 2.82 (d, J=5.6 Hz, 2H), 1.21 (d, J=7.2 Hz, 12H). MS (ESI) m/z 324.34 (M+H$^+$).

Example 129

H-Dap(β-NHC(O)OPropofol)-Ala-OH (246)

Step A: Cbz-Dap(Boc)-Ala-OBn (247)

Cbz-Dap(Boc)-OH (0.41 g, 1.2 mmol) was treated with a mixture of 1-(3-(dimethylamino)propyl)-3-ethylcarbodiimide methiodide (0.374 g, 1.26 mmol) and N-hydroxybenzotriazole (0.17 g, 1.26 mmol) in N-methylmorpholine (0.28 mL, 2.1 mmol) in dichloromethane. H-Ala-OBn (0.26 g, 1.2 mmol) was added to the above solution and the resulting mixture was stirred for 14 h at room temperature, then diluted with ethyl acetate (40 mL). The organic solution was washed with 10% aqueous citric acid solution (2×30 mL), saturated aqueous sodium bicarbonate solution (2×30 mL) and brine (2×30 mL). The organic layer was dried over magnesium sulfate and then concentrated in vacuo. The crude compound (247) (0.51 g) was used without further purification.

Step B: Cbz-Dap-Ala-OBn (248)

Compound (247) (0.51 g, 1.02 mmol) from above was dissolved in dichloromethane (1 mL) and treated with trifluoroacetic acid (1 mL). The resulting mixture was stirred at room temperature for 3 h. The solvent was removed in vacuo and the crude residue (248) (0.49 g) was used in the next step without further purification.

Step C: CBz-Dap(β-NHC(O)OPropofol)-Ala-OBn (249)

To an ice cold solution of chloroformate (163) (0.384 g, 1.6 mmol) in dichloromethane (4 mL) was added triethylamine (0.075 mL, 1.3 mmol) followed by compound (248) (0.4 g, 1 mmol). The resulting mixture was allowed to warm to room temperature and stirred for 12 h. The mixture was diluted with ethyl acetate (30 mL) and washed with 10% aqueous citric acid solution (2×30 mL), dried over MgSO$_4$, filtered and concentrated in vacuo. The crude product (249) (0.66 g) was used in the next step without further purification.

Step D: H-Dap(β-NHC(O)OPropofol)-Ala-OH (246)

To a flask containing 50 mg of 10% Pd—C was added a solution of compound (249) (0.66 g, 1 mmol) in methanol (5 mL) under nitrogen. The resulting mixture was degassed three times, after which hydrogen was introduced via a balloon apparatus. The suspended mixture was allowed to stir vigorously for 4 h. The reaction mixture was filtered through a pad of celite and concentrated in vacuo and the crude residue was purified by preparative LC/MS to afford the title compound (246) (48 mg, 13% yield). $^1$H-NMR (400 MHz, CD$_3$OD): δ 7.11–7.17 (m, 3H), 4.47 (m, 1H), 4.23 (q, 1H), 3.31 (m, 2H), 3.01 (m, 2H), 1.38 (d, J=7.2 Hz, 3H), 1.17 (d, J=7.4 Hz, 12H). MS (ESI) m/z 380.3 (M+H$^+$).

Example 130

H-Lys-Glu(OPropofol)-OH (250)

Following procedures for preparation of compound (107) and substituting CBz-Lys(CBz)-OH for CBz-Ala-OH and compound (105) for compound (102) provided the title compound (250). $^1$H-NMR (400 MHz, CD$_3$OD): δ 7.17 (m, 3H), 4.31 (dd, J=8.4, 5.2 Hz, 11H), 3.90 (dd, J=7.6, 6.0 Hz, 1H), 2.89 (m, 4H), 2.77 (t, J=8.4 Hz, 2H), 2.34 (m, 1H), 2.10 (m, 1H), 1.89 (m, 2H), 1.76–1.50 (m, 4H), 1.18 (d, J=6.8 Hz, 12H). MS (ESI) m/z 437.43 (M+H$^+$).

Example 131

In Vitro Compound Transport Assays: Analysis of Electrogenic Transport in PEPT1-Expressing *Xenopus* Oocytes Transport-induced currents were also measured in *Xenopus* oocytes transfected with rat and human PEPT1 as described in PCT Application WO01/20331. Briefly:

RNA preparation: Rat and human PEPT1 transporter cDNAs were subcloned into a modified pGEM plasmid that contains 5' and 3' untranslated sequences from the *Xenopus* β-actin gene. These sequences increase RNA stability and protein expression. Plasmid cDNA was linearized and used as template for in vitro transcription (Epicentre Technologies transcription kit, 4:1 methylated:non-methylated GTP).

*Xenopus* oocyte isolation. *Xenopus laevis* frogs were anesthetized by immersion in Tricaine (1.5 g/mL in deionized water) for 15 min. Oocytes were removed and digested in frog ringer solution (90 mM NaCl, 2 mM KCl, 1 mM MgCl$_2$, 10 mM NaHEPES, pH 7.45, no CaCl$_2$) with 1 mg/mL collagenase (Worthington Type 3) for 80–100 min with shaking. The oocytes were washed 6 times, and the buffer changed to frog ringer solution containing CaCl$_2$ (1.8 mM). Remaining follicle cells were removed if necessary. Cells were incubated at 16° C., and each oocyte injected with 10–20 μg RNA in 45 μL solution.

Electrophysiology measurements. Transport currents were measured 2–14 days after injection, using a standard two-electrode electrophysiology set-up (Geneclamp 500 amplifier, Digidata 1320/PCLAMP software and ADInstruments hardware and software were used for signal acquisition). Electrodes (2–4 mΩ) were microfabricated using a Sutter Instrument puller and filled with 3M KCl. The bath was directly grounded (transporter currents were less than 0.3 μA). Bath flow was controlled by an automated perfusion system (ALA Scientific Instruments, solenoid valves).

For transporter pharmacology, oocytes were clamped at −60 to −90 mV, and continuous current measurements acquired using PowerLab Software and an ADInstruments digitizer. Current signals were lowpass filtered at 20 Hz and acquired at 4–8 Hz. All bath and drug-containing solutions were frog ringers solution containing $CaCl_2$. Drugs were applied for 10–30 seconds until the induced current reached a new steady-state level, followed by a control solution until baseline currents returned to levels that preceded drug application. The difference current (baseline subtracted from peak current during drug application) reflected the net movement of charge resulting from electrogenic transport and was directly proportional to transport rate. Recordings were made from a single oocyte for up to 60 min, enabling 30–40 separate compounds to be tested per oocyte. Compound-induced currents were saturable and gave half-maximal values at substrate concentrations comparable to radiolabel competition experiments. To compare results between oocytes expressing different levels of transport activity, a saturating concentration of glycyl-sarcosine (1 mM) was used as a common reference to normalize results from test compounds. Using this normalization procedure $I_{max}$ (i.e. maximal induced current) for different compounds tested on different oocytes could be compared.

Each of the compounds (107), (115), (116), (119)–(122), (124), (136), (138)–(140), (143), (145)–(150), (161), (208), (210), (213), (220), (227)–(229), (241), (243) and (250) elicited PEPT-specific currents significantly above background (at least 2% Of $I_{max}$ for Gly-Sar) when tested at 3 mM on oocytes expressing PEPT1, confirming that these compounds serve as substrates for this transporter.

Example 132

Standard Methods for Determination of Enzymatic Cleavage of Prodrugs In Vitro

The stability of propofol prodrugs were evaluated in one or more in vitro systems using a variety of tissue preparations following methods known in the art. Tissues were obtained from commercial sources (e.g., Pel-Freez Biologicals, Rogers, Ark., or GenTest Corporation, Woburn, Mass.). Experimental conditions used for the in vitro studies are described in Table 1 below. Each preparation was incubated with test compound at 37° C. for one hour. Aliquots (50 μL) were removed at 0, 30, and 60 min and quenched with 0.1% trifluoroacetic acid in acetonitrile. Samples were then centrifuged and analyzed by LC/MS/MS (see Examples 59 and 60 below for method details). Stability of drug conjugates towards specific enzymes (e.g., peptidases, etc.) were also assessed in vitro by incubation with the purified enzyme:

Aminopeptidase Stability: Aminopeptidase 1 (Sigma catalog # A-9934) was diluted in deionised water to a concentration of 856 units/mL. Stability studies were conducted by incubating conjugate (5 μM) with 0.856 units/mL aminopeptidase 1 in 50 mM Tris-HCl buffer at pH 8.0 and 37° C. Concentrations of intact conjugate and released drug were determined at zero time and 60 minutes using LC/MS/MS.

Pancreatin Stability: Stability studies were conducted by incubating conjugate (5 μM) with 1% (w/v) pancreatin (Sigma, P-1625, from porcine pancreas) in 0.025 M Tris buffer containing 0.5 M NaCl (pH 7.5) at 37° C. for 60 min. The reaction was stopped by addition of 2 volumes of methanol. After centrifugation at 14,000 rpm for 10 min, the supernatant was removed and analyzed by LC/MS/MS.

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9000 g for 20 min at 4° C. The resulting supernatant (Caco-2 cell homogenate S9 fraction) was aliquoted into 0.5 mL vials and stored at −80° C. until used.

For stability studies, prodrug (5 μM) was incubated in Caco-2 homogenate S9 fraction (0.5 mg protein per mL) for 60 min at 37° C. Concentrations of intact prodrug and released propofol were determined at zero time and 60 minutes using LC/MS/MS.

Preferred conjugates demonstrate at least 1% cleavage to produce the free drug or an active metabolite thereof within a 60 minute period, as summarized in Table 2.

TABLE 1

Standard Conditions for Conjugate In Vitro Metabolism Studies

| Preparation | Substrate Concentration | Cofactors |
| --- | --- | --- |
| Rat Plasma | 2.0 μM | None |
| Human Plasma | 2.0 μM | None |
| Rat Liver S9 (0.5 mg/mL) | 2.0 μM | NADPH |
| Human Liver S9 (0.5 mg/mL) | 2.0 μM | NADPH |
| Human Intestine S9 (0.5 mg/mL) | 2.0 μM | NADPH |
| Carboxypeptidase A (10 units/mL) | 2.0 μM | None |
| Caco-2 Homogenate | 5.0 μM | None |
| Pancreatin | 5.0 μM | None |
| Aminopeptidase | 5.0 μM | None |

* NADPH generating system, e.g., 1.3 mM NADP+, 3.3 mM glucose-6-phosphate, 0.4 U/mL glucose-6-phosphate dehydrogenase, 3.3 mM magnesium chloride and 0.95 mg/mL potassium phosphate, pH 7.4.

TABLE 2

% of Propofol Released from Propofol Prodrugs after 60 min. in Various Tissue Preparations

| | (107) | (121) | (122) | (124) | (138) | (152) | (161) | (192) | (208) | (220) | (250) |
| --- | --- | --- | --- | --- | --- | --- | --- | --- | --- | --- | --- |
| Rat Plasma | 3 | 7 | 2 | 65 | 50 | 37 | 30 | 15 | ND | ND | 79 |
| Human Plasma | 1 | 3 | 0 | 2 | 44 | 0 | 2 | 15 | 2 | 1 | 17 |
| Rat Liver S9 (0.5 mg/mL) | 6 | 0 | 9 | 0 | 0 | 11 | 8 | 60 | ND | ND | 36 |

TABLE 2-continued

% of Propofol Released from Propofol Prodrugs after 60 min. in Various Tissue Preparations

|  | (107) | (121) | (122) | (124) | (138) | (152) | (161) | (192) | (208) | (220) | (250) |
|---|---|---|---|---|---|---|---|---|---|---|---|
| Human Liver S9 (0.5 mg/mL) | 5 | 0 | 6 | 0 | 0 | 8 | 14 | 60 | 3 | 0 | 34 |
| Caco-2 S9 | 4 | 0 | 0 | 0 | 3 | 6 | 20 | 41 | 21 | 49 | 19 |
| Pancreatin | 7 | 0 | 10 | 4 | 9 | 1 | 8 | 0 | 25 | 6 | 0 |

ND—Not done

Example 133

Uptake of Propofol Following Oral Administration to Rats

Step A: Administration Protocol

Propofol was administered as an intravenous bolus injection or by oral gavage to groups of four to six adult male Sprague-Dawley rats (weight approx 250 g) as solutions in PEG400, at doses of 10 mg per kg body weight (I.V.) or 25 mg per kg body weight (oral). Animals were fasted overnight before the study and for 4 hours post-dosing. Blood samples (1.0 mL) were obtained via a jugular vein cannula at intervals over 24 hours after oral dosing. Blood was quenched immediately using acetonitrile with 1% formic acid and then was frozen at −80° C. until analyzed.

Step B: LC/MS/MS Analysis

Concentrations of propofol in plasma were determined using an API 4000 LC/MS/MS instrument equipped with an Agilent 1100 binary pump and an Agilent autosampler. The column was a Phenomenex Hydro-RP 4.6*50 mm column operating at room temperature. The mobile phases were 2 mM aqueous ammonium acetate (A) and 95% acetonitrile with 5 mM ammonium acetate (B). The gradient condition was: 5% B for 1 min, increasing to 90% B in 2.5 min and maintained for 2 min. 20 μL of sample was injected. A Turbo-IonSpray source was used, and propofol was detected in negative ion mode in Q1 at m/z=177. The peaks were integrated using Analyst 1.2 quantitation software.

The oral bioavailability (F) of propofol, determined by comparison of the area under the propofol concentration versus time curve (AUC) following oral administration with the AUC measured following intravenous propofol administration, was found to be very low as expected (F=0.23%).

Example 134

Uptake of Propofol Following Oral Administration of Prodrugs to Rats

Step A: Administration Protocol

Test compounds were administered by oral gavage or as an intravenous bolus injection to groups of four to six adult male Sprague-Dawley rats (weight approx 250 g) as solutions in PEG400 at a dose of 25 mg-equivalents of propofol per kg body weight. Animals were fasted overnight before the study and for 4 hours post-dosing. Blood samples (1.0 mL) were obtained via a jugular vein cannula at intervals over 24 hours after oral dosing. Blood was quenched immediately using acetonitrile with 1% formic acid and then was frozen at −80° C. until analyzed.

Step B: LC/MS/MS Analysis

Concentrations of propofol in whole blood were determined using an API 4000 LC/MS/MS instrument as described above. For determination of the prodrug concentrations in whole blood, the mobile phases were 0.1% formic acid (A) and acetonitrile with 0.1% formic acid (B). The gradient condition was: 5% B for 1 min, increasing to 90% B in 2.5 min and maintained for 2 min. 101 L of sample was injected. A TurboIonSpray source was used and the prodrugs were detected in positive ion mode, using MRM transitions of 365/294 for (107), 457/136 for (122), 422/136 for (124), 422/136 for (124), and 436/84 for (250). The peaks were integrated using Analyst 1.2 quantitation software.

Oral bioavailability (F) of the prodrugs as propofol were determined by comparison of the areas under the propofol concentration versus time curves (AUC) following oral administration of the prodrugs with the AUC measured following intravenous administration of propofol itself on a dose-normalized basis. Each of the compounds (107), (122), (124) and (250) showed substantial oral bioavailabilities as propofol (F>50%) illustrating that actively transported prodrugs can afford dramatic enhancements (>200-fold) in oral bioavailability of propofol.

Example 135

Uptake of Propofol Following Oral Administration of Prodrugs to Monkeys

Step A: Administration Protocol

Test compounds were administered by oral gavage or as an intravenous bolus injection to groups of two to four adult male Cynomologous (Macaca fascicularis) monkeys (weight approx 5 kg) as solutions in water or PEG400 at a dose of 25 mg-equivalents of propofol per kg body weight. Animals were fasted overnight before the study and for 4 hours post-dosing. Blood samples (1.0 mL) were obtained via the femoral vein at intervals over 24 hours after oral dosing. Blood was quenched immediately using acetonitrile with 1% formic acid and then was frozen at −80° C. until analyzed. Test compounds are administered in the monkeys with a minimum of 72 hour wash out period between dosing sessions.

Step B: LC/MS/MS Analysis

Concentrations of propofol in whole blood were determined using an API 4000 LC/MS/MS instrument as described above and the prodrugs were detected in positive ion mode, using MRM transitions of 365/294 for (107), 457/136 for (122), 422/136 for (124), 422.19/136.08 for (124), 423/405 for (140), 436/84 for (146), 381/159 for (161), 399/136 for (192), 436/207 for (201), 397/175 for (208), 411/189 for (213), 439/261 for (220), and 436/84 for (250). The peaks were integrated using Analyst 1.2 quantitation software.

Oral bioavailability (F) of the prodrugs as propofol in monkeys were determined by comparison of the areas under the propofol concentration versus time curves (AUC) following oral administration of the prodrugs with the AUC measured following intravenous administration of propofol itself on a dose-normalized basis.

The compounds (174), (213) and (250) had oral bioavailabilities as propofol >10%, while (140), (146) and (208) had oral bioavailabilities as propofol >40%, illustrating that actively transported prodrugs can afford significant enhancements in oral bioavailability of propofol.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the claim(s) issuing herefrom. All publications and patents cited herein are incorporated by reference.

What is claimed is:

1. A compound of Formula (I):

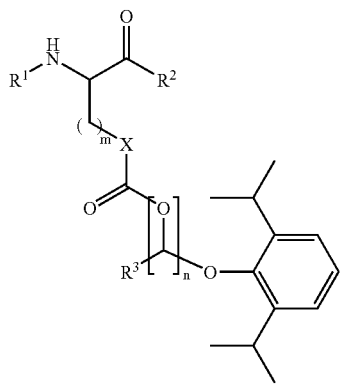

or a pharmaceutically acceptable salt, hydrate, solvate or n-oxide thereof, wherein:

X is selected from the group consisting of a bond, $CH_2$, $NR^{11}$, O and S;

m is 1 or 2;

n is 0 or 1;

$R^1$ is selected from the group consisting of hydrogen, $[R^5NH(CHR^4)_pC(O)]$—, $R^6$—, $R^6C(O)$— and $R^6OC(O)$—;

$R^2$ is —$OR^7$ or —$[NR^8(CHR^9)_qC(O)OR^7]$;

p and q are independently 1 or 2;

$R^3$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

each $R^4$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^4$ and $R^5$ are attached to adjacent atoms then $R^4$ and $R^5$ together with the atoms to which they are bonded form a cycloheteroalkyl or substituted cycloheteroalkyl ring;

$R^5$ is selected from the group consisting of hydrogen, $R^6$—, $R^6C(O)$— and $R^6C(O)$—;

$R^6$ is selected from the group consisting of alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

$R^7$ is selected from the group consisting of hydrogen, alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

$R^8$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

each $R^9$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^8$ and $R^9$ are attached to adjacent atoms then $R^8$ and $R^9$ together with the atoms to which they are bonded form a cycloheteroalkyl or substituted cycloheteroalkyl ring;

$R^{11}$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

with the provisos that:

when $R^1$ is $[R^5NH(CHR^4)_pC(O)]$-then $R^2$ is —$OR^7$; and when $R^2$ is —$[NR^8(CHR^9)_qC(O)OR^7]$ then $R^1$ is not $[R^5NH(CHR^4)_pC(O)]$—.

2. The compound of claim 1, wherein n is 0.

3. The compound of claim 1 having structural Formula (III):

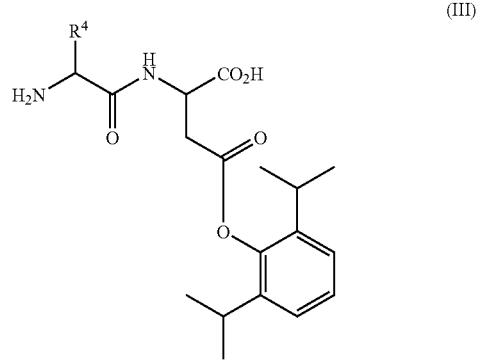

wherein R⁴ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl.

4. The compound of claim 3, wherein R⁴ is selected from the group consisting of hydrogen, methyl, isopropyl, isobutyl, sec-butyl, t-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH2, —CH₂CH₂CH₂NHC(NH)NH₂, phenyl, benzyl, 4-hydroxybenzyl, 4-imidazolylmethyl and 3-indolylmethyl.

5. The compound of claim 1 having structural Formula (IV):

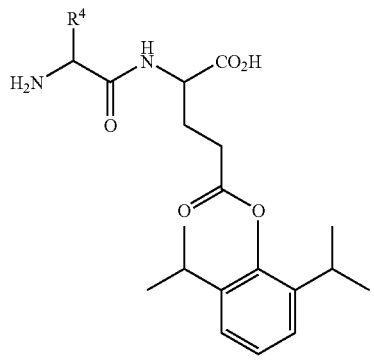

wherein R⁴ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl.

6. The compound of claim 5, wherein R⁴ is selected from the group consisting of hydrogen, methyl, isopropyl, isobutyl, sec-butyl, t-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl and 3-indolylmethyl.

7. The compound of claim 1 having structural Formula (V):

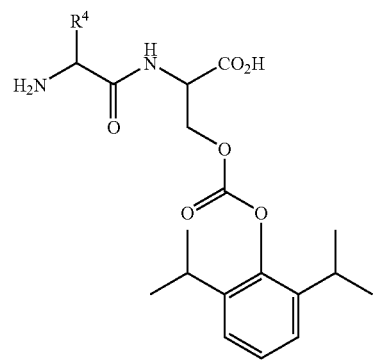

wherein R⁴ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl.

8. The compound of claim 7, wherein R⁴ is selected from the group consisting of hydrogen, methyl, isopropyl, isobutyl, sec-butyl, t-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl and 3-indolylmethyl.

9. The compound of claim 1 having structural Formula (VI):

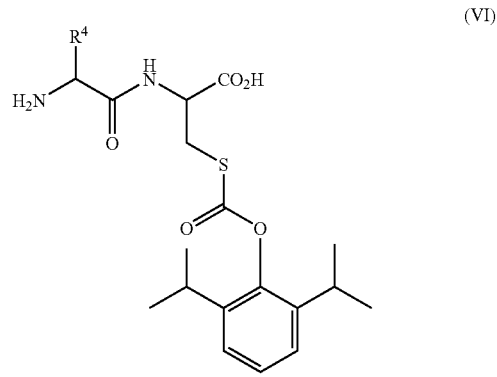

wherein R⁴ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl.

10. The compound of claim 9, wherein R⁴ is selected from the group consisting of hydrogen, methyl, isopropyl, isobutyl, sec-butyl, t-butyl, cyclopentyl, cyclohexyl, —CH₂OH, —CH(OH)CH₃, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl and 3-indolylmethyl.

11. The compound of claim 1 having structural Formula (VII):

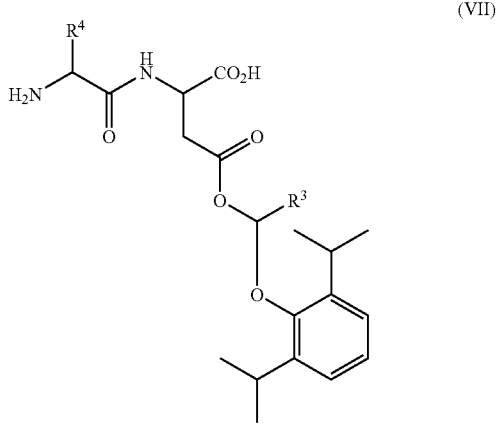

wherein R³ is hydrogen or methyl; and
R⁴ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl.

12. The compound of claim 11, wherein $R^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

13. A compound of Formula (VIII):

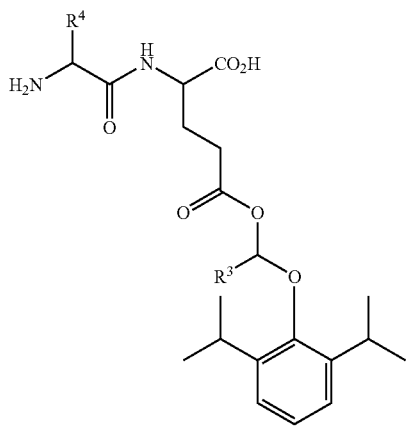

(VIII)

wherein $R^3$ is hydrogen or methyl; and $R^4$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl.

14. The compound of claim 13, wherein $R^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

15. The compound of claim 1 having structural Formula (IX):

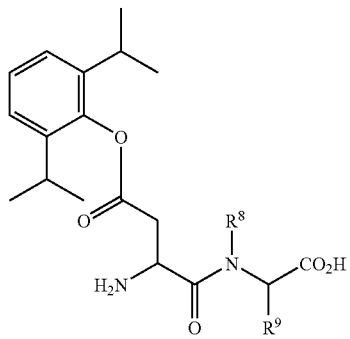

(IX)

wherein $R^8$ is hydrogen or methyl; and $R^9$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl, or optionally $R^8$ and $R^9$ together with the atoms to which they are bonded form a cycloheteroalkyl or substituted cycloheteroalkyl ring.

16. The compound of claim 15, wherein $R^8$ is hydrogen and $R^9$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

17. The compound of claim 15, wherein $R^8$ and $R^9$ together with the atoms to which they are bonded form an azetidine, pyrrolidine or piperidine ring.

18. The compound of claim 1 having structural Formula (X):

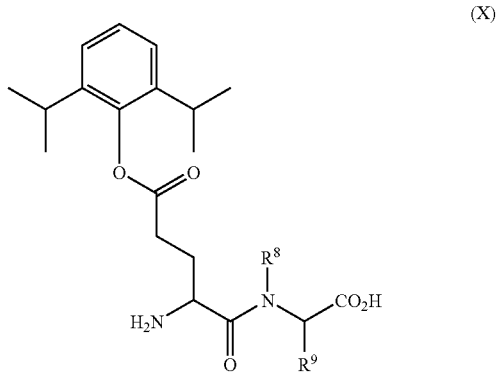

(X)

wherein $R^8$ is hydrogen or methyl; and $R^9$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl, or optionally $R^8$ and $R^9$ together with the atoms to which they are bonded form a cycloheteroalkyl or substituted cycloheteroalkyl ring.

19. The compound of claim 18, wherein $R^8$ is hydrogen and $R^9$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

20. The compound of claim 19, wherein $R^8$ and $R^9$ together with the atoms to which they are bonded form an azetidine, pyrrolidine or piperidine ring.

21. The compound of claim 1 having structural Formula (XI):

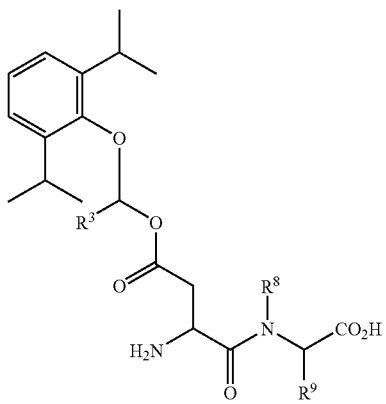

wherein $R^3$ is hydrogen or methyl;
$R^8$ is hydrogen or methyl; and
$R^9$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl, or optionally $R^8$ and $R^9$ together with the atoms to which they are bonded form a cycloheteroalkyl or substituted cycloheteroalkyl ring.

22. The compound of claim 21, wherein $R^3$ is hydrogen.

23. The compound of claim 22, wherein $R^8$ is hydrogen and $R^9$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

24. The compound of claim 22, wherein $R^8$ and $R^9$ together with the atoms to which they are bonded form an azetidine, pyrrolidine or piperidine ring.

25. The compound of claim 1 having structural Formula (XII):

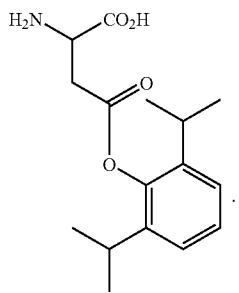

26. The compound of claim 1 having structural Formula (XIII):

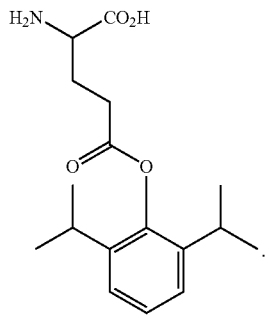

27. The compound of claim 1 having structural Formula (XIV):

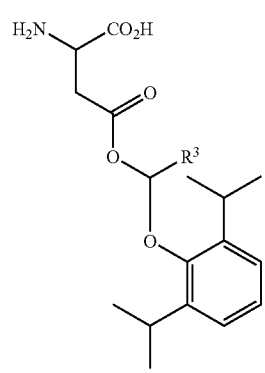

wherein $R^3$ is hydrogen or methyl.

28. The compound of claim 1 having Formula (XV):

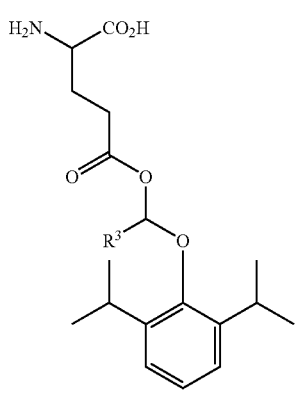

wherein $R^3$ is hydrogen or methyl.

29. A compound of Formula (II):

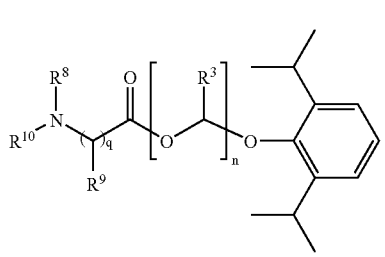

(II)

or a pharmaceutically acceptable salt, hydrate, solvate or N-oxide thereof, wherein:

n is 0 or 1;

$R^{10}$ is hydrogen or $[R^5NH(CHR^4)_pC(O)]—$;

p and q are independently 1 or 2;

$R^3$ is selected from the group consisting of hydrogen, alkyl, substituted alkyl, alkoxycarbonyl, aryl, substituted aryl, arylalkyl, carbamoyl, substituted carbamoyl, cycloalkyl, substituted cycloalkyl, cycloheteroalkyl, heteroaryl, substituted heteroaryl and heteroarylalkyl;

each $R^4$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^4$ and $R^5$ are attached to adjacent atoms then $R^4$ and $R^5$ together with the atoms to which they are bonded form a cycloheteroalkyl or substituted cycloheteroalkyl ring;

$R^5$ is selected from the group consisting of hydrogen, $R^6—$, $R^6C(O)—$ and $R^{10}C(O)—$;

$R^6$ is selected from the group consisting of alkyl, substituted alkyl, aryl, substituted aryl, arylalkyl, substituted arylalkyl, cycloalkyl, substituted cycloalkyl, cycloheteroalkyl, heteroaryl, substituted heteroaryl and heteroarylalkyl;

$R^8$ is selected from the group consisting of hydrogen, alkyl, substituted alkyl, aryl, substituted aryl, arylalkyl, cycloalkyl, substituted cycloalkyl, cycloheteroalkyl, heteroaryl, substituted heteroaryl and heteroarylalkyl;

each $R^9$ is independently selected from the group consisting of hydrogen, alkyl, substituted alkyl, alkoxy, substituted alkoxy, acyl, substituted acyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl, or optionally, when $R^8$ and $R^9$ are attached to adjacent atoms then $R^8$ and $R^9$ together with the atoms to which they are bonded form a cycloheteroalkyl or substituted cycloheteroalkyl ring;

with the proviso that:

when $R^{10}$ is hydrogen then n is 1.

30. The compound of claim 29, wherein n is 0.

31. The compound of claim 29 having structural Formula (XVI):

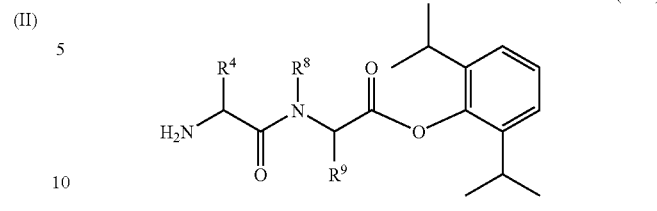

(XVI)

wherein $R^4$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl;

$R^8$ is hydrogen or methyl; and $R^9$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl, or optionally, $R^8$ and $R^9$ together with the atoms to which they are bonded form a cycloheteroalkyl or substituted cycloheteroalkyl ring.

32. The compound of claim 31, wherein $R^8$ is hydrogen and $R^9$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

33. The compound of claim 31, wherein $R^8$ and $R^9$ together with the atoms to which they are bonded form an azetidine, pyrrolidine or piperidine ring.

34. The compound of claim 31, wherein $R^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

35. The compound of claim 32 or 33, wherein both the N— and C-terminal amino acid residues are of the L-configuration.

36. The compound of claim 35, wherein $R^9$ is hydrogen, $R^9$ is methyl and $R^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

37. The compound of claim 35, wherein $R^8$ is hydrogen, $R^9$ is —CH$_2$CONH$_2$ and $R^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

38. The compound of claim 35, wherein $R^8$ is hydrogen, $R^9$ is benzyl and $R^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

39. The compound of claim 35, wherein R$^8$ is hydrogen, R$^9$ is 4-hydroxybenzyl and R$^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

40. The compound of claim 29 having structural Formula (XVII):

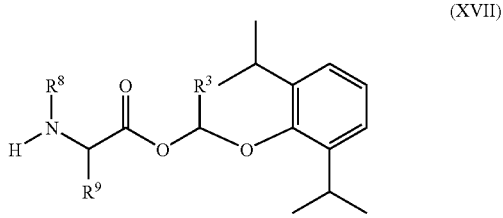

(XVII)

wherein R$^3$ is hydrogen or methyl;

R$^9$ is hydrogen or methyl; and

R$^9$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl, or optionally R$^8$ and R$^9$ together with the atoms to which they are bonded form a cycloheteroalkyl or substituted cycloheteroalkyl ring.

41. The compound of claim 40, wherein R$^8$ is hydrogen and R$^9$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

42. The compound of claim 40, wherein R$^8$ and R$^9$ together with the atoms to which they are bonded form an azetidine, pyrrolidine or piperidine ring.

43. The compound of claim 29 having structural Formula (XVIII):

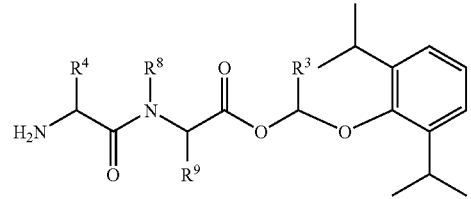

(XVIII)

wherein R$^3$ is hydrogen or methyl;

R$^4$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl;

R$^8$ is hydrogen or methyl; and

R$^9$ is selected from the group consisting of hydrogen, alkanyl, substituted alkanyl, aryl, substituted aryl, arylalkanyl, substituted arylalkanyl, cycloalkanyl, heteroarylalkanyl and substituted heteroarylalkanyl, or optionally, R$^8$ and R$^9$ together with the atoms to which they are bonded form a cycloheteroalkyl or substituted cycloheteroalkyl ring.

44. The compound of claim 43, wherein R$^8$ is hydrogen and R$^9$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

45. The compound of claim 43, wherein R$^8$ and R$^9$ together with the atoms to which they are bonded form an azetidine, pyrrolidine or piperidine ring.

46. The compound of claim 44 or 45, wherein R$^4$ is selected from the group consisting of hydrogen, methyl, isopropyl, isobutyl, sec-butyl, t-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl and 3-indolylmethyl.

47. A method for treating or reducing risk of acquiring migraine, nausea, vomiting, anxiety, seizures, convulsions, trauma of the central nervous system, and neurodegenerative conditions selected from the group consisting of Friedrich's disease, Parkinson's disease, Alzheimer's disease, Huntington's disease, amyotrophic lateral sclerosis (ALS), multiple sclerosis (MS) and Pick disease in a patient, comprising administering to a patient in need of such treatment or reduction in risk a therapeutically effective amount of a compound according to claim 1 or 29.

48. A pharmaceutical composition comprising a therapeutically effective amount of a compound according to claim 1 or 29 and a pharmaceutically acceptable vehicle.

* * * * *